United States Patent
Akasaka et al.

[11] Patent Number: 5,849,912
[45] Date of Patent: Dec. 15, 1998

[54] BIPHENYL DERIVATIVES

[75] Inventors: Kozo Akasaka; Masahiro Yonaga, both of Ibaraki, Japan; Akiharu Kajiwara, London, United Kingdom; Kunizo Higurashi, Chiba, Japan; Kohshi Ueno, Ibaraki, Japan; Satoshi Nagato, London, United Kingdom; Makoto Komatsu, Ibaraki, Japan; Noritaka Kitazawa, Ibaraki, Japan; Masataka Ueno, Ibaraki, Japan; Yoshiharu Yamanishi, Ibaraki, Japan; Yoshimasa Machida, London, United Kingdom; Yuki Komatsu, Ibaraki, Japan; Naoyuki Shimomura, Ibaraki, Japan; Norio Minami, Ibaraki, Japan; Toshikazu Shimizu, Ibaraki, Japan; Atsushi Nagaoka, Ibaraki, Japan

[73] Assignee: Eisai Co., Ltd., Tokyo, Japan

[21] Appl. No.: 855,790

[22] Filed: May 12, 1997

Related U.S. Application Data

[63] Continuation of Ser. No. 409,084, Mar. 22, 1995, abandoned.

[30] Foreign Application Priority Data

Mar. 29, 1994 [JP] Japan ................................. 6-81030
Nov. 22, 1994 [JP] Japan ............................... 6-311347
Dec. 27, 1994 [JP] Japan ............................... 6-336919

[51] Int. Cl.$^6$ .................. C07D 401/06; C07D 295/073; C07D 295/088; C07D 295/112

[52] U.S. Cl. ..................... 544/360; 544/365; 544/372; 544/374; 544/379; 544/389; 544/392; 544/394; 544/395; 514/252; 514/255

[58] Field of Search .................................. 544/360, 365, 544/372, 374, 379, 389, 392, 394, 395; 514/252, 255

[56] References Cited

U.S. PATENT DOCUMENTS

| | | | |
|---|---|---|---|
| 3,381,009 | 4/1968 | Palazzo et al. | 544/362 |
| 3,558,629 | 1/1971 | Archer et al. | 544/395 |
| 3,692,821 | 9/1972 | Sarett et al. | 544/399 |
| 4,125,612 | 11/1978 | Sherlock | 424/250 |
| 4,831,034 | 5/1989 | Barreau et al. | 514/255 |
| 5,021,421 | 6/1991 | Hino et al. | 514/254 |
| 5,428,037 | 6/1995 | Pascal et al. | 514/252 |

FOREIGN PATENT DOCUMENTS

| | | |
|---|---|---|
| A20100257 | 2/1984 | European Pat. Off. |
| 0196132 | 10/1986 | European Pat. Off. |
| A10256936 | 2/1988 | European Pat. Off. |
| A20385237 | 9/1990 | European Pat. Off. |
| A20574271 | 12/1993 | European Pat. Off. |
| A2017698 | 10/1979 | United Kingdom . |
| WO92/19624 | 11/1992 | WIPO . |
| WO9424116 | 10/1994 | WIPO . |

OTHER PUBLICATIONS

Chemical Abstracts, Abstract No. 6439u, vol. 114, No. 1, (Jan. 7, 1991), Barlin et al.
Registry Handbook 1974 Suppl.: Chem. Abs. Service, ACS XP002034348 (RN: 47497–49–4, 47069–47–6).
Duncan et al, *Chemical Abstracts*, vol. 70, No. 47401 S (1969).
Duncan et al, *J. Med. Chem.* 12(1), pp. 25–29 (1969).
Zhang et al, *Chemical Abstracts*, vol. 106, No. 119384 (1987).

*Primary Examiner*—Emily Bernhardt
*Attorney, Agent, or Firm*—Birch, Stewart, Kolasch & Birch, LLP

[57] ABSTRACT

A biphenyl derivative represented by the following formula (I) or a pharmacologically acceptable salt thereof:

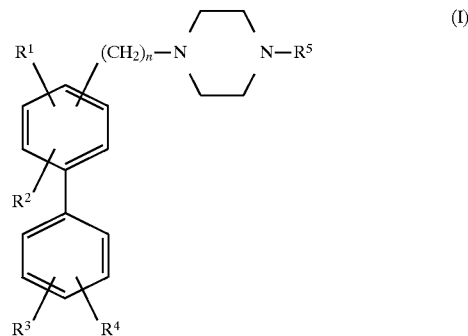

wherein $R^1$, $R^2$, $R^3$, $R^4$, and $R^5$ are defined in the specification, is clinically useful for treating and ameliorating mental disorders such as cerebrovascular disorder, aggressive behavior due to senile dementia, mental excitation, poriomania, delirium, hallucination, hyperkinesia, schizophrenia, emotional disturbance, depression, neurosis, psychophysiologic disorder and anxiety neurosis. The compounds exhibit dopamine 2 receptor antagonism and/or serotonin 2 receptor antagonism.

6 Claims, No Drawings

BIPHENYL DERIVATIVES

This application is a continuation of application Ser. No. 08/409,084 filed on Mar. 22, 1995, now abandoned.

BACKGROUND OF THE INVENTION

1. Field of the Invention

The present invention relates to biphenyl derivatives. More particularly, it relates to biphenyl derivatives which exhibit dopamine 2 receptor antagonism and/or serotonin 2 receptor antagonism and which are clinically useful as therapeutic and ameliorative agents for mental disorders such as cerebrovascular disorder, aggressive behavior due to senile dementia, mental excitation, poriomania, delirium, hallucination, hyperkinesia, schizophrenia, emotional disturbance, depression, neurosis, psychophysiologic disorder and anxiety neurosis.

2. Description of the Related Art

Mental disorders such as cerebrovascular disorder and dementia are frequently found in the aged, which becomes a significant problem with the approach of an aging society. In many cases, these diseases are accompanied with mental and/or behavior disorders which specifically appear as delirium, hallucination, hyperkinesia, poriomania, mental excitation or other sign or symptom. These signs and symptoms not only have an adverse effect on a patient himself, but also necessitate everyday care, imposing a heavy burden on the people around the patient. Under these circumstances, the development of a highly clinically useful medicine which can treat the above mental disorders medically has been expected not only by patients and their families, but also socially.

Only Tiapride is now authorized as a therapeutic and ameliorative agent for the above diseases, and Haloperidol which is an antischizophrenic drug is also used, though the diseases are not included in the indications for which the drug is efficacious.

As novel compounds having an antipsychotic activity, benzisothiazole derivatives and benzisoxazole derivatives are disclosed in European Patent Publication-A No. 196132, and pyridine derivatives are disclosed in U.S. Pat. No. 5021421.

Tiapride and Haloperidol are medicines exhibiting dopamine 2 ($D_2$) receptor antagonism. A medicine of this type has a problem of causing extrapyramidal syndrome including dystonia (hypermyotonia or muscle hypotonia), hypokinesis (akinesia), hyperkinesia (abnormal movement) and so forth as an adverse reaction, though the medicine is clinically efficacious.

Risperidone which is a representative example of the benzisoxazole derivative disclosed in the above European Patent Publication-A No. 196132 is authorized as an antischizophrenic drug in the United States, the United Kingdom and Canada. However, this drug is problematic in that blood-pressure drop occurs as an adverse reaction owing to the high $\alpha_1$ blocking activity of the drug and that the $QT_c$ interval in electrocardiogram is lengthened to induce arrhythmia, being undesirable particularly when administered to a patient of advanced age.

The pyridine derivative disclosed in the above U.S. Pat. No. 5021421 also exhibits potent dopamine 2 receptor antagonism and is therefore feared to cause extrapyramidal syndrome like Tiapride or Haloperidol. Further, the pyridine derivative has not been used clinically as yet, so that its safeness in prolonged application is not apparent.

As described above, there has not been found any therapeutic and ameliorative agent for mental disorders such as cerebrovascular disorder, aggressive behavior due to senile dementia, mental excitation, poriomania, delirium, hallucination, hyperkinesia, schizophrenia, emotional disturbance, depression, neurosis, psychophysiologic disorder and anxiety neurosis, which has high clinical usefulness and is excellent in safeness.

DISCLOSURE OF THE INVENTION

Summary of the Invention

An object of the present invention is to provide novel biphenyl derivatives and pharmacologically acceptable salts thereof which exhibit dopamine 2 receptor antagonism and/or serotonin 2 receptor antagonism, are clinically useful as therapeutic and ameliorative agents for mental diseases, is improved in the disadvantageous extrapyramidal syndrome as compared with dopamine 2 receptor antagonists of the prior art such as Tiapride and Haloperidol, and is freed from the adverse reactions caused by the above benzisoxazole derivative (such as Risperidone), for example, blood-pressure drop and induction of arrhythmia.

Another object of the present invention is to provide processes for the preparation of the biphenyl derivatives described above.

Another object of the present invention is to provide phenylpiperazine derivatives and salts thereof which are useful as intermediates in the production of the biphenyl derivatives and pharmacologically acceptable salts thereof described above.

The present inventors have extensively studied to find an extremely safe and useful therapeutic and ameliorative agent for mental disorders which exhibits dopamine 2 receptor antagonism and does not cause extrapyramidal syndrome, blood-pressure drop, induction of arrhythmia or other adverse reaction, with their attention being paid to compounds exhibiting both dopamine 2 receptor antagonism and serotonin 2 receptor antagonism. As a result, they have found that specific biphenyl derivatives and pharmacologically acceptable salts thereof which are novel compounds have an excellent therapeutic and ameliorative effect on mental disorders and are excellent in safeness, solving the above problems. The present invention has been accomplished on the basis of this finding.

Thus, the present invention provides a biphenyl derivative represented by the following formula (I) or a pharmacologically acceptable salt thereof:

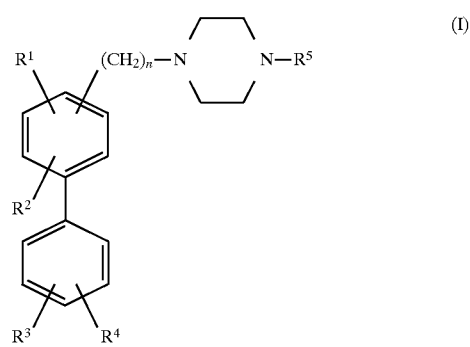

wherein $R^1$ represents a hydrogen atom, a halogen atom, a hydroxyl group, an amino group, a cyano group, a pyrrolidyl group, a lower alkyl group, a halogenated lower alkyl group, a cyano lower alkyl group, a hydroxy lower alkyl group, an amino lower alkyl group, a cycloalkyl group, a cycloalkylalkyl group, a lower alkoxyalkyl group, a heteroarylalkyl group, a halogenated heteroarylalkyl group, a lower acylalkyl group, a heteroarylalkoxyalkyl group, a cycloalkyloxyalkyl group, an aralkyloxyalkyl group, an alkenyloxyalkyl group, a lower alkoxycarbonylalkyl group, a lower alkoxyalkoxyalkyl group, an arylhydroxyalkyl group, a hydroxyheteroarylalkyl group, a cycloalkylalkoxyalkyl group, an alkenyl group, a halogenated alkenyl group, an alkynyl group, an aralkyl group, a halogenated aralkyl group, a hydroxyaralkyl group, a halogenated hydroxyiminoaralkyl group, a lower alkoxy group, a halogenated lower alkoxy group, a lower alkoxyalkoxy group, an aryl group, a hydroxyaryl group, a halogenated aryl group, a lower alkoxyaryl group, a heteroaryl group, a hydroxyheteroaryl group, a halogenated heteroaryl group, a lower alkoxyheteroaryl group, a formyl group, a lower acyl group, an aromatic acyl group, a heteroaromatic acyl group, an aralkylcarbonyl group, a cycloalkylalkylcarbonyl group, a heteroarylalkylcarbonyl group, a halogenated aralkylcarbonyl group, a lower alkoxycarbonyl group, an aryloxycarbonyl group, a lower alkylamino group, a lower alkylsulfonylamino group, a halogenated lower alkylsulfonylamino group, an arylsulfonylamino group, a halogenated arylsulfonylamino group, an aralkylsulfonyl amino group, a cycloether group, a lower cyclic acetal group, a lower cyclic thioacetal group, a lower alkylsulfinyl group, an arylsulfinyl group, an aralkylsulfinyl group, a heteroarylsulfinyl group, a lower alkylsulfonyl group, an arylsulfonyl group, an aralkylsulfonyl group, a heteroarylsulfonyl group, a cycloalkylsulfonyl group, an aminosulfonyl group, a lower alkylaminosulfonyl group, an arylaminosulfonyl group, a pyrrolidylsulfonyl group, a cycloalkylaminosulfonyl group, a halogenated lower alkylsulfonyl group, a halogenated aryloxy lower alkylsulfonyl group or a cyano lower alkylsulfonyl group;

$R^2$ and $R^3$ may be the same or different from each other and each represents a hydrogen atom, a halogen atom, a cyano group, a hydroxyl group, a lower alkyl group, a halogenated lower alkyl group, a lower alkoxyalkyl group, a lower alkoxy group or a halogenated lower alkoxy group;

$R^4$ represents a hydrogen atom, a halogen atom, a lower alkyl group, a hydroxy lower alkyl group, a hydroxyiminomethyl group or a formyl group;

$R^5$ represents a hydrogen atom, a lower alkyl group, a halogenated lower alkyl group, a hydroxy lower alkyl group, a heteroarylalkyl group, an aralkyl group, a lower alkoxycarbonyl group or an aryloxycarbonyl group; and n is 0 or an integer of 1 to 3.

Among the biphenyl derivatives and the pharmacologically acceptable salts thereof described above, those represented by the following formula (II) and the pharmacologically acceptable salts thereof are preferable:

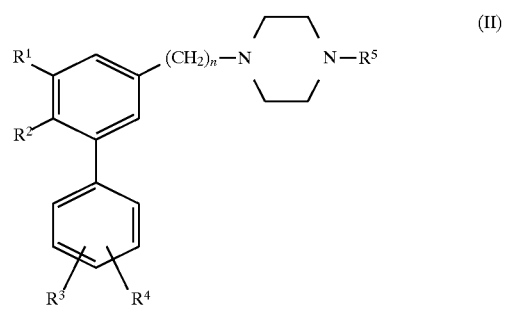

wherein $R^1$, $R^2$, $R^3$, $R^4$, $R^5$ and n are each as defined above.

Among the biphenyl derivatives and the pharmacologically acceptable salts thereof described above, those represented by the above formula (I), wherein $R^1$ is a halogenated lower alkyl group or a lower alkylsulfonylamino group; $R^2$ is a halogen atom or a lower alkoxy group; $R^3$ is a halogen atom, a lower alkyl group or a cyano group; $R^4$ is a hydrogen atom or a halogen atom; $R^5$ is a hydrogen atom, a lower alkyl group or a hydroxy lower alkyl group; and n is 0, and the pharmacologically acceptable salts thereof are particularly preferable.

Among the biphenyl derivatives and the pharmacologically acceptable salts thereof described above, those represented by the following formula (II') and the pharmacologically acceptable salts thereof are particularly preferable:

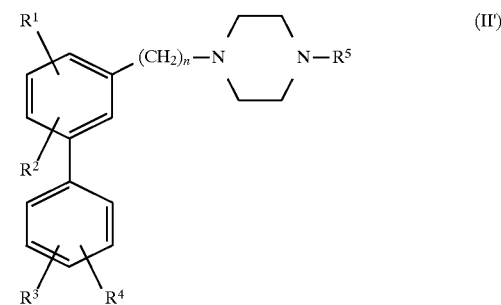

wherein $R^1$ represents a hydrogen atom, a halogen atom, a hydroxyl group, an amino group, a lower alkyl group, a halogenated lower alkyl group, a lower alkoxy group, a halogenated lower alkoxy group, a lower alkoxyalkyl group, a lower alkoxyalkoxy group, an aryl group, an aralkyl group, a heteroaryl group, a heteroarylalkyl group, a halogenated heteroarylalkyl group, a cyano lower alkyl group, a hydroxy lower alkyl group, an amino lower alkyl group, a lower alkoxycarbonyl group, an aryloxycarbonyl group, a cyano group, a formyl group, a lower acyl group, an aralkylcarbonyl group, a cycloether group, an alkenyl group, an alkynyl group, a lower alkylsulfinyl group, a lower alkylsulfonyl group, a lower alkylaminosulfonyl group, an arylaminosulfonyl group, a lower alkylsulfonylamino group, a halogenated lower alkylsulfonylamino group or an arylsulfonylamino group;

$R^2$ and $R^3$ may be the same or different from each other and each represents a hydrogen atom, a halogen atom, a lower alkyl group, a halogenated lower alkyl group, a lower alkoxy group, a halogenated lower alkoxy group or a cyano group;

$R^4$ represents a hydrogen atom or a halogen atom;

$R^5$ represents a hydrogen atom, a lower alkyl group, a halogenated lower alkyl group, a hydroxy lower alkyl group, a lower alkoxycarbonyl group or an aryloxycarbonyl group; and n is 0 or an integer of 1 to 3.

Further, the present invention provides a therapeutic and ameliorative agent for a mental disorder, which comprises the above-mentioned biphenyl derivative of the formula (I) or the pharmacologically acceptable salt thereof as an active ingredient.

Furthermore, the present invention provides a pharmacological composition which comprises a therapeutically or amelioratively effective amount of the above-mentioned biphenyl derivative of the formula (I) or the pharmacologically acceptable salt thereof, and a pharmacologically acceptable vehicle; an use of the above-mentioned biphenyl derivative of the formula (I) or the pharmacologically acceptable salt thereof for the making of a medicament for treating or ameliorating a disease against which dopamine 2 receptor antagonism and/or serotonin 2 receptor antagonism is efficacious; and a method for treating or ameliorating a disease which comprises administering a pharmaceutically effective amount of the above-mentioned biphenyl derivative of the formula (I) or the pharmacologically acceptable salt thereof to a patient suffering from a disease against which dopamine 2 receptor antagonism and/or serotonin 2 receptor antagonism is efficacious.

In addition, the present invention provides processes for the production of the above-mentioned biphenyl derivatives, which will be specifically described below.

The present invention provides a phenylpiperazine derivative represented by the following general formula (XXVII) or a salt thereof:

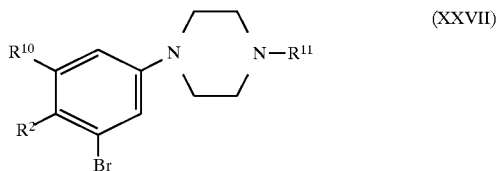

(XXVII)

wherein $R^2$ represents a hydrogen atom, a halogen atom, a cyano group, a hydroxyl group, a lower alkyl group, a halogenated lower alkyl group, a lower alkoxyalkyl group, a lower alkoxy group or a halogenated lower alkoxy group; $R^{10}$ represents a halogenated lower alkyl group, a hydroxy lower alky group, a halogen atom, a lower alkylsulfonyl group, a lower alkoxycarbonyl group, a carboxyl group, an alkenyl group, a (pyridylthio)carbonyl group or a lower acyl group; and $R^{11}$ represents a hydrogen atom, a lower alkyl group, a halogenated lower alkyl group, a hydroxy lower alkyl group, a tri(lower alkyl)silyloxy lower alkyl group, a heteroarylalkyl group, an aralkyl group, a lower alkoxycarbonyl group, an aryloxycarbonyl group or an amino-protecting group.

Among the phenylpiperazine derivatives and salts thereof described above, those represented by the above formula (XXVII), wherein $R^2$ is as defined above; $R^{10}$ represents a halogenated lower alkyl group or a hydroxy lower alkyl group; and $R^{11}$ represents a hydrogen atom, a hydroxy lower alkyl group or an amino-protecting group, and salts thereof are preferable.

Among the phenylpiperazine derivatives and salts thereof described above, those represented by the above formula (XXVII), wherein $R^2$ represents a hydrogen atom, a halogen atom, a lower alkyl group, a halogenated lower alkyl group, a lower alkoxy group, a halognated lower alkoxy group or a cyano group; $R^{10}$ represents a halogenated lower alkyl group or a hydroxy lower alkyl group; and $R^{11}$ represents a hydrogen atom, a hydroxy lower alkyl group or an amino-protecting group, and salts thereof are particularly preferable.

Further scope and applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

With respect to the above definition of the above formulas, particular examples of the halogen atom include chlorine atom, fluorine atom, bromine atom and iodine atom, among which fluorine atom and chlorine atom are preferable. Particular examples of the lower alkyl group include alkyl groups having 1 to 6 carbon atoms, such as methyl group, ethyl group, n-propyl group, i-propyl group, n-butyl group, i-butyl group, t-butyl group, pentyl group and hexyl group; the halogenated lower alkyl group is a lower alkyl group described above in which at least one halogen atom substitutes for the hydrogen atom, and particular examples thereof include fluoromethyl group, difluoromethyl group, trifluoromethyl group, fluoroethyl group, fluoropropyl group, chlorobutyl group and chloropentyl group; the lower alkoxy group is a lower alkyl group described above to which an oxygen atom is bonded, and particular examples thereof include methoxy group, ethoxy group and propoxy group; the halogenated lower alkoxy group is a lower alkoxy group described above in which at least one halogen atom substitutes for the hydrogen atom, and particular examples thereof include fluoromethoxy group and chloroethoxy group; the lower alkoxyalkyl group is a lower alkyl group described above in which a lower alkoxy group substitutes for the hydrogen atom, and particular examples thereof include methoxymethyl group, methoxyethyl group and methoxypropyl group; the lower alkoxyalkoxy group is a lower alkoxy group described above in which a lower alkoxy group substitutes for the hydrogen atom bonded to the carbon atom, and particular examples thereof include methoxymethoxy group, methoxyethoxy group and methoxypropoxy group; particular examples of the aryl group include phenyl group, tolyl group (—$C_6H_4CH_3$), xylyl group [—$C_6H_3(CH_3)_2$], methoxyphenyl group, chlorophenyl group, bromophenyl group, fluorophenyl group, nitrophenyl group and cyanophenyl group; particular examples of the aralkyl group include benzyl group, methylbenzyl group, phenethyl group and phenylpropyl group; particular examples of the heteroaryl group include thienyl group, furanyl group, pyranyl group, imidazolyl group, thiazolyl group, pyridyl group and pyrazolyl group; particular examples of the heteroarylalkyl group include thienylmethyl group, furfuryl group, imidazolylmethyl group, thiazolylmethyl group, pyridylmethyl group and pyrazylmethyl group; the halogenated heteroarylalkyl group is a heteroarylalkyl group described above in which at least one halogen atom substitutes for the hydrogen atom; the cyano lower alkyl group is a lower alkyl group described above in which at least one cyano group substitutes for the hydrogen atom; the hydroxy lower alkyl group is a lower alkyl group described above in which at least one hydroxyl group substitutes for the hydrogen atom; the amino lower alkyl group is a lower alkyl group described above in which at least one amino group substitutes for the hydrogen atom; the lower alkoxycarbonyl group is a lower alkoxy group described above to which a carbonyl group is bonded, and particular examples thereof include methoxy carbonyl group and ethoxycarbonyl group; the aryloxycarbonyl group is an aryl group described above to which an oxygen atom having a carbonyl group bonded thereto is bonded, and particular examples thereof include phenoxycarbonyl group, tolyloxycarbonyl group and xylyloxycarbonyl group; the lower acyl group is a lower alkyl group which has 1 to 6 carbon atoms and to which a carbonyl group is bonded, and particular examples thereof include acetyl group, propionyl group, butyryl group and valeryl group; particular examples of the aromatic acyl group include benzoyl group, anisoyl group, nitrobenzoyl group, chlorobenzoyl group, cyanobenzoyl group, toluoyl group and xyloyl group; particular examples of the cyclo-ether group include tetrahydrofuranyl group and tetrahydropyranyl group; particular examples of the alkenyl group include vinyl group, propenyl group and butenyl group; a particular example of the alkynyl group includes propargyl group; the lower alkylsulfinyl group is a lower alkyl group described above to which a sulfinyl group (—SO—) is bonded, and particular examples thereof include methanesulfinyl group and ethanesulfinyl group; the lower alkylsulfonyl group is a lower alkyl group described above to which a sulfonyl group (—SO$_2$—) is bonded, and particular examples thereof include methanesulfonyl group and ethanesulfonyl group; the lower alkylaminosulfonyl group is an aminosulfonyl group (>NSO$_2$—) in which the N atom has one lower alkyl group described above and one hydrogen atom bonded thereto, or two lower alkyl groups described above bonded thereto, and particular examples thereof include methylaminosulfonyl group and dimethylaminosulfonyl group; the arylaminosulfonyl group is an aminosulfonyl group in which the N atom has one aryl group described above bonded thereto, or two aryl groups described above bonded thereto, and particular examples thereof include phenylaminosulfonyl group and diphenylaminosulfonyl group; the lower alkylsulfonylamino group is a lower alkyl group described above to which a sulfonylamino group (—SO$_2$NH—) is bonded, and particular examples thereof include methanesulfonylamino group, ethanesulfonylamino group, propanesulfonylamino group and butanesulfonylamino group; the halogenated lower alkylsulfonylamino group is a lower alkylsulfonylamino group described above in which at least one halogen atom substitutes for the hydrogen atom; the arylsulfonylamino group is an aryl group described above to which a sulfonylamino group (—SO$_2$NH—) is bonded, and particular examples thereof include benzenesulfonylamino group and toluenesulfonylamino group; the cyclic acetal group is, i.e., an alkyldioxymethyl group, and examples thereof include 1,3-dioxolan-2-yl group and 1,3-dioxan-2-yl group; and the cyclic thioacetal group is, i.e., an alkyldithiomethyl group, and an example thereof includes 1,3-dithian-2-yl group. In particular, it is preferable that $R^1$ be a halogenated lower alkyl group or a lower alkylsulfonylamino group, $R^2$ be a halogen atom or a lower alkoxy group, $R^3$ be a halogen atom, a lower alkyl group or a cyano group, $R^4$ be a hydrogen atom or a halogen atom, $R^5$ be a hydrogen atom, a lower alkyl group or a hydroxy lower alkyl group, and n be 0. Further, it is preferable that the substituent represented by formula —(CH$_2$)-piperazine-$R^5$ be bonded at the 3-position of the 1,1'-biphenyl skeleton, though the position of substitution is not particularly limited.

More specific examples of the biphenyl derivative represented by the above formula (I) or (II) according to the present invention include the following compounds, though the derivative represented by the above formula (I) or (II) is not limited to them:

(1) 1-[3-(2-cyanophenyl)-4-chloro-5-(1-fluoropropyl)]phenylpiperazine,
(2) 1-(2-hydroxyethyl)-4-[3-(2-cyanophenyl)-4-chloro-5-(1-fluoropropyl)]phenylpiperazine,
(3) 1-ethyl-4-[3-(2-tolyl)-4-chloro-5-ethoxycarbonyl]phenylpiperazine,
(4) 1-ethyl-4-[3-(2-tolyl)-4-chloro-5-amino]phenylpiperazine,
(5) 1-ethyl-4-[3-(2-tolyl)-4-chloro-5-propanesulfonylamino]phenylpiperazine,
(6) 1-ethyl-4-[3-(2-tolyl)-4-chloro-5-ethanesulfonylamino]phenylpiperazine,
(7) 1-ethyl-4-[3-(2-tolyl)-4-chloro-5-butanesulfonylamino]phenylpiperazine,
(8) 1-methyl-4-[3-(2-cyanophenyl)-4-chloro-5-(1-fluoropropyl)]phenylpiperazine,
(9) 1-ethyl-4-[3-(2-cyanophenyl)-4-chloro-5-(1-fluoropropyl)]phenylpiperazine,
(10) 1-methyl-4-[3-(2-chlorophenyl)-4-chloro-5-(1-fluoropropyl)]phenylpiperazine,
(11) 1-(2-hydroxyethyl)-4-[3-(2-chlorophenyl)-4-chloro-5-(1-fluoropropyl)]phenylpiperazine,
(12) 1-ethyl-4-[3-(2-chlorophenyl)-4-chloro-5-(1-fluoropropyl)]phenylpiperazine,
(13) 1-methyl-4-[3-(2-tolyl)-4-chloro-5-(1-fluoropropyl)]phenylpiperazine,
(14) 1-(2-hydroxyethyl)-4-[3-(2-tolyl)-4-chloro-5-(1-fluoropropyl)]phenylpiperazine,
(15) 1-ethyl-4-[3-(2-tolyl)-4-chloro-5-(1-fluoropropyl)]phenylpiperazine,
(16) 1-methyl-4-[3-(2-tolyl)-4-chloro-5-ethanesulfonylamino]phenylpiperazine,
(17) 1-methyl-4-[3-(2-tolyl)-4-chloro-5-propanesulfonylamino]phenylpiperazine,
(18) 1-methyl-4-[3-(2-tolyl)-4-chloro-5-butanesulfonylamino]phenylpiperazine,
(19) 1-ethyl-4-[3-(2-chlorophenyl)-4-chloro-5-ethanesulfonylamino]phenylpiperazine,
(20) 1-ethyl-4-[3-(2-chlorophenyl)-4-chloro-5-propanesulfonylamino]phenylpiperazine,
(21) 1-ethyl-4-[3-(2-chlorophenyl)-4-chloro-5-butanesulfonylamino]phenylpiperazine,
(22) 1-methyl-4-[3-(2-chlorophenyl)-4-chloro-5-ethanesulfonylamino]phenylpiperazine,
(23) 1-methyl-4-[3-(2-chlorophenyl)-4-chloro-5-propanesulfonylamino]phenylpiperazine,
(24) 1-methyl-4-[3-(2-chlorophenyl)-4-chloro-5-butanesulfonylamino]phenylpiperazine,
(25) 1-ethyl-4-[3-(4-fluorophenyl)-4-methoxy-5-ethanesulfonylamino]phenylpiperazine,
(26) 1-ethyl-4-(3-phenyl-4-methoxy-5-chloromethyl)phenylpiperazine,
(27) 1-ethyl-4-{3-phenyl-4-methoxy-5-[1-fluoro-(4-pentenyl)]}phenylpiperazine,
(28) 1-ethyl-4-[3-phenyl-4-methoxy-5-(1-fluorobutyl)]phenylpiperazine,
(29) 1-ethyl-4-[3-phenyl-4-methoxy-5-(1-fluoropentyl)]phenylpiperazine,
(30) 1-ethyl-4-[3-(2-tolyl)-4-chloro-5-(1-fluorobutyl)]phenylpiperazine,
(31) 1-ethyl-4-[3-(2-tolyl)-4-fluoro-5-(1-fluorobutyl)]phenylpiperazine,
(32) 1-ethyl-4-[3-(2-tolyl)-4-chloro-5-(1-fluoro-3-methylbutyl)]phenylpiperazine,

(33) 1-ethyl-4-[3-(2-tolyl)-4-chloro-5-(1-fluoroethyl)] phenylpiperazine,
(34) 1-methyl-4-[3-(2-tolyl)-4-chloro-5-(1-fluorobutyl)] phenylpiperazine,
(35) 1-ethyl-4-[3-(2-chlorophenyl)-4-chloro-5-(1-fluorobutyl)]phenylpiperazine,
(36) 1-ethyl-4-[3-(2-tolyl)-4-chloro-5-(1,1-difluoropropyl)] phenylpiperazine,
(37) 1-ethyl-4-(3,5-diphenyl-4-methoxy)phenylpiperazine,
(38) 1-ethyl-4-(3-phenyl-4-methoxy)phenylpiperazine,
(39) 1-ethyl-4-(3,5-diphenyl-4-hydroxy)phenylpiperazine,
(40) 1-ethyl-4-(3-phenyl-4-methoxy-5-propyl) phenylpiperazine,
(41) 1-ethyl-4-(3,5-diphenyl-4-isopropoxy) phenylpiperazine,
(42) 1-ethyl-4-(3-phenyl-4-isopropoxy)phenylpiperazine,
(43) 1-ethyl-4-(3-phenyl-4-hydroxy)phenylpiperazine,
(44) 1-ethyl-4-[2-methoxy-3-phenyl-5-(3-hydroxypropyl)] phenylpiperazine,
(45) 1-hydroxyethyl-4-(3,5-diphenyl-4-methoxy) phenylpiperazine,
(46) 1-ethyl-4-[3-(4-fluorophenyl)-4-methoxy-5-propyl)] phenylpiperazine,
(47) 1-ethyl-4-[3-phenyl-4-methoxy-5-(2-hydroxyethyl)] phenylpiperazine,
(48) 1-ethyl-4-[2-methoxy-3-phenyl-5-(2-hydroxyethyl)] phenylpiperazine,
(49) 1-ethyl-4-[3-phenyl-4-methoxy-5-(3-methoxypropyl)] phenylpiperazine,
(50) 1-ethyl-4-[3-phenyl-4-methoxy-5-(3-methoxymethoxypropyl)]phenylpiperazine,
(51) 1-ethyl-4-(3-phenyl-4-methoxy-5-ethyl) phenylpiperazine,
(52) 1-ethyl-4-[3-phenyl-4-methoxy-5-(3-cyanopropyl)] phenylpiperazine,
(53) 1-(2-fluoroethyl)-4-[3-(4-fluorophenyl)-4-methoxy-5-propyl]phenylpiperazine,
(54) 1-ethyl-4-[3-(4-methoxyphenyl)-4-methoxy-5-propyl] phenylpiperazine,
(55) 1-ethyl-4-(3-phenyl-4-methoxy-5-methoxycarbonyl) phenylpiperazine,
(56) 1-ethyl-4-[3-phenyl-4-methoxy-5-(2-hydroxypropyl)] phenylpiperazine,
(57) 1-ethyl-4-[3-phenyl-4-methoxy-5-(2-fluoroethyl)] phenylpiperazine,
(58) 1-ethyl-4-[3-phenyl-4-methoxy-5-(3-fluoropropyl)] phenylpiperazine,
(59) 1-ethyl-4-[3-(4-fluorophenyl)-4-methoxy-5-isopropyl] phenylpiperazine,
(60) 1-ethyl-4-[3-(4-fluorophenyl)-4-methoxy-6-isopropyl] phenylpiperazine,
(61) 1-ethyl-4-[3-phenyl-4-methoxy-5-(1-hydroxyisopropyl)]phenylpiperazine,
(62) 1-ethyl-4-[3-phenyl-4-methoxy-5-(1-butoxypropyl)] phenylpiperazine,
(63) 1-ethyl-4-(3-phenyl-4-methoxy-5-propionyl) phenylpiperazine,
(64) 1-ethyl-4-[3-phenyl-4-methoxy-5-(1-hydroxypropyl)] phenylpiperazine,
(65) 1-ethyl-4-[3-(2-fluorophenyl)-4-methoxy-5-propyl] phenylpiperazine,
(66) 1-ethyl-4-[3-(4-trifluoromethylphenyl)-4-methoxy-5-propyl]phenylpiperazine,
(67) 1-ethyl-4-[3-phenyl-4-methoxy-5-(1-fluoroisopropyl)] phenylpiperazine,
(68) 1-ethyl-4-[3-phenyl-4-methoxy-5-(2-hydroxyisopropyl)]phenylpiperazine,
(69) 1-ethyl-4-[3-phenyl-4-methoxy-5-(1-fluoropropyl)] phenylpiperazine,
(70) 1-ethyl-4-(3-phenyl-4-methoxy-5-cyano) phenylpiperazine,
(71) 1-ethyl-4-[3-phenyl-4-methoxy-5-(2-furanyl)] phenylpiperazine,
(72) 1-ethyl-4-[3-(2,4-difluorophenyl)-4-methoxy-5-propyl] phenylpiperazine,
(73) 1-ethyl-4-(3-phenyl-4-methoxy-5-phenylacetyl) phenylpiperazine,
(74) 1-ethyl-4-[3-phenyl-4-methoxy-5-(4-fluorophenyl) acetyl]phenylpiperazine,
(75) 1-ethyl-4-[3-phenyl-4-methoxy-5-(1-hydroxyphenethyl)]phenylpiperazine,
(76) 1-ethyl-4-[3-phenyl-4-methoxy-5-(2-tetrahydrofuranyl)]phenylpiperazine,
(77) 1-ethyl-4-[3-phenyl-4-methoxy-5-(1-fluorophenethyl)] phenylpiperazine,
(78) 1-ethyl-4-[3-phenyl-4-methoxy-5-(2-pyridyl)] phenylpiperazine,
(79) 1-ethyl-4-{3-phenyl-4-methoxy-5-[4-fluoro-(1-hydroxyimino)phenethyl]}phenylpiperazine,
(80) 1-ethyl-4-{3-phenyl-4-methoxy-5-[1-fluoro-2-(2-pyridyl)ethyl]}phenylpiperazine,
(81) 1-ethyl-4-[3-phenyl-4-methoxy-5-(1-propenyl)] phenylpiperazine,
(82) 1-ethyl-4-[3-(3-fluorophenyl)-4-methoxy-5-propyl] phenylpiperazine,
(83) 1-ethyl-4-(3-phenyl-4-methoxy-5-hydroxymethyl) phenylpiperazine,
(84) 1-ethyl-4-[3-phenyl-4-methoxy-5-(4-pyridyl)acetyl] phenylpiperazine,
(85) 1-ethyl-4-(3-phenyl-4-methoxy-5-methanesulfinyl) phenylpiperazine,
(86) 1-ethyl-4-(3-phenyl-4-methoxy-5-ethanesulfinyl) phenylpiperazine,
(87) 1-ethyl-4-(3-phenyl-4-methoxy-5-formyl) phenylpiperazine,
(88) 1-ethyl-4-[3-phenyl-4-methoxy-5-(1,3-dioxan-2-yl) phenylpiperazine,
(89) 1-ethyl-4-(3-phenyl-4-methoxy-5-cyclopropaneacetyl) phenylpiperazine,
(90) 1-ethyl-4-[3-phenyl-4-methoxy-5-(2-pyridylcarbonyl)] phenylpiperazine,
(91) 1-ethyl-4-(3-phenyl-4-methoxy-5-amino) phenylpiperazine,
(92) 1-ethyl-4-[3-phenyl-4-methoxy-5-(2-ethoxycarbonylethyl)]phenylpiperazine,
(93) 1-ethyl-4-[3-phenyl-4-methoxy-5-(2-pyridyl) hydroxymethyl]phenylpiperazine,
(94) 1-ethyl-4-(3-phenyl-5-propyl-6-methoxy) phenylpiperazine,
(95) 1-ethyl-4-[3-phenyl-4-methoxy-5-(2-acetylethyl)] phenylpiperazine,
(96) 1-ethyl-4-{3-phenyl-4-methoxy-5-[1-(2-pyridylmethoxy)propyl]}phenylpiperazine,
(97) 1-ethyl-4-[3-(2-tolyl)-4-methoxy-5-propyl] phenylpiperazine,
(98) 1-ethyl-4-(3-phenyl-4-methoxy-5-propylamino) phenylpiperazine,
(99) 1-(3-phenyl-4-hydroxy-5-phenylacetyl) phenylpiperazine,
(100) 1-ethyl-4-(3-phenyl-4-methoxy-5-benzylsulfinyl) phenylpiperazine,
(101) 1-ethyl-4-(3-phenyl-4-methoxy-5-benzenesulfonylamino)phenylpiperazine,
(102) 1-ethyl-4-{3-phenyl-4-methoxy-5-[1-fluoro-2-(4-pyridyl)ethyl]}phenylpiperazine, (103) 1-ethyl-4-[3-phenyl-4-methoxy-5-(N-ethanesulfonyl-N-methylamino)]phenylpiperazine,
(104) 1-ethyl-4-(3-phenyl-4-methoxy-5-ethylaminosulfonyl)phenylpiperazine,
(105) 1-ethyl-4-(3-phenyl-4-methoxy-5-aminosulfonyl)phenylpiperazine,
(106) 1-(3-phenyl-4-methoxy-5-phenylacetyl)phenylpiperazine,
(107) 1-benzyl-4-(3-phenyl-4-methoxy-5-phenylacetyl)phenylpiperazine,
(108) 1-ethyl-4-[3-phenyl-4-chloro-5-(1-fluoropropyl)]phenylpiperazine,
(109) 1-hydroxyethyl-4-(3-phenyl-4-methoxy-5-phenylacetyl)phenylpiperazine,
(110) 1-ethyl-4-[3-phenyl-5-(1-fluoropropyl)]phenylpiperazine,
(111) 1-ethyl-4-(3-phenyl-5-propionyl)phenylpiperazine,
(112) 1-ethyl-4-[3-(2-tolyl)-4-chloro-5-(1-fluoropropyl)]phenylpiperazine,
(113) 1-ethyl-4-[3-(2-methoxyphenyl)-4-methoxy-5-propyl]phenylpiperazine,
(114) 1-ethyl-4-(3-phenyl-4-methoxy-5-ethanesulfonyl)phenylpiperazine,
(115) 1-ethyl-4-(3-phenyl-4-methoxy-5-dimethylaminosulfonyl)phenylpiperazine,
(116) 1-ethyl-4-[3-phenyl-4-methoxy-5-(1-pyrrolidinylsulfonyl)]phenylpiperazine,
(117) 1-ethyl-4-[3-(2-tolyl)-4-chloro-5-(2,2,2-trifluoroethyl)sulfonylamino]phenylpiperazine.
(118) 1-ethyl-4-[3-(2-tolyl)-4-chloro-5-(4-fluorophenylsulfonylamino)]phenylpiperazine,
(119) 1-ethyl-4-[3-phenyl-4-chloro-5-(1-hydroxypropyl)]phenylpiperazine,
(120) 1-ethyl-4-(3-phenyl-4-chloro-5-ethanesulfonyl)phenylpiperazine,
(121) 1-ethyl-4-(3-phenyl-4-chloro-5-propionyl)phenylpiperazine,
(122) 1-ethyl-4-[3-(2-tolyl)-4-chloro-5-(1-pyrrolidylsulfonyl)]phenylpiperazine,
(123) 1-ethyl-4-{3-[2-(4-fluorotolyl)]-4-chloro-5-(1-fluoropropyl)}phenylpiperazine,
(124) 1-ethyl-4-[3-(2-methoxyphenyl)-4-chloro-5-(1-fluoropropyl)]phenylpiperazine,
(125) 1-ethyl-4-[3-(2,4-difluorophenyl)-4-chloro-5-(1-fluoropropyl)]phenylpiperazine,
(126) 1-ethyl-4-[3-(2-methoxymethylphenyl)-4-chloro-5-(1-fluoropropyl)]phenylpiperazine,
(127) 1-ethyl-4-{3-[2-(4-fluorotolyl)]-4-chloro-5-cyclopropaneaminosulfonyl}phenylpiperazine,
(128) 1-ethyl-4-[3-phenyl-4-chloro-5-(1-methylpropyl)]phenylpiperazine,
(129) 1-ethyl-4-{3-[2-(4-fluorotolyl)]-4-chloro-5-cyclopropylmethylsulfonyl}phenylpiperazine,
(130) 1-ethyl-4-(3-phenyl-4-fluoro-5-ethanesulfonyl)phenylpiperazine,
(131) 1-[3-(4-pyridyl)propyl]-4-[3-(2-tolyl)-4-chloro-5-(1-fluoropropyl)]phenylpiperazine,
(132) 1-propyl-4-[3-(2-tolyl)-4-chloro-5-(1-fluoropropyl)]phenylpiperazine,
(133) 1-ethyl-4-[3-(2-hydroxymethylphenyl)-4-chloro-5-(1-fluoropropyl)]phenylpiperazine,
(134) 1-ethyl-4-[3-(2-tolyl)-4-chloro-5-propanesulfonylamino]phenylpiperazine,
(135) 1-ethyl-4-[3-(2-tolyl)-4-chloro-5-dimethylaminosulfonyl]phenylpiperazine,
(136) 1-ethyl-4-[3-(2-tolyl)-4-fluoro-5-methanesulfonyl]phenylpiperazine,
(137) 1-ethyl-4-[3-(2-chloro-4-fluorophenyl)-4-chloro-5-(1-fluoropropyl)]phenylpiperazine,
(138) 1-ethyl-4-[3-(2-tolyl)-4-chloro-5-(1-ethylpropyl)]phenylpiperazine,
(139) 1-ethyl-4-[3-(2-tolyl)-4-chloro-5-methanesulfonyl]phenylpiperazine,
(140) 1-ethyl-4-[3-(2-tolyl)-4-chloro-5-propanesulfonyl]phenylpiperazine,
(141) 1-ethyl-4-[3-(2-tolyl)-4-chloro-5-(1-fluoro-4-pentenyl)]phenylpiperazine,
(142) 1-ethyl-4-[3-(2-tolyl)-4-chloro-5-propylaminosulfonyl]phenylpiperazine,
(143) 1-ethyl-4-[3-(2-tolyl)-4-chloro-5-ethanesulfonylamino]phenylpiperazine,
(144) 1-ethyl-4-[3-(2-chlorophenyl)-4-chloro-5-(2,2,2-trifluoroethyl)sulfonylamino]phenylpiperazine,
(145) 1-ethyl-4-[3-(2-tolyl)-4-cyano-5-(1-fluoropropyl)]phenylpiperazine,
(146) 1-ethyl-4-[3-(2-tolyl)-4-chloro-5-(3-chloropropyl)sulfonylamino]phenylpiperazine,
(147) 1-ethyl-4-[3-(2-tolyl)-4-chloro-5-phenylaminosulfonyl]phenylpiperazine,
(148) 1-ethyl-4-[3-(2-tolyl)-4-chloro-5-benzyloxymethyl]phenylpiperazine,
(149) 1-ethyl-4-[3-(2-tolyl)-4-chloro-5-propoxymethyl]phenylpiperazine,
(150) 1-ethyl-4-[3-(2-tolyl)-4-chloro-5-(4-pyridyl)methoxymethyl]phenylpiperazine,
(151) 1-ethyl-4-(3-phenyl-4-methoxy-5-propanesulfonyl)phenylpiperazine,
(152) 1-ethyl-4-(3-phenyl-4-methoxy-5-butanesulfonyl)phenylpiperazine,
(153) 1-ethyl-4-[3-phenyl-4-methoxy-5-(2-fluoroethane)sulfonyl]phenylpiperazine,
(154) 1-ethyl-4-[3-(2-tolyl)-4-chloro-5-ethoxymethyl]phenylpiperazine,
(155) 1-methyl-4-[3-(2-tolyl)-4-chloro-5-(1-hydroxybutyl)]phenylpiperazine,
(156) 1-ethyl-4-[3-(2-tolyl)-4-chloro-5-allyloxymethyl]phenylpiperazine,
(157) 1-ethyl-4-[3-(2-tolyl)-4-chloro-5-cyclopropylmethoxymethyl]phenylpiperazine,
(158) 1-ethyl-4-[3-(2-tolyl)-4-chloro-5-(1-pyrrolidinyl)]phenylpiperazine,
(159) 1-methyl-4-[3-(2-chlorophenyl)-4-chloro-5-(1-fluorobutyl)]phenylpiperazine,
(160) 1-methyl-4-[3-(2-chlorophenyl)-4-chloro-5-benzylsulfonylamino]phenylpiperazine,
(161) 1-methyl-4-[3-(2-chlorophenyl)-4-chloro-5-propanesulfonyl]phenylpiperazine,
(162) 1-ethyl-4-{3-phenyl-4-methoxy-5-[3-(4-fluorophenoxy)propane]sulfonyl}phenylpiperazine,
(163) 1-methyl-4-[3-(2-chlorophenyl)-4-chloro-5-isopropylsulfonylamino]phenylpiperazine,
(164) 1-ethyl-4-[3-phenyl-4-methoxy-5-(2-cyanoethylsulfonyl)]phenylpiperazine,
(165) 1-ethyl-4-(3-phenyl-4-chloro-5-propanesulfonylamino)phenylpiperazine,
(166) 1-ethyl-4-[3-(2-tolyl)-4-chloro-5-difluoromethyl]phenylpiperazine,
(167) 1-ethyl-4-[3-phenyl-4-methoxy-5-(1,1-difluoropropyl)]phenylpiperazine,
(168) 1-ethyl-4-[3-(4-methoxyphenyl)-4-chloro-5-propanesulfonylamino]phenylpiperazine,
(169) 1-methyl-4-[3-(2-chlorophenyl)-4-chloro-5-methanesulfonylamino]phenylpiperazine,
(170) 1-ethyl-4-[3-(2,4-dichlorophenyl)-4-chloro-5-propanesulfonylamino]phenylpiperazine, (171) 1-ethyl-4-[3-(2-tolyl)-4-chloro-5-propanedithio]phenylpiperazine,
(172) 1-ethyl-4-[3-phenyl-4-chloro-5-(1,3-dithian-2-yl)]phenylpiperazine,
(173) 1-ethyl-4-[3-(2-tolyl)-4-chloro-5-propanesulfonylaminomethyl]phenylpiperazine,
(174) 1-methyl-4-[3-(4-fluorophenyl)-4-methoxy-5-propanesulfonyl]phenylpiperazine,
(175) 1-ethyl-4-[3-(2-ethylphenyl)-4-chloro-5-propanesulfonylamino]phenylpiperazine,
(176) 1-hydroxyethyl-4-[3-(4-fluorophenyl)-4-methoxy-5-ethanesulfonyl]phenylpiperazine,
(177) 1-ethyl-4-[3-(2-formylphenyl)-4-chloro-5-propanesulfonylamino]phenylpiperazine,
(178) 1-ethyl-4-[3-(2-cyanophenyl)-4-chloro-5-propanesulfonylamino]phenylpiperazine,
(179) 1-(2-pyridylethyl)-4-[3-(4-fluorophenyl)-4-methoxy-5-ethanesulfonyl]phenylpiperazine,
(180) 1-(2-pyridylmethyl)-4-[3-(4-fluorophenyl)-4-methoxy-5-ethanesulfonyl]phenylpiperazine,
(181) 1-(3-pyridylmethyl)-4-[3-(4-fluorophenyl)-4-methoxy-5-ethanesulfonyl]phenylpiperazine,
(182) 1-(4-pyridylethyl)-4-[3-(4-fluorophenyl)-4-methoxy-5-ethanesulfonyl]phenylpiperazine,
(183) 1-[3-(4-fluorophenyl)-4-methoxy-5-ethanesulfonyl]phenylpiperazine,
(184) 1-(2-fluoroethyl)-4-[3-(4-fluorophenyl)-4-methoxy-5-ethanesulfonyl]phenylpiperazine,
(185) 1-ethyl-4-[3-(2-chlorophenyl)-4-chloro-5-(1-propenyl)]phenylpiperazine,
(186) 1-ethyl-4-[3-(2-chlorophenyl)-4-chloro-5-(1-chloropropyl)]phenylpiperazine,
(187) 1-methyl-4-[3-phenyl-4-chloro-5-(1-fluoropropyl)]phenylpiperazine,
(188) 1-methyl-4-[3-(2-hydroxymethylphenyl)-4-chloro-5-(1-fluoropropyl)]phenylpiperazine,
(189) 1-ethyl-4-[3-(2-fluoromethylphenyl)-4-chloro-5-(1-fluoropropyl)]phenylpiperazine,
(190) 1-methyl-4-{3-(2-fluoromethylphenyl)-4-chloro-5-[1-fluoropropyl]}phenylpiperazine,
(191) 1-ethyl-4-{3-[2-(4-fluorotolyl)]-4-chloro-5-[1-fluoropropyl]}phenylpiperazine,
(192) 1-[2-(2-pyridyl)ethyl]-4-[3-(2-tolyl)-4-chloro-5-(1-fluoropropyl)]phenylpiperazine,
(193) 1-[2-(2-pyridyl)ethyl]-4-[3-(2-cyanophenyl)-4-chloro-5-(1-fluoropropyl)]phenylpiperazine,
(194) 1-ethyl-4-[3-(2,6-xylyl)-4-chloro-5-(1-fluoropropyl)]phenylpiperazine,
(195) 1-ethyl-4-{3-(2-trifluoromethylphenyl)-4-chloro-5-[1-fluoropropyl]}phenylpiperazine,
(196) 1-ethyl-4-[3-(2-ethylphenyl)-4-chloro-5-(1-fluoropropyl)]phenylpiperazine,
(197) 1-(2-hydroxyethyl)-4-[3-(2-ethylphenyl)-4-chloro-5-(1-fluoropropyl)]phenylpiperazine,
(198) 1-(2-hydroxyethyl)-4-{3-(2-trifluoromethylphenyl)-4-chloro-5-[1-fluoropropyl]}phenylpiperazine,
(199) 1-methyl-4-{3-(2-tolyl)-4-chloro-5-[1-fluoropropyl]}phenylpiperazine, and
(200) 1-(2-hydroxyethyl)-4-{3-[2-(4-fluorotolyl)]-4-chloro-5-[1-fluoropropyl]}phenylpiperazine.

The biphenyl derivative represented by the formula (I) or (II) according to the present invention can be prepared by the following processes, though the processes for the preparation of the derivative are not limited to them.

(1) biphenyl derivatives represented by the formula (I) or (II) wherein $R^1$ is a halogenated lower alkyl group, $R^3$ is a cyano group, $R^5$ is a hydroxy lower alkyl group, and n is 0

A phenylpiperazine derivative (III) is protected to form a protected phenylpiperazine derivative (IV); the derivative (IV) is reacted with an alkylmagnesium halide to form a protected hydroxyalkylphenylpiperazine derivative (V); the derivative (V) is reacted with a halogenating agent such as hexafluoropropene diethylamine, diethylaminosulfur trifluoride (hereinafter abbreviated to "DAST"), thionyl chloride and sulfuryl chloride to form a protected halogenated alkylphenylpiperazine derivative (VI); the derivative (VI) is reacted with 2-(1,3,2-dioxaborinan-2-yl)benzaldehyde in the presence of tetrakis(triphenylphosphine)palladium (0) and cesium carbonate to form a protected halogenated alkylbiphenylpiperazine derivative (VII); the derivative (VII) is reacted with hydroxyamine to form a protected halogenated alkyl oxime biphenylpiperazine derivative (VIII); the derivative (VIII) is reacted with acetic anhydride in the presence of pyridine and 4-dimethylaminopyridine to form a protected halogenated alkylcyanobiphenylpiperazine derivative (IX); the derivative (IX) is treated with an acid to form a halogenated alkylcyanobiphenylpiperazine derivative (X); and the derivative (X) is reacted with a halogenated alkanol.

The protected hydroxyalkylphenylpiperazine derivative (V) and the compounds subsequent thereto may each have an asymmetric carbon atom in its molecule, and the objective compound can be prepared as an optically active substance either by optical resolution of the corresponding compound or by asymmetric synthesis, if necessary. In the optical resolution, optically active cis-2-benzamidocyclohexane carboxylic acid (hereinafter abbreviated to "cis acid"), optically active dibenzoyl tartaric acid (hereinafter abbreviated to "DBTA"), di-p-toluoyl tartaric acid (hereinafter abbreviated to "DTTA") and the like may be used as a reagent for optical resolution.

This process is illustrated by the following reaction scheme:

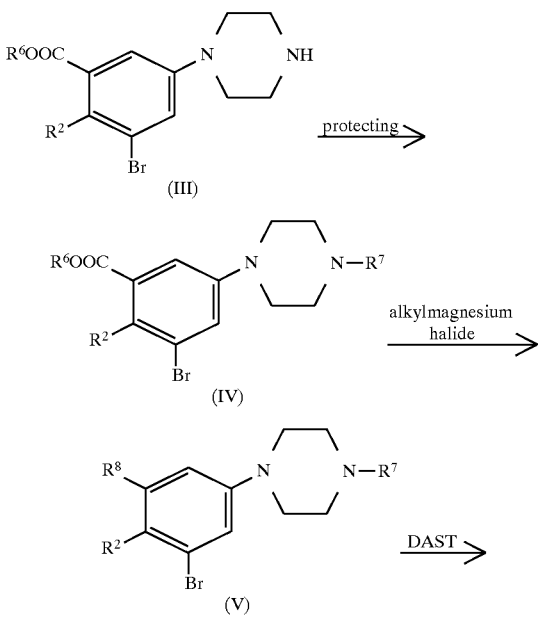

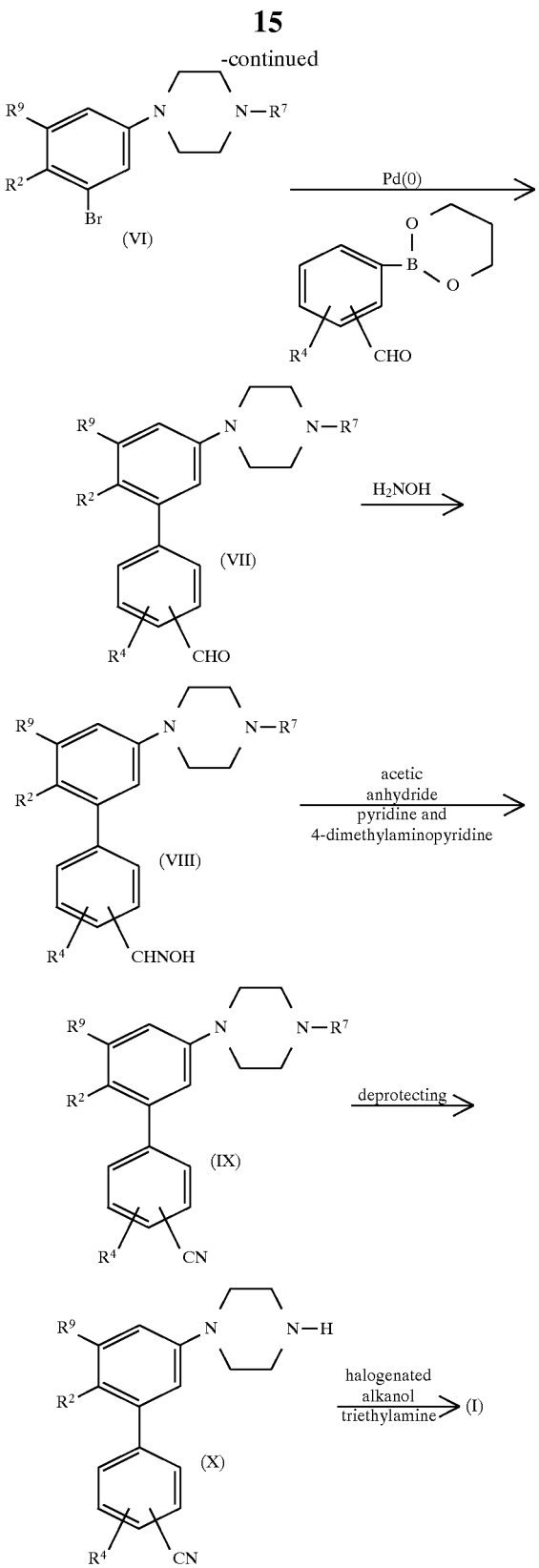

wherein $R^2$, $R^4$, $R^6$, $R^7$, $R^8$ and $R^9$ are each as defined above.
(2) biphenyl derivatives represented by the formula (I) or (II) wherein $R^1$ is a halogenated lower alkyl group; $R^3$ is one of various groups including cyano group; $R^5$ is one of various groups including hydroxy lower alkyl group; and n is 0

Such biphenyl derivatives can be prepared by one of the following three processes:

(i) a nitrobenzoic acid ester derivative (XIV) is hydrolyzed and the resulting product is reacted with a chlorinating agent such as oxalyl chloride to form a nitrobenzoyl chloride derivative (XV); this derivative (XV) is reacted with an alkylmalonic acid ester in the presence of a base to form a malonic acid ester derivative (XVI); this derivative (XVI) is treated with an acid or a base to form an acylnitrobenzene derivative (XVII); this derivative (XVII) is reduced with sodium borohydride, diisopinocanephenylboron B-chloride (Dip-chloride) or the like; the resulting product is reacted with a halogenating agent to form a halogenated alkylnitrobenzene derivative (XVIII): this derivative (XVIII) is reduced into a halogenated alkylaniline derivative (XIX); this derivative (XIX) is reacted with bis(2-chloroethyl)amine to form a halogenated alkylphenylpiperazine derivative (XX); this derivative (XX) is reacted with a 2-(1,3,2-dioxaborinan-2-yl) benzene derivative or the like in the presence of triphenylphosphinepalladium [Pd(PPh$_3$)$_4$] and tripotassium phosphate to form a biphenylpiperazine derivative (XXI); and this derivative (XXI) is reacted with a halogenated alkanol or the like.

The halogenated alkylnitrobenzene derivative (XVIII) and the compounds subsequent thereto may each have an asymmetric carbon atom in its molecule, and the objective compound can be prepared as an optically active substance either by optical resolution of the corresponding compound or by asymmetric synthesis, if necessary.

(ii) a phenylpiperazine derivative (III) derived from a nitrobenzoic acid ester derivative (XIV) is protected to form a protected piperazylbenzoic acid derivative (XXII); this derivative (XXII) is reacted with 2-mercaptopyridine or the like to form an active ester; this ester is reacted with a Grignard reagent such as alkylmagnesium bromide to form a protected acylphenylpiperazine derivative (XXIII); this derivative (XXIII) is reduced with sodium borohydride or the like to form a protected hydroxyalkylphenylpiperazine derivative (V); this derivative (V) is reacted with a halogenating agent to form a protected halogenated alkylphenylpiperazine derivative (VI); this derivative (VI) is deprotected to form a halogenated alkylphenylpiperazine derivative (XX); and this derivative (XX) is treated in a similar manner to that of the process (i).

The protected hydroxyalkylphenylpiperazine derivative (V) and the compounds subsequent thereto may each have an asymmetric carbon atom in its molecule, and the objective compound can be prepared as an optically active substance either by optical resolution of the corresponding compound or by asymmetric synthesis, if necessary.

(iii) a dibromoaniline derivative (XXIV) is reacted with bis(2-chloroethyl)amine to form a dibromophenylpiperazine derivative (XXV); this derivative (XXV) is protected to form a protected dibromophenylpiperazine derivative (XXVI); this derivative (XXVI) is converted into a protected hydroxyalkylphenylpiperazine derivative (V) either by reacting the derivative (XXVI) with a base and an acid anhydride to form a protected acylphenylpiperazine derivative (XXIII) and converting the derivative (XXIII) into the derivative (V) or by reacting the derivative (XXVI) with a base and a lower aliphatic aldehyde; and this derivative (V) is treated in a similar manner to that of the process (ii).

These processes (i) to (iii) can be illustrated by the following reaction scheme:
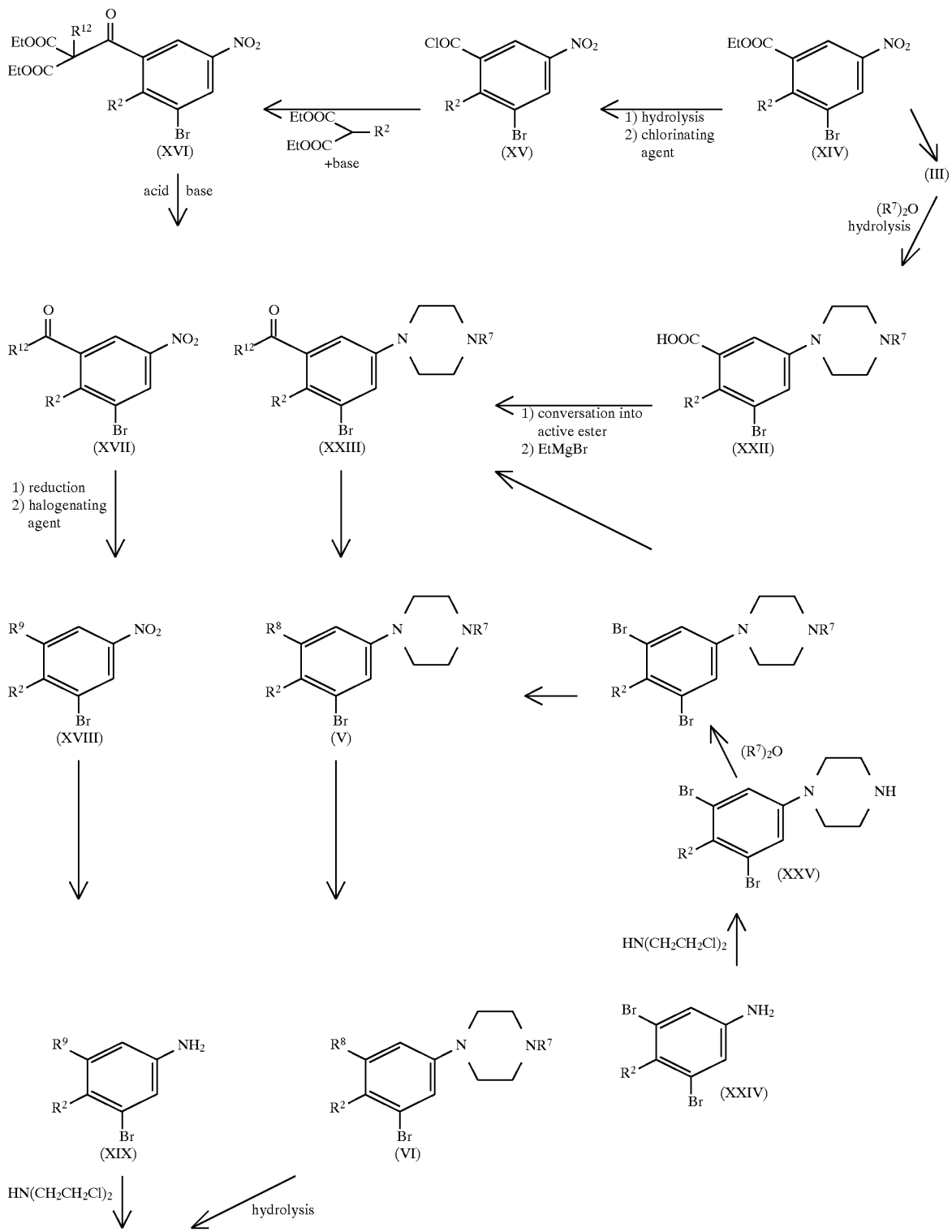

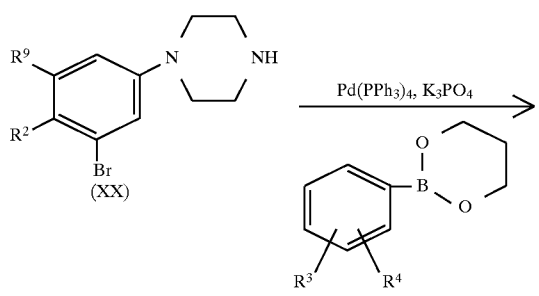
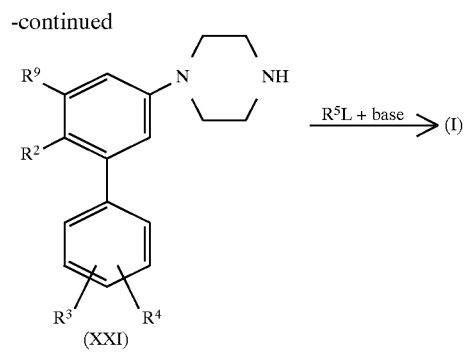

wherein $R^2$, $R^3$, $R^4$, $R^7$ and $R^9$ are each as defined above; $R^{12}$ represents a lower alkyl group; L represents a leaving group; and Ph represents a phenyl group.

(3) biphenyl derivatives represented by the formula (I) or (II) wherein $R^1$ is a lower alkylsulfonylamino group, $R^3$ and $R^4$ are the same or different from each other and each is a lower alkyl group or the like; and n is 0

A phenylpiperazine derivative (III) is reacted with an alkyl halide to form a phenylalkylpiperazine derivative (XI); the derivative (XI) is reacted with tolylboric acid in the presence of palladium acetate to form a biphenylalkylpiperazine derivative (XII); the derivative (XII) is hydrolyzed; the product of this hydrolysis is reacted with ethyl chlorocarbonate in the presence of triethylamine; the resulting product is reacted with sodium azide and a base successively to form an aminobiphenylalkylpiperazine derivative (XIII); and the derivative (XIII) is reacted with an alkylsulfonyl halide.

This process is illustrated by the following reaction scheme:

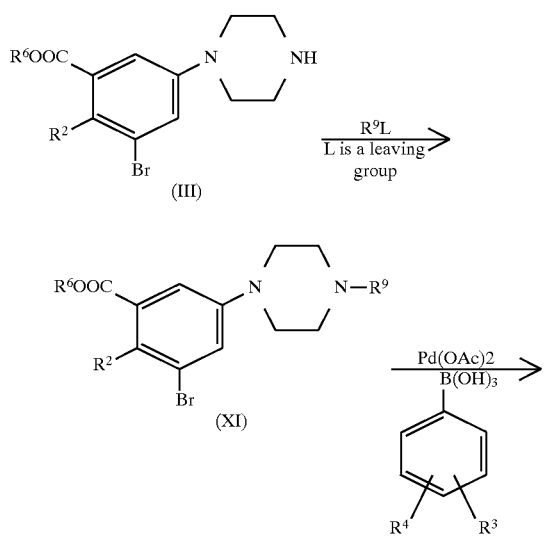

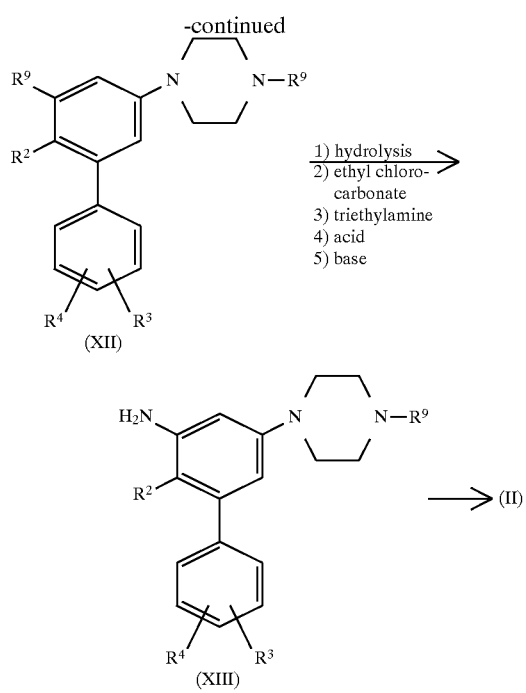

wherein $R^2$, $R^3$, $R^4$, $R^6$ and $R^9$ are each as defined above.

The biphenyl derivatives of the present invention can be prepared from, e.g., known 2-phenyl-[1,3,2]-dioxaborinane derivatives and known phenylboric acid derivatives of which specific examples will be described below according to one of the production processes described above.

The following 2-phenyl-[1,3,2]-dioxaborinane derivatives and phenylboric acid derivatives can also be prepared according to known synthetic processes. Specific examples of 2-phenyl-[1,3,2]-dioxaborinane derivatives (those described in the brackets are CAS registry numbers)

(1) 2-phenyl-[1,3,2]-dioxaborinane [4406-7-3],
(2) 2-(4-fluorophenyl)-[1,3,2]-dioxaborinane [156942-21-1],
(3) 2-(4-bromophenyl)-[1,3,2]-dioxaborinane [54947-91-0],
(4) 2-(4-methoxyphenyl)-[1,3,2]-dioxaborinane [155826-85-0],
(5) 2-(4-cyanophenyl)-[1,3,2]-dioxaborinane [152846-62-3],
(6) 2-(2-methoxyphenyl)-[1,3,2]-dioxaborinane [141522-26-1], and
(7) 2-(2,4-dichlorophenyl)-[1,3,2]-dioxaborinane [73852-21-8].

Specific examples of phenylboric acid derivatives (those described in the brackets are CAS registry numbers)

(1) phenylboric acid [98-80-6],
(2) 2-fluorophenylboric acid [1993-03-9],
(3) 3-fluorophenylboric acid [768-35-4],
(4) 4-fluorophenylboric acid [1765-93-1],
(5) 2-chlorophenylboric acid [3900-89-8],
(6) 3-chlorophenylboric acid [63503-60-6],
(7) 4-chlorophenylboric acid [1679-18-1],
(8) 3-bromophenylboric acid [89598-96-9],
(9) 4-bromophenylboric acid [5467-74-3 or 130869-99-7],
(10) 4-iodophenylboric acid [5122-99-6],
(11) 2-cyanophenylboric acid [138642-62-3],
(12) 3-cyanophenylboric acid [150255-96-2],
(13) 4-cyanophenylboric acid [126747-14-6],
(14) 2-trifluoromethylphenylboric acid [1423-27-4],
(15) 3-trifluoromethylphenylboric acid [1423-26-3],
(16) 4-trifluoromethylphenylboric acid [128796-39-4],
(17) 2-ethylphenylboric acid [90002-36-1],
(18) 3-ethylphenylboric acid [90555-65-0],
(19) 4-ethylphenylboric acid [63139-21-9],
(20) 2-formylphenylboric acid [40138-16-7],
(21) 3-formylphenylboric acid [87199-16-4],
(22) 4-formylphenylboric acid [87199-17-5],
(23) 2-hydroxyphenylboric acid [87199-14-2],
(24) 3-hydroxyphenylboric acid [87199-15-3],
(25) 4-hydroxyphenylboric acid [59106-93-2],
(26) 2-methoxyphenylboric acid [5720-06-9],
(27) 3-methoxyphenylboric acid [10365-98-7],
(28) 4-methoxyphenylboric acid [5720-07-0],
(29) 2,4-dichlorophenylboric acid [68716-47-2],
(30) 2,3-difluorophenylboric acid [121219-16-7],
(31) 2,3,4-trimethoxyphenylboric acid [118062-05-8],
(32) 2-fluoro-3-trifluoromethylphenylboric acid [157834-21-4],
(33) 3,4-dichlorophenylboric acid [151169-75-4],
(34) 2,3-dichlorophenylboric acid [151169-74-3],
(35) 3-trifluoromethyl-4-methoxyphenylboric acid [149507-36-8],
(36) 3-fluoromethyl-4-methoxyphenylboric acid [149507-26-6],
(37) 3-chloro-4-fluorophenylboric acid [144432-85-9],
(38) 3-fluoro-4-chlorophenylboric acid [137504-86-0],
(39) 2,4-difluorophenylboric acid [144025-03-6],
(40) 2,4-di(trifluoromethyl)phenylboric acid [153254-09-2],
(41) 3-methoxy-4-chlorophenylboric acid [89694-47-3],
(42) 2,4-dimethoxyphenylboric acid [133730-34-4],
(43) 3,4-dimethoxyphenylboric acid [122775-35-3],
(44) 2,3-dimethoxyphenylboric acid [40972-86-9],
(45) 2-formyl-4-methoxyphenylboric acid [139962-95-1], and
(46) 3-formyl-4-methoxyphenylboric acid [121124-97-8].

Although the biphenyl derivative according to the present invention may be present as a stereoisomer, the present invention is not limited in this respect, but the derivative may be any of the stereoisomers thereof or a mixture of them. Further, the biphenyl derivative according to the present invention may be any of the geometrical isomers thereof or a mixture of them.

The pharmacologically acceptable salt of the biphenyl derivative according to the present invention includes inorganic acid addition salts such as hydrochloride, sulfate, nitrate, hydrobromide, hydroiodide, perchlorate and phosphate; organic acid addition salts such as oxalate, maleate, fumarate and succinate; sulfonic acid addition salts such as methanesulfonate, ethanesulfonate, benzenesulfonate, p-toluenesulfonate and camphorsulfonate; and amino acid addition salts.

The present invention also relates to the phenypiperazine derivative represented by the above formula (XXVII) or salt thereof. The kind of the salt is not limited. The phenylpiperazine derivative represented by the formula (XXVII) is novel and is useful as an intermediate for the preparation of the biphenyl derivative represented by the formula (I) or (II) according to the present invention.

Specific examples of the phenylpiperazine derivative represented by the formula (XXVII) include the following compounds, though the derivative (XXVII) is not limited to them:

(1) 1-[3-bromo-4-chloro-5-(1-hydroxyethyl)]phenylpiperazine,
(2) 1-[3-bromo-4-chloro-5-(1-hydroxypropyl)]phenylpiperazine,
(3) 1-[3-bromo-4-chloro-5-(1-hydroxybutyl)]phenylpiperazine,
(4) 1-[3-bromo-4-chloro-5-(1-hydroxypentyl)]phenylpiperazine,
(5) 1-[3-bromo-4-chloro-5-(1-hydroxyhexyl)]phenylpiperazine,
(6) 1-hydroxymethyl-4-[3-bromo-4-chloro-5-(1-fluoropropyl)]phenylpiperazine,
(7) 1-hydroxyethyl-4-[3-bromo-4-chloro-5-(1-fluoropropyl)]phenylpiperazine,
(8) 1-hydroxypropyl-4-[3-bromo-4-chloro-5-(1-fluoropropyl)]phenylpiperazine,
(9) 1-hydroxybutyl-4-[3-bromo-4-chloro-5-(1-fluoropropyl)]phenylpiperazine,
(10) 1-hydroxypentyl-4-[3-bromo-4-chloro-5-(1-fluoropropyl)]phenylpiperazine,
(11) 1-hydroxyhexyl-4-[3-bromo-4-chloro-5-(1-fluoropropyl)]phenylpiperazine,
(12) 1-hydroxyethyl-4-[3-bromo-4-chloro-5-(1-chloropropyl)]phenylpiperazine,
(13) 1-hydroxyethyl-4-[3-bromo-4-chloro-5-(1-bromopropyl)]phenylpiperazine,
(14) 1-hydroxyethyl-4-[3-bromo-4-chloro-5-(1-iodopropyl)]phenylpiperazine,
(15) 1-(t-butoxy)carbonyl-4-[3-bromo-4-chloro-5-(1-fluoropropyl)]phenylpiperazine,
(16) 1-ethoxycarbonyl-4-[3-bromo-4-chloro-5-(1-fluoropropyl)]phenylpiperazine,
(17) 1-benzyloxycarbonyl-4-[3-bromo-4-chloro-5-(1-fluoropropyl)]phenylpiperazine,
(18) 1-formyl-4-[3-bromo-4-chloro-5-(1-fluoropropyl)]phenylpiperazine,
(19) 1-acetoxy-4-[3-bromo-4-chloro-5-(1-fluoropropyl)]phenylpiperazine,
(20) 1-benzyl-4-[3-bromo-4-chloro-5-(1-fluoropropyl)]phenylpiperazine,
(21) 1-(2-trimethylsilyloxyethyl)-4-[3-bromo-4-chloro-5-(1-hydroxypropyl)]phenylpiperazine,
(22) 1-(2-trimethylsilyloxyethyl)-4-[3-bromo-4-chloro-5-(1-fluoropropyl)]phenylpiperazine,
(23) 1-(2-trimethylsilyloxyethyl)-4-[3-bromo-4-chloro-5-(1-chloroxypropyl)]phenylpiperazine,
(24) 1-(2-trimethylsilyloxyethyl)-4-[3-bromo-4-chloro-5-(1-bromopropyl)]phenylpiperazine,
(25) 1-(2-trimethylsilyloxyethyl)-4-[3-bromo-4-chloro-5-(1-iodopropyl)]phenylpiperazine,
(26) 1-(3,5-dibromo-4-chloro)phenylpiperazine,
(27) 1-(t-butoxycarbonyl)-4-(3,5-dibromo-4-methoxy)phenylpiperazine,
(28) 1-(t-butoxycarbonyl)-4-(3,5-dibromo-4-chloro)phenylpiperazine,
(29) 1-methyl-4-[3-(2-tolyl)-4-chloro-5-ethanesulfonylamino]phenylpiperazine,
(30) 1-(3-bromo-4-chloro-5-ethoxycarbonyl)phenylpiperazine,

(31) 1-(t-butoxycarbonyl)-4-(3-bromo-4-chloro-5-ethoxycarbonyl)phenylpiperazine,
(32) 1-ethyl-4-(3-bromo-4-chloro-5-ethoxycarbonyl)phenylpiperazine,
(33) 1-[3-bromo-4-chloro-5-(1-propenyl)]phenylpiperazine,
(34) 1-(t-butoxycarbonyl)-4-(3-bromo-4-chloro-5-carboxy)phenylpiperazine,
(35) 1-(t-butoxycarbonyl)-4-[3-bromo-4-chloro-5-(2-pyridylthio)carbonyl]phenylpiperazine, and
(36) 1-(t-butoxycarbonyl)-4-(3-bromo-4-chloro-5-propionyl)phenylpiperazine.

The compound of the present invention exhibits an extremely high $LD_{50}$ value and extremely high safeness.

The biphenyl derivative or the pharmacologically acceptable salt thereof according to the present invention may be used as an active ingredient of a therapeutic and ameliorative agent for a mental disorder. Examples of the mental disorder include cerebrovascular disorder, aggressive behavior due to senile dementia, mental excitation, poriomania, delirium, hallucination, hyperkinesia, schizophrenia, emotional disturbance, depression, neurosis, psychophysiologic disorder and anxiety neurosis. In other words, the diseases against which the biphenyl derivative or the pharmacologically acceptable salt thereof according to the present invention may be clinically applicable are those against which dopamine 2 receptor antagonism and/or serotonin 2 receptor antagonism is efficacious.

The dosage form of the compound of the present invention include preparations for oral administration such as powder, fine granule, granule, tablet, coated tablet and capsule; external preparations such as ointment, plaster and suppository; and injection. That is, a pharmacological composition of the present invention comprises a therapeutically or amelioratively effective amount of the biphenyl derivative or the pharmacologically acceptable salt thereof described above and a pharmacologically acceptable vehicle.

These preparations can be each prepared by the use of a conventional vehicle, filler or carrier according to a conventional method. A preparation for oral administration according to the present invention is prepared by adding a vehicle or filler and, if necessary, a binder, disintegrator, lubricant, color and/or corrigent to the biphenyl derivative or the pharmaceutically acceptable salt thereof and shaping the obtained mixture into a powder, fine granule, granule, tablet, coated tablet, capsule or the like.

Examples of the vehicle or filler include lactose, corn starch, sucrose, glucose, mannitol, sorbitol, crystalline cellulose and silicon dioxide; those of the binder include polyvinyl alcohol, polyvinyl ether, methylcellulose, ethylcellulose, acacia, tragacanth, gelatin, shellac, hydroxypropylmethylcellulose, hydroxypropylcellulose, polyvinylpyrrolidone, polypropylene glycol-polyoxyethylene block copolymer and meglumine; those of the disintegrator include starch, agar, gelatin powder, crystalline cellulose, calcium carbonate, sodium hydrogen carbonate, calcium citrate, dextrin, pectin and calcium carboxymethylcellulose; those of the lubricant include magnesium stearate, talc, polyethylene glycol, silica and hardened vegetable oils; those of the color include those authorized as pharmaceutical additives; and those of the corrigent include cocoa powder, menthol, aromatic powder, mentha oil, borneol and powdered cinnamon bark. Of course, the tablet and granule may be suitably coated with sugar or the like, if necessary.

An injection according to the present invention is prepared by adding a pH modifier, solubilizing agent, isotonicity agent and, if necessary, an auxiliary solubilizer and/or stabilizer to the biphenyl derivative or the pharmaceutically acceptable salt thereof, and formulating the obtained mixture in a conventional manner.

The method for preparing an external preparation according to the present invention is not limited, but may be any ordinary one. The base material to be used in this preparation includes various materials conventionally used in the preparation of drugs, quasi drugs, cosmetics and so on.

Specific examples of the base material to be used in the external preparation include animal and vegetable oils, mineral oils, ester oils, waxes, higher alcohols, fatty acids, silicone oils, surfactants, phospholipids, alcohols, polyhydric alcohols, water-soluble polymers, clay minerals and purified water, and examples of the material to be optionally used at need include pH modifiers, antioxidants, chelating agents, antiseptics, antifungal substances, coloring matters and fragrances, though the material is not limited to them. The external preparation may further contain a differentiation-inducing agent, a blood flow accelerator, a disinfectant, an antiphlogistic, a cell activator, a vitamin, an amino acid, a humectant and/or a keratolytic. The above base materials are each used in such an amount as to give a concentration ordinarily predetermined in the preparation of an external preparation.

The dose of the biphenyl derivative or the pharmacologically acceptable salt thereof according to the present invention varies depending upon symptom and degree thereof, age, complication and so on, and therefore cannot be limited. Further, the dose varies also depending upon the kind of the salt or route of administration. The dose per adult a day is generally 0.01 to 1000 mg, preferably 0.1 to 500 mg, still more preferably 0.5 to 100 mg, which is administered orally, intravenously, as a suppository or transcutaneously.

The preparation processes of a 2-phenyl-[1,3,2]-dioxaborinane derivative and a phenylboric acid derivative which are necessary for carrying out the present invention will now be described specifically as Preparative Examples. Other derivatives can also be prepared in manners similar thereto.

PREPARATIVE EXAMPLES

Preparative Example 1

Synthesis of 2-cyanophenylboric acid

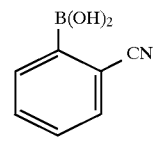

12.4 ml of a 1.6M solution of t-butyllithium in n-pentane was dropwise added to 23 ml of THF at −76° C. in about 10 minutes. Then, a solution of 2.0 g (11.0 mmol) of 2-bromobenzonitrile in 3.0 ml of THF was dropwise added to the resulting mixture at −76° C. in about 20 minutes, followed by the dropwise addition of 2.3 ml (19.8 mmol) of trimethoxyborane in 7 minutes. The obtained mixture was stirred at −76° C. for 20 minutes, followed by the addition of 13.8 ml of 2N hydrochloric acid. The obtained mixture was stirred at room temperature for 30 minutes and extracted with ethyl acetate. The ethyl acetate phase was washed with water and a saturated brine, dried and distilled to remove the solvent. 15 ml of methylene chloride and 15 ml of n-hexane were added to the obtained residue. The obtained mixture was stirred at room temperature for 30 minutes to give a precipitate. The precipitate was recovered by filtration and dried to give 0.9 g of the title compound (yield: 55.7%).

m.p.; 237°–240° C.

$^1$H-NMR(400 MHz, CDCl$_3$); δ(ppm) 7.5–8.1(5H, m), 8.77(1H, m).

$^1$H-NMR(400 MHz, CDCl$_3$+D$_2$O); δ(ppm) 7.56(1H, dd, J=6.2, 7.3 Hz), 7.64(1H, dd, J=6.2, 7.3 Hz), 7.71(1H, d, J=7.3 Hz), 8.05(1H, dd, J=7.3 Hz).

IR(cm$^{-1}$, nujol): 2200

Preparative Example 2

Synthesis of 2-(1,3,2-dioxaborinan-2-yl)benzonitrile

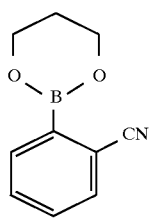

543 mg (3.7 mmol) of 2-cyanophenylboric acid was added to a solution of 280 mg (3.7 mmol) of 1,3-propanediol in 5.4 ml of methylene chloride. The obtained mixture was stirred at room temperature for 1.5 hours, followed by the removal of formed water. The obtained mixture was distilled to remove the solvent under reduced pressure to give 0.7 g of the title compound (yield: 100%).

m.p.; 45°–48° C.

$^1$H-NMR(400 MHz, CDCl$_3$); δ(ppm) 2.11(2H, m), 4.23 (4H, d, J=5.5 Hz), 7.48(1H, dd, J=7.6, 7.6 Hz), 7.54(1H, dd, J=7.6, 7.6 Hz), 7.68(1H, d, J=7.6 Hz), 7.87(1H, dd, J=7.6 Hz).

MS m/z: 188[MH]$^+$.

Examples will now be given to illustrate the present invention specifically, though it is needless to say that the present invention is not limited to only them.

EXAMPLES

Example 1

Synthesis of ethyl 5-nitrosalicylate

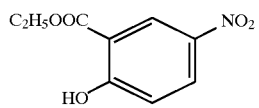

1.5 kg (8.2 mol) of 5-nitrosalicylic acid was dissolved in 2000 ml of triethyl orthoformate. The obtained solution was refluxed under heating for 3 hours to remove formed ethanol by distillation. The reaction mixture was cooled and then concentrated under reduced pressure. The obtained residue was crystallized from isopropyl ether to give 1.74 kg of the title compound as a colorless crystal.

m.p.; 85° C.

$^1$H-NMR(400 MHz, CDCl$_3$); δ(ppm) 11.5(1H, s), 8.9(1H, d), 8.3(1H, d-d), 7.1(1H, d), 4.5(2H, q), 1.5(3H, t).

Example 2

Synthesis of ethyl 3-bromo-5-nitrosalicylate

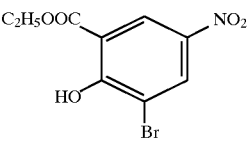

1.74 kg (8.2 mol) of ethyl 5-nitrosalicylate and 700 g of potassium acetate were dissolved in 5000 ml of acetic acid. 1.312 kg of bromine was dropwise added to the obtained solution at room temperature in one hour. Thereafter, the resulting mixture was further stirred for one hour and then concentrated under reduced pressure. The obtained residue was dissolved in ethyl acetate. The obtained solution was washed with water, dehydrated and concentrated under reduced pressure. The obtained residue was crystallized from isopropyl ether to give 2.38 kg of the title compound as a colorless crystal.

m.p.; 108° C.

$^1$H-NMR(400 MHz, CDCl$_3$); δ(ppm) 12.3(1H, s), 8.9(1H, d), 8.6(1H, d), 4.5(2H, q), 1.5(3H, t).

Example 3

Synthesis of ethyl 2-chloro-3-bromo-5-nitrobenzoate

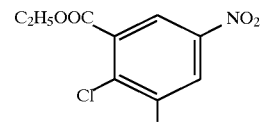

2.38 kg (8.2 mol) of ethyl 3-bromo-5-nitrosalicylate was dissolved in 3000 ml of DMF, followed by the dropwise addition of 1.26 kg of phosphorus oxychloride at room temperature. The obtained mixture was heated to 90° C. and then maintained at that temperature under heating for 10 hours. The obtained mixture was cooled and then concentrated under reduced pressure. The obtained residue was dissolved in ethyl acetate and the obtained solution was washed with water, dehydrated and concentrated under reduced pressure to give 2.25 kg of the title compound as a colorless oil.

$^1$H-NMR(400 MHz, CDCl$_3$); δ(ppm) 8.6(1H, d), 8.5(1H, d), 4.5(2H, q), 1.4(3H, t).

Example 4

Synthesis of ethyl 2-chloro-3-bromo-5-aminobenzoate

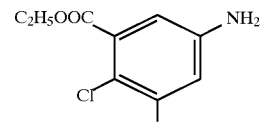

2.25 kg (7.3 mol) of ethyl 2-chloro-3-bromo-5-nitrobenzoate was dissolved in a mixture comprising 4000 ml of concentrated hydrochloric acid and 4000 ml of ethanol. 1 kg of powdered iron was added to the obtained solution in portions so as to maintain the bulk temperature at 80° C. The reaction mixture was cooled, followed by the addition of a saturated brine. The resulting mixture was extracted with ethyl acetate. The organic phase was dried and concentrated under reduced pressure to give 1.8 kg of the title compound as a colorless oil.

$^1$H-NMR(400 MHz, CDCl$_3$); δ(ppm) 7.1(1H, d), 6.9(1H, d), 4.4(2H, q), 3.9(2H, s), 1.2(3H, t).

Example 5

Synthesis of 1-(3-bromo-4-chloro-5-ethoxycarbonyl)phenylpiperazine hydrochloride

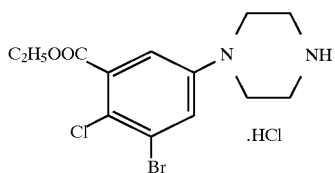

1.8 kg (6.5 mol) of ethyl 2-chloro-3-bromo-5-aminobenzoate and 1.2 kg (6.7 mol) of bis(2-chloroethyl) amine hydrochloride were dissolved in 5000 ml of o-dichlorobenzene. The obtained solution was refluxed under heating for 3 hours and thereafter cooled by allowing to stand, precipitating a crystal. This crystal was recovered by filtration and dried to give 2.4 kg of the title salt.

m.p.; 250° C. or above $^1$H-NMR(400 MHz, CDCl$_3$); δ(ppm) 7.2(1H, d), 7.1(1H, d), 4.4(2H, q), 3.2(4H, m), 3.0(4H, m), 1.4(3H, t).

Example 6

Synthesis of 1-(t-butoxycarbonyl)-4-(3-bromo-4-chloro-5-ethoxycarbonyl)phenylpinerazine

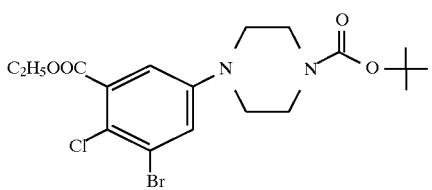

880 g (2.3 mol) of 1-(3-bromo-4-chloro-5-ethoxycarbonyl)phenypiperazine hydrochloride was suspended in a mixture comprising 500 g (5 mol) of triethylamine and 2000 ml of acetonitrile, followed by the dropwise addition of 500 g of di-t-butyl carbonate under cooling with ice. After the completion of the dropwise addition, the resulting mixture was further stirred at room temperature for one hour and then concentrated. The obtained residue was dissolved in ethyl acetate and the obtained solution was washed with water, dried and concentrated under reduced pressure. The obtained residue was crystallized from isopropyl ether to give 1 kg of the title compound as a colorless crystal.

m.p.; 115° C.

$^1$H-NMR(400 MHz, CDCl$_3$); δ(ppm) 7.2(1H, d), 7.1(1H, d), 4.4(2H, q), 3.6(4H, t), 3.2(4H, t), 1.5(9H, s), 1.4(3H, t).

Example 7

Synthesis of 1-(t-butoxycarbonyl)-4-[3-bromo-4-chloro-5-(1-hydroxyyropyl)]phenylpiperazine

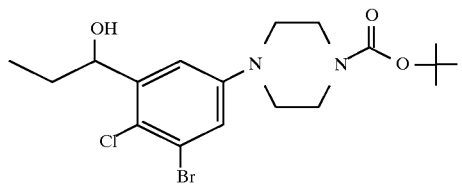

1 kg (2.23 mol) of 1-(t-butoxycarbonyl)-4-(3-bromo-4-chloro-5-ethoxycarbonyl)phenylpiperazine was dissolved in 4000 ml of THF, followed by the dropwise addition of 5.5 mol of ethylmagnesium bromide under cooling with ice. The obtained mixture was further stirred at room temperature for one hour, followed by the addition of a saturated aqueous solution of ammonium chloride. The obtained mixture was extracted with ethyl acetate. The organic phase was washed with water, dried and concentrated under reduced pressure to give 1 kg of the title compound as a colorless oil.

$^1$H-NMR(400 MHz, CDCl$_3$); δ(ppm) 7.1(1H, d), 7.05 (1H, d), 5.0(1H, m), 3.6(4H, t), 3.1(4H, t), 1.6(2H, m), 1.5(9H, s), 1.0(3H, t).

Example 8

Synthesis of 1-(t-butoxycarbonyl)-4-[3-bromo-4-chloro-5-(1-fluoropropyl)]phenylpiperazine

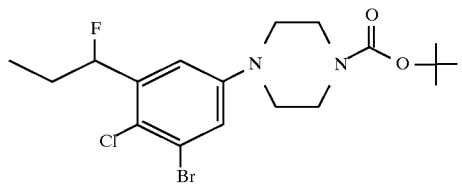

1 kg (2.3 mol) of 1-(t-butoxycarbonyl)-4-[3-bromo-4-chloro-5-(1-hydroxypropyl)]phenylpiperazine was dissolved in 2000 ml of anhydrous methylene chloride, followed by the dropwise addition of 425 g (2.6 mol) of diethylaminosulfur trifluoride (DAST) at −70° C. After the completion of the dropwise addition, the obtained mixture was further stirred for 30 minutes and poured into water. The aqueous phase was extracted with methylene chloride. The methylene chloride phase was washed with water, dried and concentrated under reduced pressure. The obtained residue was purified by silica gel column chromatography (with ethyl acetate and hexane) to give 900 g of the title compound as a colorless oil.

$^1$H-NMR(400 MHz, CDCl$_3$); δ(ppm) 7.1(1H, d), 7.0(1H, d), 5.7(1H, m), 3.6(4H, m), 3.2(4H, m), 1.8(2H, m), 1.5(9H, m), 1.0(3H, t).

Example 9

Synthesis of 1-(t-butoxycarbonyl)-4-[3-(2-formylphenyl)-4-chloro-5-(1-fluoropropyl)]phenylpiperazine

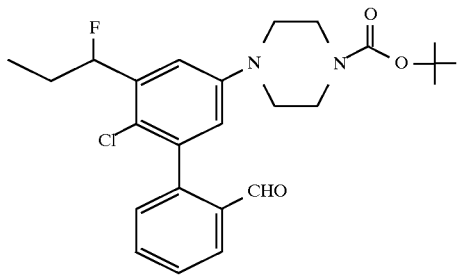

174 g (0.4 mol) of 1-(t-butoxycarbonyl)-4-[3-bromo-4-chloro-5-(1-fluoropropyl)]phenylpipearazine, 114 g (0.6 mol) of 2-(1,3,2-dioxaborinan-2-yl)benzaldehyde (10) described in Synlett, (3), 207–210, 1992, 1 g of tetrakis(triphenylphosphine)palladium (0) and 195 g (0.6 mol) of cesium carbonate were dissolved in 1000 ml of DMF and the obtained solution was maintained at 100° C. for 3 hours to conduct a reaction. The reaction mixture was cooled and then poured into water. The resulting mixture was extracted with ethyl acetate. The organic phase was washed with water, dried and concentrated under reduced pressure. The obtained residue was purified by silica gel column chromatography and recrystallized from an ethyl acetate/hexane mixture to give 165 g of the title compound as a colorless crystal.

m.p.; 135° C.

$^1$H-NMR(400 MHz, CDCl$_3$); δ(ppm) 9.8(1H, d), 8.0(1H, m), 7.7(1H, m), 7.5(1H, m), 7.3(1H, m), 7.1(1H, d), 6.8(1H, d), 5.8(1H, m), 3.6(4H, m), 3.2(4H, m), 1.9(2H, m), 1.5(9H, s), 1.1(3H, t).

Example 10

Synthesis of 1-(t-butoxycarbonyl)-4-[3-(2-hydroxyiminomethylphenyl)-4-chloro-5-(1-fluoropropyl)]phenylpiperazine

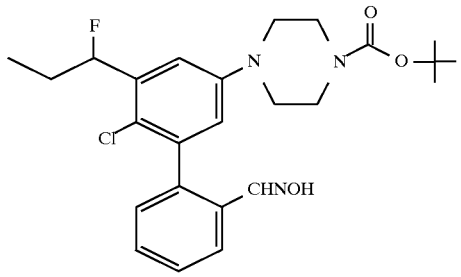

165 g (0.36 mol) of 1-(t-butoxycarbonyl)-4-[3-(2-formylphenyl)-4-chloro-5-(1-fluoropropyl)]phenylpiperazine and 50 g (0.72 mol) of hydroxylamine hydrochloride were dissolved in 100 ml of a 5N aqueous solution of NaOH, followed by the addition of 200 ml of ethanol. The obtained mixture was refluxed under heating for 2 hours and thereafter cooled and concentrated under reduced pressure. The residue was partitioned between water and ethyl acetate. The organic phase was washed with water, dried and concentrated under reduced pressure to give 154 g of the title compound as a colorless oil.

$^1$H-NMR(400 MHz, CDCl$_3$); δ(ppm) 8.0(1H, m), 7.8.(1H, d), 7.6(1H, m), 7.4(1H, m), 7.2(1H, m), 7.1(1H, m), 6.7(1H, m), 5.8(1H, m), 3.6(4H, m), 3.2(4H, m), 1.9(2H, m), 1.5(9H, s), 1.1(3H, t).

Example 11

Synthesis of 1-(t-butoxycarbonyl)-4-[3-(2-cyanophenyl)-4-chloro-5-(1-fluoropropyl)]phenylpiperazine

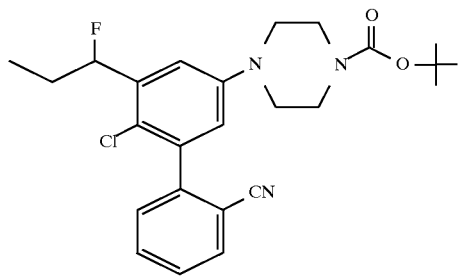

154 g (0.32 mol) of 1-(t-butoxycarbonyl)-4-[3-(2-hydroxyiminomethylphenyl)-4-chloro-5-(1-fluoropropyl)]phenylpiperazine and 40 g of N,N-dimethylaminopyridine were dissolved in a mixture comprising 100 ml of acetic anhydride and 100 ml of pyridine. The obtained solution was heated to 100° C. and maintained at that temperature for one hour to conduct a reaction. The reaction mixture was cooled and then poured into a saturated aqueous solution of sodium hydrogen carbonate. The resulting mixture was extracted with ethyl acetate to give 140 g of the title compound as a colorless crystal.

m.p.; 120° C.

$^1$H-NMR(400 MHz, CDCl$_3$); δ(ppm) 7.8(1H, d), 7.6(1H, t), 7.5(1H, t), 7.4(1H, d), 7.1(1H, d), 6.8(1H, d), 5.9(1H, m), 3.6(4H, m), 3.2(4H, m), 2.0(2H, m), 1.5(9H, s), 1.1(3H, t).

Example 12

Synthesis of 1-[3-(2-cyanophenyl)-4-chloro-5-(1-fluoropropyl)]phenylpiperazine

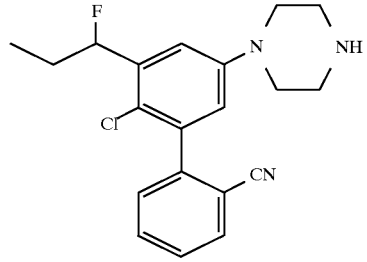

140 g (0.3 mol) of 1-(t-butoxycarbonyl)-4-[3-(2-cyanophenyl)-4-chloro-5-(1-fluoropropyl)]phenylpiperazine was dissolved in a mixture comprising 500 ml of trifluoroacetic anhydride and 500 ml of chloroform. The obtained solution was stirred at 0° C. for 5 hours and distilled to remove the solvent. The residue was recrystallized from ethyl acetate and hexane to give 100 g of the title compound as a colorless crystal.

m.p.; 159° C.

$^1$H-NMR(400 MHz, CDCl$_3$); δ(ppm) 7.8(1H, d), 7.6(1H, t), 7.5(1H, t), 7.4(1H, d), 7.1(1H, d), 6.8(1H, d), 5.9(1H, m), 3.5(1H, b-s), 3.2(4H, m), 3.0(4H, m), 1.9(2H, m), 1.1(3H, t).

Example 13

Synthesis of 1-(2-hydroxyethyl)-4-[3-(2-cyanophenyl)-4-chloro-5-(1-fluoropropyl)]phenylpiperazine

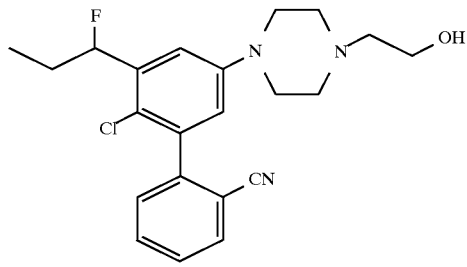

32.1 g (0.09 mol) of 1-[3-(2-cyanophenyl)-4-chloro-5-(1-fluoropropyl)]phenylpiperazine, 12.5 g of 2-bromoethanol and 20 g of triethylamine were dissolved in 100 ml of DMF. The obtained solution was heated to 50° C. and maintained at that temperature for 24 hours to conduct a reaction. The reaction mixture was cooled and then partitioned between ethyl acetate and water. The ethyl acetate phase was washed with water, dried and concentrated under reduced pressure. The residue was purified by silica gel column chromatography (with methylene chloride/methanol) to give 22 g of the title compound as a colorless oil. This oily product was separated with an optically active column to recover a fraction having a plus angle of rotation. Thus, 10 g of the optically active title compound was obtained as a colorless oil. This product was treated with hydrochloric acid to form a salt thereof. The product was recrystallized from methanol/ether to give a hydrochloride of the title compound as a colorless crystal.

m.p. (hydrochloride); 244°–245° C.

$[a]_D$=+6.3° (c=1.03, MeOH) (hydrochloride)

$^1$H-NMR(400 MHz, CDCl$_3$); δ(ppm) 7.8(1H, d), 7.6(1H, t), 7.5(1H, t), 7.4(1H, d), 7.1(1H, d), 6.8(1H, d), 5.8(1H, m), 3.7(2H, t), 3.3(4H, m), 2.7(4H, m), 2.6(2H, t), 1.9(2H, m), 1.1(3H, t).

Example 14

Synthesis of 1-ethyl-4-(3-bromo-4-chloro-5-ethoxycarbonyl)phenylpiperazine

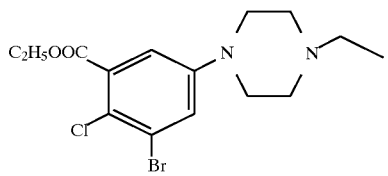

347 g (1 mol) of 1-(3-bromo-4-chloro-5-ethoxycarbonyl)phenypiperazine hydrochloride was dissolved in 1000 ml of DMF, followed by the addition of 207 g (1.5 mol) of potassium carbonate and 120 g (1.1 mol) of ethyl bromide. The obtained mixture was stirred at room temperature overnight, followed by the addition of water. The resulting mixture was extracted with ethyl acetate. The ethyl acetate phase was washed with water, dried and concentrated under reduced pressure to give 338 g of the title compound as a colorless oil.

$^1$H-NMR(400 MHz, CDCl$_3$); δ(ppm) 7.2(1H, d), 7.1(1H, d), 4.4(2H, q), 3.2(4H, m), 2.6(4H, m), 2.5(2H, q), 1.4(3H, t), 1.1(3H, t).

Example 15

Synthesis of 1-ethyl-4-[3-(2-tolyl)-4-chloro-5-ethoxylcarbonyl]phenylpiperazine

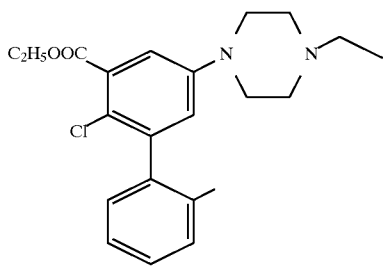

338 g (0.9 mol) of 1-ethyl-4-(3-bromo-4-chloro-5-ethoxycarbonyl)phenylpiperazine and 136 g (1 mol) of 2-tolylboric acid [CH$_3$C$_6$H$_4$B(OH)$_3$] were dissolved in 3000 ml of DMF, followed by the addition of 20 g of palladium acetate, 55 g of triphenylphosphine and 35 g of triethylamine. The obtained mixture was stirred at 100° C. overnight, cooled and partitioned between ethyl acetate and water. The ethyl acetate phase was washed with water, dried and concentrated under reduced pressure. The obtained residue was purified by silica gel column chromatography (with methylene chloride/ethanol) to give 221 g of the title compound as a colorless oil.

$^1$H-NMR(400 MHz, CDCl$_3$); δ(ppm) 8.0(1H, s), 7.3–7.1 (4H, m), 6.8(1H, d), 4.4(2H, q), 3.2(1H, m), 2.6(4H, m), 2.5(2H, q), 1.4(3H, t), 1.2(3H, t), 1.1(3H, t).

Example 16

Synthesis of 1-ethyl-4-[3-(2-tolyl)-4-chloro-5-amino]phenylpiperazine

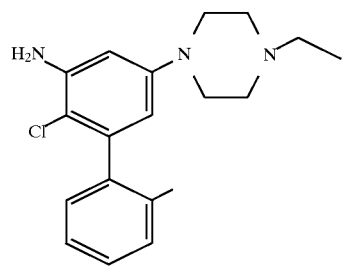

193 g (0.5 mol) of 1-ethyl-4-[3-(2-tolyl)-4-chloro-5-ethoxylcarbonyl]phenylpiperazine was dissolved in a mixture comprising 100 ml of 5N NaOH and 500 ml of methanol. The obtained solution was stirred at room temperature for 3 hours and concentrated under reduced pressure. The obtained residue was dissolved in 300 ml of DMF, followed by the addition of 61 g (0.6 mol) of triethylamine. 65 g (0.6 mol) of ethyl chlorocarbonate was dropwise added to the obtained mixture under cooling with ice. The mixture thus obtained was stirred at 0° C. for 30 minutes, followed by the addition of 39 g (0.6 mol) of sodium azide. The resulting mixture was subjected to reaction for 2 hours and then poured into water to precipitate a white crystal. This white crystal was recovered by filtration and immediately dissolved in 500 ml of toluene. The obtained solution was heated for one hour, followed by the addition of 300 ml of concentrated hydrochloric acid. The obtained mixture was maintained at 100° C. by heating for one hour, cooled, basified with 8N NaOH and extracted with ethyl acetate. The ethyl acetate phase was washed with water, dried and concentrated under reduced pressure. The obtained residue was purified by silica gel column chromatography to give 83 g of the title compound as a colorless oil.

$^1$H-NMR(400 MHz, CDCl$_3$); δ(ppm) 7.3–7.1(4H, m), 6.3(1H, m), 6.2(1H, m), 4.0(2H, s), 3.2(4H, m), 2.6(4H, m), 2.4(2H, q), 2.2(3H, m), 1.1(3H, m).

Example 17

Synthesis of 1-ethyl-4-[3-(2-tolyl)-4-chloro-5-propanesulfonylamino]phenylpiperazine hydrochloride

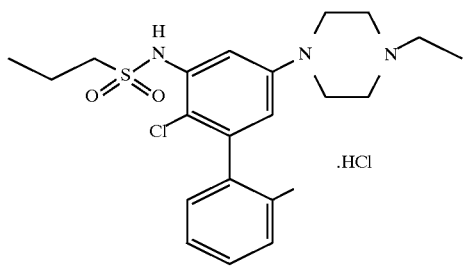

3.3 g (10 mmol) of 1-ethyl-4-[3-(2-tolyl)-4-chloro-5-amino]phenylpiperazine was dissolved in 5 ml of pyridine, followed by the addition of 2.9 g (20 mmol) of propanesulfonyl chloride. The obtained mixture was stirred at room temperature overnight and partitioned between water and ethyl acetate. The ethyl acetate phase was washed with water, dried and concentrated under reduced pressure. The obtained residue was purified by silica gel column chromatography (with methylene chloride/ethanol) to give 2.6 g of the title compound as a colorless oil. This oil was treated with hydrochloric acid to form a hydrochloride thereof, and the product was recrystallized from methanol/ether to give the title compound as a white crystal.

m.p.; 135° C.

$^1$H-NMR(400 MHz, CDCl$_3$); δ(ppm) 7.3(4H, m), 7.0(1H, d), 6.8(1H, m), 4.8(1H, t), 4.4(2H, d), 3.2(4H, m), 2.9(2H, m), 2.6(4H, m), 2.5(2H, q), 2.1(3H, s), 1.8(2H, m), 1.1(3H, t), 1.0(3H, t).

The following compounds were prepared in a similar manner to that of the Example 17 except that the propanesulfonyl chloride was replaced by ethanesulfonyl chloride or butanesulfonyl chloride.

Example 18

1-Ethyl-4-[3-(2-tolyl)-4-chloro-5-ethanesulfonylamino]phenylpiperazine

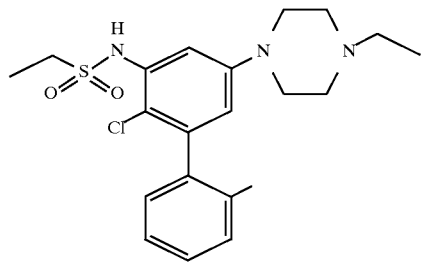

m.p.; 155° C.

$^1$H-NMR(400 MHz, CDCl$_3$); δ(ppm) 7.7–7.2(4H, m), 7.1(1H, d), 6.6(1H, m), 3.7(2H, q), 3.3(4H, m), 2.4(2H, q), 2.1(3H, s), 1.4(3H, t), 1.2(3H, t), 1.1(3H, t).

Example 19

1-Ethyl-4-[3-(2-tolyl)-4-chloro-5-butanesulfonylamino]phenylpiperazine

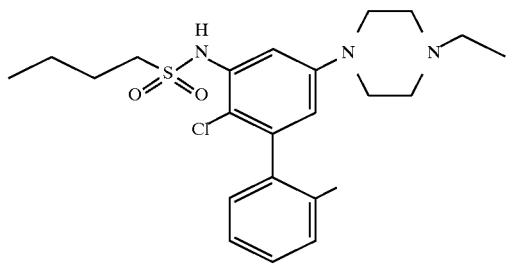

m.p.; 175° C.

$^1$H-NMR(400 MHz, CDCl$_3$); δ(ppm) 7.7–7.2(4H, m), 7.1(1H, d), 6.6(1H, d), 3.2(4H, m), 3.1(2H, m), 2.6(4H, m), 2.5(2H, q), 2.1(3H, s), 1.8(2H, m), 1.4(2H, m), 1.1(3H, t), 0.9(3H, t).

The following compounds were prepared as colorless oils in yields of 85 and 90% respectively in a similar manner to that of the Example 13 except that the 2-bromoethanol was replaced by methyl iodide or ethyl iodide.

Example 20

1-Methyl-4-[3-(2-cyanophenyl)-4-chloro-5-(1-fluoropropyl)]phenylpiperazine

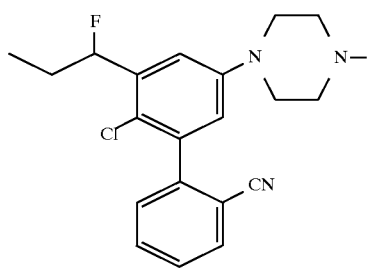

$^1$H-NMR(400 MHz, CDCl$_3$); δ(ppm) 7.8(1H, d), 7.65 (1H, t), 7.5(1H, t), 7.4(1H, d), 7.1(1H, d), 6.8(1H, d), 5.8(1H, m), 3.2(4H, m), 2.6(4H, m), 2.4(3H, s), 2.0(2H, m), 1.1(3H, t).

Example 21

1-Ethyl-4-[3-(2-cyanophenyl)-4-chloro-5-(1-fluoropropyl)]phenylpiperazine

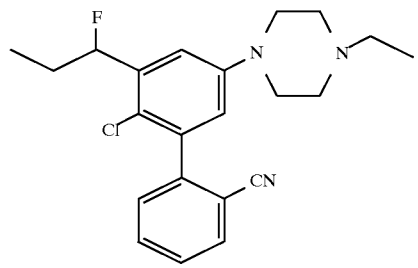

¹H-NMR(400 MHz, CDCl₃); δ(ppm) 7.8(1H, d), 7.6(1H, t), 7.5(1H, t), 7.0(1H, d), 7.1(1H, d), 6.8(1H, d), 5.8(1H, m), 3.3(4H, m), 2.6(4H, m), 2.5(2H, q), 2.0(3H, m), 1.2(3H, t), 1.1(3H, t).

The following compounds were prepared by effecting the process described in Example 9 except that the 2-(1,3,2)-dioxaborinan-2-yl)benzaldehyde was replaced by 2-chlorophenyl-1,3,2-dioxaborinane, and subsequently effecting the process described in Examples 12 or 13.

Example 22

1-Methyl-4-[3-(2-chlorophenyl)-4-chloro-5-(1-fluoropropyl)]phenylpiperazine

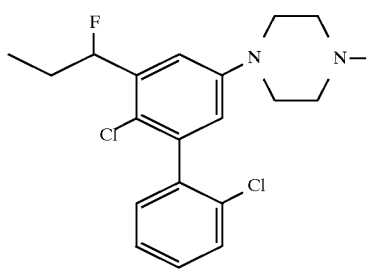

¹H-NMR(400 MHz, CDCl₃); δ(ppm) 7.5(1H, m), 7.3(2H, m), 7.2(1H, m), 7.1(1H, d), 6.8(1H, s), 5.8(1H, m), 3.2(4H, m), 2.3(3H, s), 2.0(3H, m), 1.0(3H, t).

Example 23

1-(2-Hydroxyethyl)-4-[3-(2-chlorophenyl)-4-chloro-5-(1-fluoropropyl)]phenylpiperazine

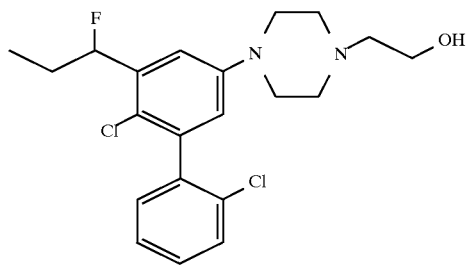

¹H-NMR (400 MHz, CDCl₃); δ(ppm) 7.5(1H, m), 7.3(2H, m), 7.2(1H, m), 7.05(1H, d), 6.8(1H, d), 5.8(1H, m), 3.2(4H, m), 2.6(4H, m), 2.5(2H, q), 2.0(2H, m), 1.2(3H, t), 1.1(3H, d-t).

Example 24

1-Ethyl-4-[3-(2-chlorophenyl)-4-chloro-5-(1-fluoropropyl)]phenylpiperazine

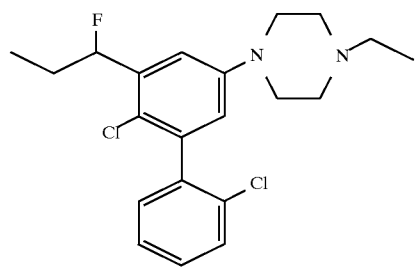

¹H-NMR(400 MHz, CDCl₃); δ(ppm) 7.5–7.2 (4H, m), 7.1(1H, d), 6.8(1H, m), 5.8(1H, m), 3.7(4H, m), 3.2(4H, m), 2.7(4H, m), 2.6(2H, m), 2.0(2H, m), 1.6(1H, b-s), 1.1(3H, d-t).

The following compounds were prepared in a similar manner to that of the Example 9 except that the 2-(1,3,2-dioxaborinan-2-yl)benzaldehyde was replaced by 2-tolyl-1,3,2-dioxaborinane.

Example 25

1-Methyl-4-[3-(2-tolyl)-4-chloro-5-(1fluoropropyl)]phenylpiperazine

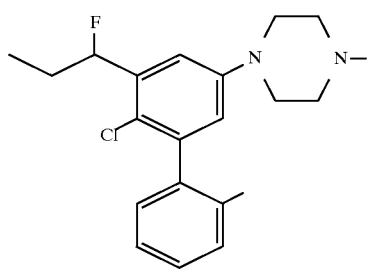

¹H-NMR(400 MHz, CDCl₃); δ(ppm) 7.3–7.2 (3H, m), 7.1(1H, m), 7.0(1H, d), 6.7(1H, d), 6.8(1H, m), 3.2(4H, m), 2.6(4H, m), 2.3(3H, s), 2.1(3H, d), 1.9(2H, m), 1.1(3H, m).

Example 26

1-(2-Hydroxyethyl)-4-[3-(2-tolyl-4-chloro-5-(1-fluoropropyl)]phenylpiperazine

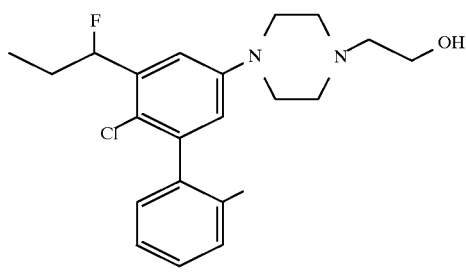

¹H-NMR(400 MHz, CDCl₃); δ(ppm) 7.3–7.2 (3H, m), 7.1(1H, m), 7.0(1H, d), 6.7(1H, d), 5.8(1H, m), 3.7(2H, t), 3.2(4H, m), 2.7(2H, t), 2.6(2H, t), 2.1(3H, d), 1.9(2H, m), 1.1(3H, m).

Example 27

1-Ethyl-4-[3-(2-tolyl)-4-chloro-5-(1-fluoropropyl)]phenylpiperazine

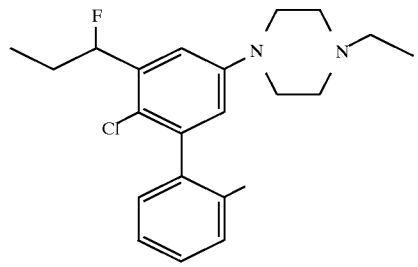

$^1$H-NMR(400 MHz, CDCl$_3$); δ(ppm) 7.3–7.2 (3H, m), 7.1(1H, m), 7.0(1H, d), 6.7(1H, d), 5.8(1H, m), 3.2(4H, m), 2.6(4H, m), 2.5(2H, q), 2.1(3H, d), 1.9(2H, m), 1.15(3H, t), 1.05(3H, m).

The following compounds were prepared first in the same manner as that of the Example 14 except that the ethyl bromide was replaced by methyl iodide, then in the same manner as that of the Example 15 wherein the 2-tolylboric acid was used or replaced by 2-chloroboronic acid.

Example 28

1-Methyl-4-[3-(2-tolyl)-4-chloro-5-ethanesulfonylamino]phenylpiperazine

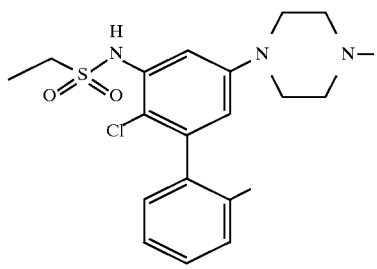

$^1$H-NMR(400 MHz, CDCl$_3$); δ(ppm) 7.3(4H, m), 7.1(1H, d), 6.6(1H, d), 3.3(4H, m), 3.2(2H, q), 2.6(4H, m), 2.4(3H, s), 2.1(3H, s), 1.4(3H, t).

Example 29

1-Methyl-4-[3-(2-tolyl)-4-chloro-5-propanesulfonylamino]phenylpiperazine

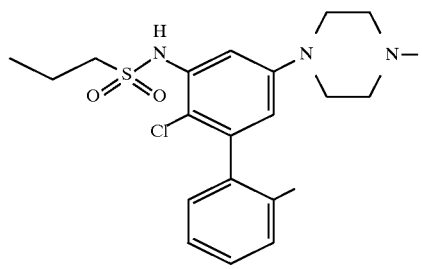

$^1$H-NMR(400 MHz, CDCl$_3$); δ(ppm) 7.5(1H, m), 7.4–7.2 (4H, m), 6.5(1H, m), 3.2(4H, m), 2.6(4H, m), 2.4(3H, s), 1.2(3H, m).

Example 30

1-Methyl-4-[3-(2-tolyl)-4-chloro-5-butanesulfonylamino]phenylpiperazine

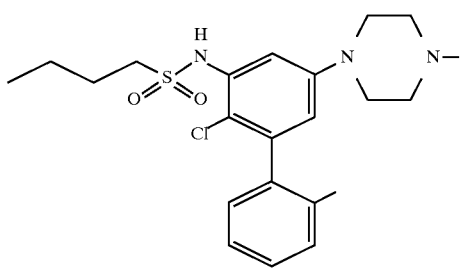

$^1$H-NMR(400 MHz, CDCl$_3$); δ(ppm) 7.3(4H, m), 7.1(1H, d), 6.6(1H, m), 3.2(4H, m), 3.1(2H, m), 2.6(4H, m), 2.3(3H, s), 2.1(3H, s), 1.8(2H, m), 1.4(2H, m), 0.9(3H, t).

Example 31

1-Ethyl-4-[3-(2-chlorophenyl)-4-chloro-5-ethanesulfonylamino]phenylpiperazine

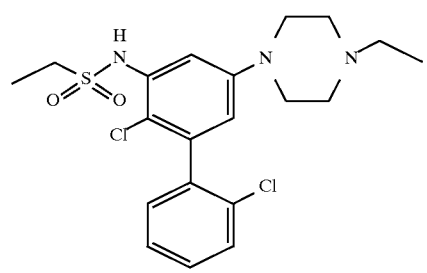

$^1$H-NMR(400 MHz, CDCl$_3$); δ(ppm) 7.7(2H, m), 7.2–7.5 (4H, m), 6.6(1H, d), 3.3(4H, m), 3.1(2H, q), 2.6(4H, m), 2.5(2H, q), 1.4(3H, t), 1.1(3H, t).

Example 32

1-Ethyl-4-[3-(2-chlorophenyl)-4-chloro-5-propanesulfonylamino]phenylpiperazine

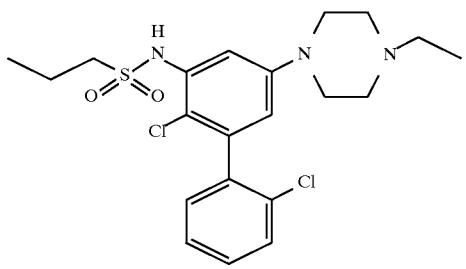

$^1$H-NMR(400 MHz, CDCl$_3$); δ(ppm) 7.5(1H, m), 7.4(2H, m), 7.3(1H, m), 7.0(1H, d), 6.8(1H, d), 3.8(2H, m), 3.6(4H, m), 3.2(2H, m), 3.1(4H, m), 1.7(2H, q), 1.2(3H, t), 0.9(3H, t).

Example 33

1-Ethyl-4-[3-(2-chlorophenyl)-4-chloro-5-butanesulfonylamino]phenylpiperazine

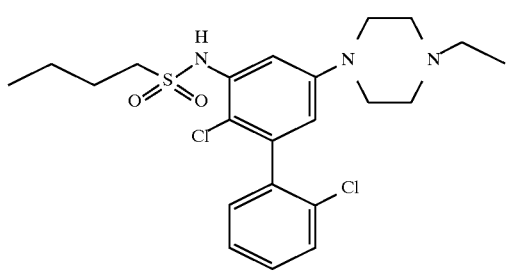

¹H-NMR(400 MHz, CDCl₃); δ(ppm) 7.7–7.2(5H, m), 6.6(1H, m), 3.2(4H, m), 3.1(2H, m), 2.6(4H, m), 2.5(2H, q), 1.8(2H, m), 1.4(2H, m), 1.1(3H, t), 0.9(3H, t).

Example 34

1-Methyl-4-[3-(2-chlorophenyl)-4-chloro-5-ethanesulfonylamino]phenylpiperazine

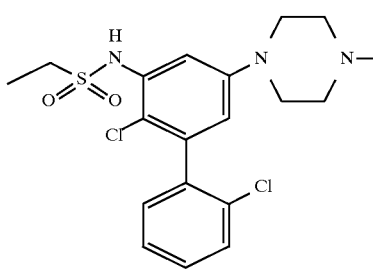

¹H-NMR(400 MHz, CDCl₃); δ(ppm) 7.5(1H, m), 7.4–7.2 (4H, m), 6.8(1H, b-s), 6.6(1H, d), 3.25(4H, m), 3.2(2H, q), 2.6(4H, m), 2.4(3H, s), 1.4(3H, t).

Example 35

1-Methyl-4-[3-(2-chlorophenyl)-4-chloro-5-propanesulfonylamino]phenylpiperazine

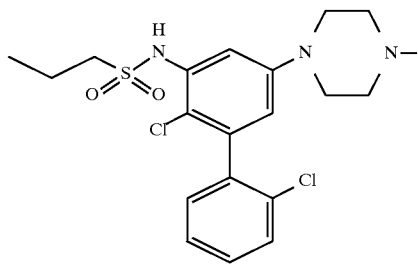

¹H-NMR(400 MHz, CDCl₃); δ(ppm) 7.5(1H, m), 7.4–7.2 (4H, m), 6.6(1H, d), 3.2(4H, m), 3.1(2H, m), 2.6(4H, m), 2.4(3H, s), 1.2(3H, m), 1.0(3H, t).

Example 36

1-Methyl-4-[3-(2-chlorophenyl)-4-chloro-5-butanesulfonylamino]phenylpiperazine

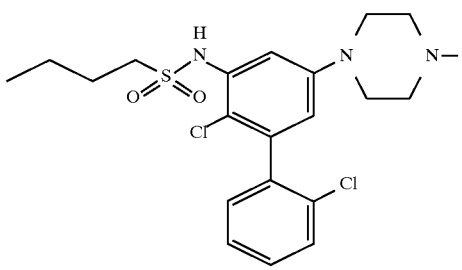

¹H-NMR(400 MHz, CDCl₃); δ(ppm) 7.5(1H, m), 7.4–7.2 (4H, m), 6.6(1H, m), 3.2(4H, m), 3.1(2H, m), 2.6(4H, m), 2.4(3H, s), 1.8(2H, m), 1.4(2H, m), 0.9(3H, t).

Example 37

Synthesis of 1-(t-butoxycarbonyl)-4-(3,5-dibromo-4-methoxy)phenylpiperazine

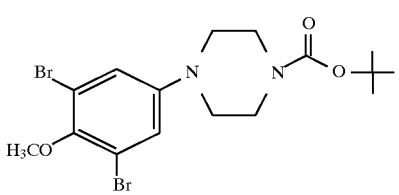

440 g of the title compound was prepared from 350 g of 1-(3,5-dibromo-4-methoxy)phenylpiperazine in a similar manner to that of the Example 6.

¹H-NMR(400 MHz, CDCl₃); δ(ppm) 7.0(2H, m), 3.8(3H, s), 3.5(4H, m), 3.0(4H, m), 1.2(9H, s).

Example 38

Synthesis of 1-(t-butoxycarbonyl)-4-(3-bromo-4-methoxy-5-ethanesulfonyl)phenylpiperazine

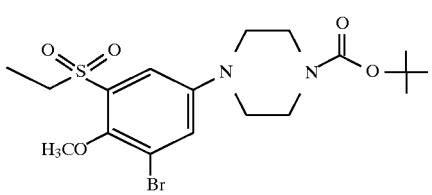

440 g (0.97 mol) of 1-(t-butoxycarbonyl)-4-(3,5-dibromo-4-methoxy)phenylpiperazine was dissolved in 2000 ml of THF, followed by the dropwise addition of 1.2 equivalents of n-butyllithium at −78° C. The obtained mixture was as such stirred for 30 minutes. Sulfur dioxide gas was blown into the resulting mixture for one hour, followed by the addition of 1.2 equivalents of ethyl iodide. The mixture was brought to a room temperature and then partitioned between water and ethyl acetate. The organic phase was washed with water, dried and concentrated under reduced pressure to give 250 g of the title compound.

¹H-NMR(400 MHz, CDCl₃); δ(ppm) 7.4(1H, m), 7.3(1H, m), 4.0(3H, s), 3.6(4H, m), 3.4(2H, q), 3.2(4H, m), 1.5(9H, s), 1.2(3H, t).

Example 39

Synthesis of 1-(t-butoxycarbonyl)-4-[3-(4-fluorophenyl)-4-methoxy-5-ethanesulfonyl]phenylpiperazine

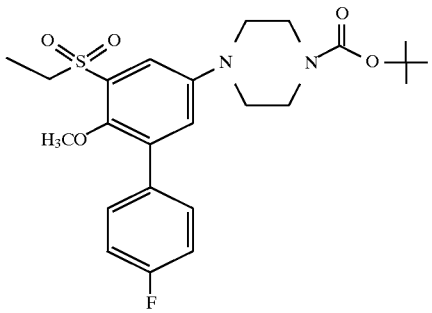

250 g of the title compound was prepared from 440 g of 1-(t-butoxycarbonyl)-4-(3-bromo-4-methoxy-5-ethanesulfonyl)phenylpiperazine in a similar manner to that of the Example 9.

$^1$H-NMR(400 MHz, CDCl$_3$); δ(ppm) 7.6(2H, m), 7.4(1H, m), 7.2(2H, m), 7.0(1H, m), 3.6(4H, m), 3.5(2H, q), 3.4(3H, s), 3.2(4H, m), 1.5(9H, s), 1.3(3H, t).

Example 40

Synthesis of 1-ethyl-4-[3-(4-fluorophenyl)-4-methoxy-5-ethanesulfonyl]phenylpiperazine

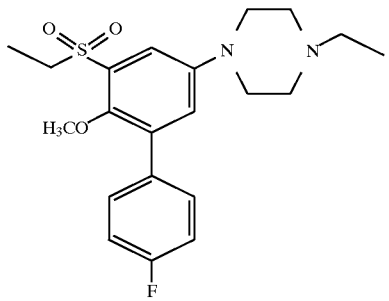

180 g of the title compound was prepared from 250 g of 1-(t-butoxycarbonyl)-4-[3-(4-fluorophenyl)-4-methoxy-5-ethanesulfonyl]phenylpiperazine in a similar manner to that of the Example 12 or 13.

$^1$H-NMR(400 MHz, CDCl$_3$); δ(ppm) 7.6(2H, m), 7.4(1H, m), 7.2(2H, m), 7.05(1H, m), 3.5(2H, q), 3.4(3H, s), 3.3(4H, m), 2.6(4H, m), 2.5(2H, q), 1.3(3H, t), 1.1(3H, t).

Example 41

Synthesis of 1-[3-bromo-4-chloro-5-(1-hydroxypropyl)]phenylpiperazine

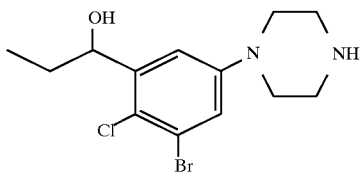

41.7 g (0.1 mol) 1-(t-butoxycarbonyl)-4-[3-bromo-4-chloro-5-(1-hydroxypropyl)]phenylpiperazine was dissolved in 100 ml of 10% hydrochloric acid/ethanol. The obtained solution was stirred at room temperature one whole day and night and then distilled to remove the solvent. The obtained residue was partitioned between ethyl acetate and a saturated aqueous solution of sodium hydrogen carbonate. The organic phase was dehydrated and distilled to remove the solvent, giving 30 g of the title compound as a colorless oil (in a yield of 95%).

$^1$H-NMR(400 MHz, CDCl$_3$); δ(ppm) 7.1(2H, m), 5.0(1H, m), 3.3(4H, m), 3.1(4H, m), 1.7(2H, m), 1.0(3H, t).

Example 42

Synthesis of 1-(2-hydroxyethyl)-4-[3-bromo-4-chloro-5-(1-hydroxypropyl)]phenylpiperazine

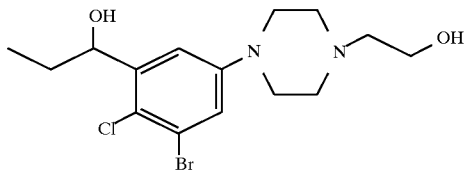

30 g (0.095 mol) of 1-[3-bromo-4-chloro-5-(1-hydroxypropyl)]phenylpiperazine was dissolved in 100 ml of dry DMF, followed by the addition of 20 g of potassium carbonate and 12.5 g (0.1 mol) of bromoethanol. The obtained mixture was stirred at 50° C. one whole day and night and then partitioned between ethyl acetate and water. The organic phase was dehydrated and concentrated under reduced pressure. The residue was purified by column chromatography (with methylene chloride/methanol) to give 17.1 g of the title compound as a colorless oil (in a yield of 50%).

$^1$H-NMR(400 MHz, CDCl$_3$); δ(ppm) 7.1(2H, m), 5.0(1H, m), 3.6(2H, m), 3.2(4H, m), 2.7(4H, m), 2.6(2H, m), 1.7(2H, m), 1.0(3H, t).

Example 43

Synthesis of 1-[3-bromo-4-chloro-5-(1-fluoropropyl)]phenylpiperazine

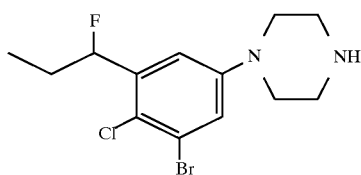

38 g (0.09 mol) of 1-(t-butoxycarbonyl)-4-(3-bromo-4-chloro-5-(1-fluoropropyl)]phenylpiperazine prepared in Example 8 was dissolved in 10% hydrochloric acid/ethanol. The obtained solution was stirred at room temperature one whole day and night and then distilled to remove the solvent. The residue was partitioned between ethyl acetate and a saturated aqueous solution of sodium hydrogen carbonate. The organic phase was dehydrated and distilled to remove the solvent, giving 28.9 g of the title compound as a colorless oil (in a yield of 100%).

$^1$H-NMR(400 MHz, CDCl$_3$); δ(ppm) 7.1(1H, d), 7.0(1H, d), 5.7(1H, m), 3.2(4H, m), 3.1(4H, m), 1.9(2H, m), 1.0(3H, t).

Example 44

Synthesis of 1-(2-hydroxyethyl)-4-[3-bromo-4-chloro-5-(1-fluoropropyl)]phenylpiperazine

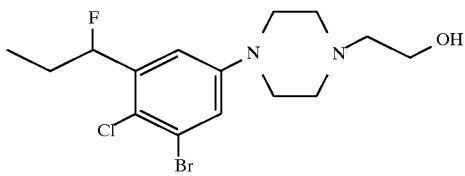

28.9 g (0.09 mol) of 1-[3-bromo-4-chloro-5-(1-fluoropropyl)]phenylpiperazine was dissolved in 50 ml of dry DMF, followed by the addition of 18.6 g (0.135 mol) of potassium carbonate and 12.5 g (0.1 mol) of bromoethanol. The obtained mixture was stirred at 50° C. one whole day and night. Ethyl acetate and water were added to the reaction mixture to conduct partition. The organic phase was dehydrated and concentrated under reduced pressure. The obtained residue was purified by column chromatography (with methylene chloride/methanol) to give 22.8 g of the title compound as a colorless oil (in a yield of 70%).

$^1$H-NMR(400 MHz, CDCl$_3$); δ(ppm) 7.1(1H, d), 7.0(1H, d), 5.7(1H, m), 3.6(2H, m), 3.2(4H, m), 2.7(4H, m), 2.6(2H, m), 1.9(2H, m), 1.0(3H, t).

The following compounds were each prepared in a similar manner to that described above.

Example 45

1-Ethyl-4-(3-phenyl-4-methoxy-5-chloromethyl)phenylpiperazine

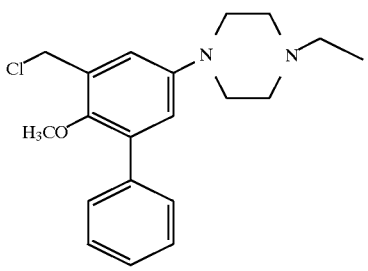

$^1$H-NMR(400 MHz, CDCl$_3$); δ(ppm) 7.55(2H, m), 7.45 (2H, m), 7.4(1H, m), 7.1(1H, m), 6.95(1H, m), 4.75(2H, s), 3.7(4H, m), 3.3(3H, s), 3.2–3.0(6H, m), 1.25(3H, t).

Example 46

Synthesis 1-Ethyl-4-{3-phenyl-4-methoxy-5-[1-fluoro-(4-pentyl)]}phenylpiperazine

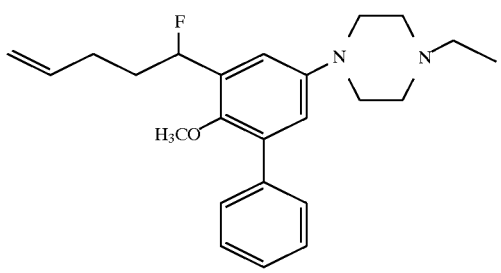

$^1$H-NMR(400 MHz, CDCl$_3$); δ(ppm) 7.6(2H, d), 7.4(3H, m), 7.0(1H, s), 6.9(1H, s), 5.9(1H, m), 5.8(1H, m), 5.0(2H, m), 3.3(3H, s), 3.2(4H, m), 2.6(4H, m), 2.5(2H, q), 2.2(4H, m), 1.1(3H, t).

Mass; MH$^+$383

Example 47

1-Ethyl-4-[3-phenyl-4-methoxy-5-(1-fluorobutyl)]phenylpiperazine

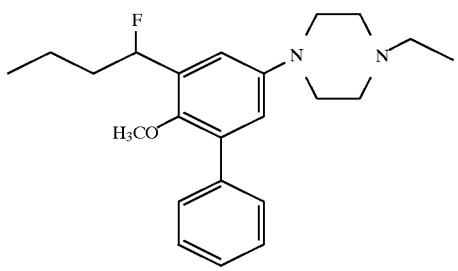

$^1$H-NMR(400 MHz, CDCl$_3$); δ(ppm) 7.6(2H, d), 7.4(3H, m), 7.0(1H, d), 6.8(1H, d), 5.8(1H, m), 3.3(3H, s), 3.2(4H, m), 2.6(4H, m), 2.5(2H, q), 1.9(2H, m), 1.5(2H, m), 1.1(3H, t), 1.0(3H, t).

Example 48

1-Ethyl-4-[3-phenyl-4-methoxy-5-(1-fluoropentyl)]phenylpiperazine

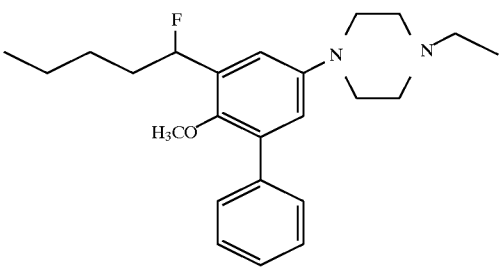

$^1$H-NMR(400 MHz, CDCl$_3$); δ(ppm) 7.6(2H, d), 7.4(3H, m), 7.0(1H, d), 6.8(1H, d), 5.8(1H, m), 3.3(3H, s), 3.2(4H, m), 2.6(4H, m), 2.5(2H, q), 2.0(2H, m), 1.4(4H, m), 1.1(3H, t), 0.9(3H, t).

Example 49

1-Ethyl-4-[3-(2-tolyl)-4-chloro-5-(1-fluorobutyl)]phenylpiperazine

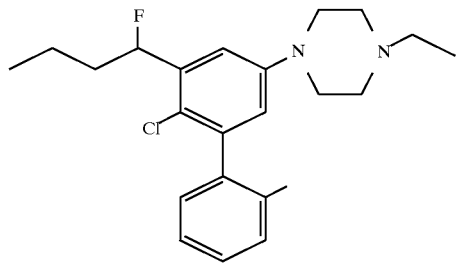

¹H-NMR(400 MHz, CDCl₃); δ(ppm) 7.3–7.1(5H, m), 6.7(1H, d), 5.8(1H, m), 3.2(4H, m), 2.6(4H, m), 2.5(2H, q), 2.1(3H, d), 1.9(2H, m), 1.6(4H, m), 1.1(3H, t), 1.0(3H, t).

Example 50

1-Ethyl-4-[3-(2-tolyl)-4-fluoro-5-(1-fluorobutyl)]phenylpiperazine

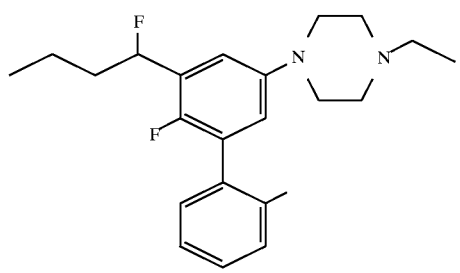

¹H-NMR(400 MHz, CDCl₃); δ(ppm) 7.2(4H, m), 7.0(1H, m), 6.7(1H, m), 5.8(1H, m), 3.2(4H, m), 2.6(4H, m), 2.5(2H, q), 2.2(3H, s), 1.8(4H, m), 1.1(3H, t), 1.0(3H, t).

Mass; MH⁺ 373

Example 51

1-Ethyl-4-[3-(2-tolyl)-4-chloro-5-(1-fluoro-3-methylbutyl)]phenylpiperazine

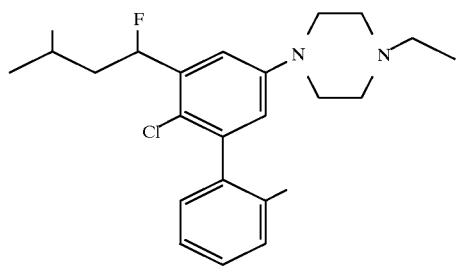

¹H-NMR(400 MHz, CDCl₃); δ(ppm) 7.3–7.0(5H, m), 6.7(1H, d), 5.9(1H, m), 3.2(4H, m), 2.6(4H, m), 2.4(2H, q), 2.1(3H, m), 2.0–1.6(3H, m), 1.1(3H, m), 1.0(6H, d-t).

Mass; MH⁺ 403

Example 52

1-Ethyl-4-[3-(2-tolyl)-4-chloro-5-(1-fluoroethyl)]phenylpiperazine

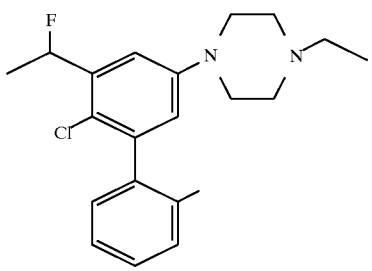

¹H-NMR(400 MHz, CDCl₃); δ(ppm) 7.3–7.1(5H, m), 6.7(1H, m), 6.0(1H, m), 3.2(4H, m), 2.6(4H, m), 2.5(2H, q), 2.1(3H, m), 1.6(3H, m), 1.1(3H, t).

Mass; MH⁺ 361

Example 53

1-Methyl-4-[3-(2-tolyl)-4-chloro-5-(1-fluorobutyl)]phenylpiperazine

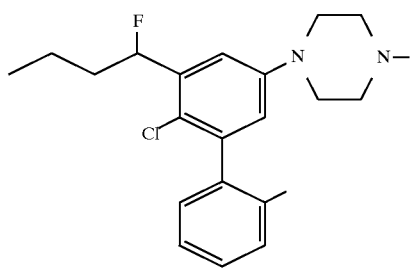

¹H-NMR(400 MHz, CDCl₃); δ(ppm) 7.3(3H, m), 7.1(2H, m), 6.7(1H, m), 5.8(1H, m), 3.2(4H, m), 2.6(4H, m), 2.4(3H, s), 2.1(3H, d), 1.9(2H, m), 1.6(2H, m), 1.0(3H, m).

Example 54

1-Ethyl-4-[3-(2-chlorophenyl)-4-chloro-5-(1-fluorobutyl)]phenylpiperazine

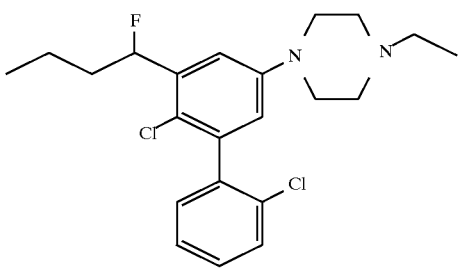

¹H-NMR(400 MHz, CDCl₃); δ(ppm) 7.3(4H, m), 7.1(1H, m), 6.8(1H, m), 5.8(1H, m), 3.2(4H, m), 2.6(4H, m), 2.5(2H, q), 1.9(2H, m), 1.6(2H, m), 1.1(3H, t), 1.0(3H, t).

Example 55

1-Ethyl-4-[3-(2-tolyl)-4-chloro-5-(1,1-difluoropropyl)]phenylpiperazine

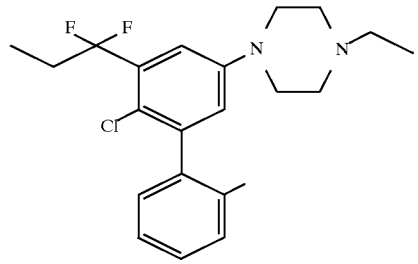

$^1$H-NMR(400 MHz, CDCl$_3$); δ(ppm) 7.4–7.1(5H, m), 6.8(1H, d), 3.2(4H, m), 2.6(4H, m), 2.5–2.3(4H, m), 2.1(3H, s), 1.1(3H, t), 1.0(3H, t).

Example 56

1-Ethyl-4-(3,5-diphenyl-4-methoxy)phenylpiperazine

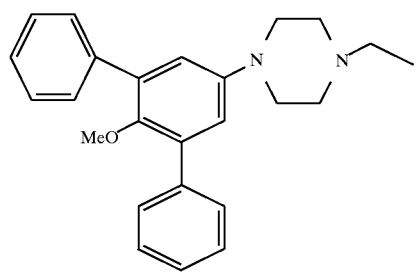

$^1$H-NMR(400 MHz, CDCl$_3$); δ(ppm) 7.6(4H, m), 7.4(4H, m), 7.35(2H, m), 6.9(2H, s), 3.25(4H, m), 3.0(3H, s), 2.6(4H, m), 2.5(2H, q), 1.1(3H, t).

Example 57

1-Ethyl-4-(3-phenyl-4-methoxy)phenylpiperazine

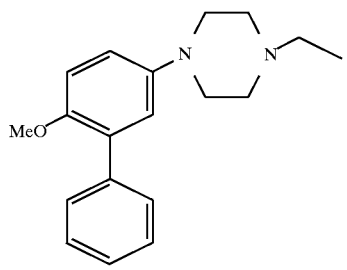

$^1$H-NMR(400 MHz, CDCl$_3$); δ(ppm) 7.5(2H, m), 7.4(2H, m), 7.3(1H, m), 7.0(1H, m), 6.9(1H, m), 3.75(3H, s), 3.2(4H, m), 2.6(4H, m), 2.45(2H, q), 1.1(3H, t).

Example 58

1-Ethyl-4-(3,5-diphenyl-4-hydroxy)phenylpiperazine

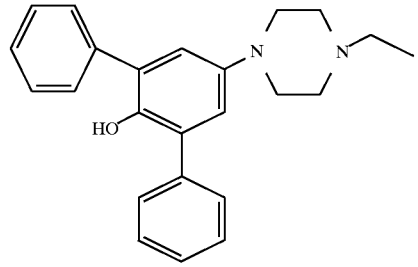

$^1$H-NMR(400 MHz, CDCl$_3$); δ(ppm) 7.6(4H, m), 7.45(4H, m), 7.4(2H, m), 6.9(2H, s), 3.2(4H, m), 2.6(4H, m), 2.45(2H, q), 1.1(3H, t).

Example 59

1-Ethyl-4-(3-phenyl-4-methoxy-5-propyl)phenylpiperazine

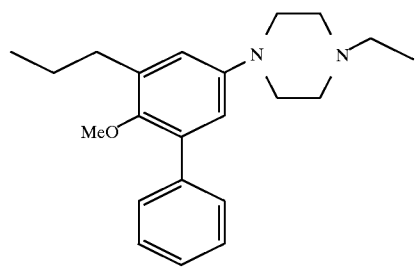

$^1$H-NMR(400 MHz, CDCl$_3$); δ(ppm) 7.6(2H, d), 7.4(2H, m), 7.3(1H, m), 6.8(2H, m), 3.3(3H, s), 3.2(4H, m), 2.6(4H, m), 2.6(2H, t), 2.5(2H, q), 1.6(2H, m), 1.15(3H, t), 1.0(3H, t).

Example 60

1-Ethyl-4-(3,5-diphenyl-4-isopropoxy)phenylpiperazine

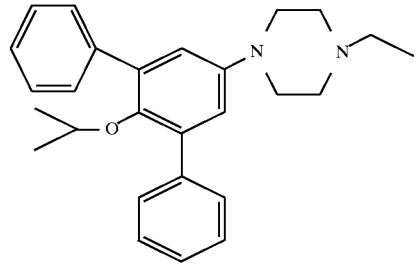

$^1$H-NMR(400 MHz, CDCl$_3$); δ(ppm) 7.6(4H, d), 7.4(4H, m), 7.3(2H, m), 6.9(2H, s), 3.4(1H, m), 3.25(4H, m), 2.6(4H, m), 2.5(2H, q), 1.1(3H, t), 1.6(6H, d).

Example 61

1-Ethyl-4-(3-phenyl-4-isopropoxy)phenylpiperazine

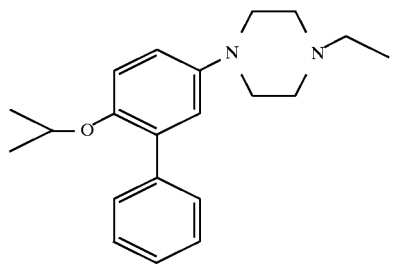

$^1$H-NMR(400 MHz, CDCl$_3$); δ(ppm) 7.6(4H, d), 7.4(2H, m), 7.3(1H, m), 7.0–6.0(3H, m), 4.2(1H, m), 3.2(4H, m), 2.6(4H, m), 2.45(2H, q), 1.2(3H, t).

Example 62

1-Ethyl-4-(3-phenyl-4-hydroxy)phenylpiperazine

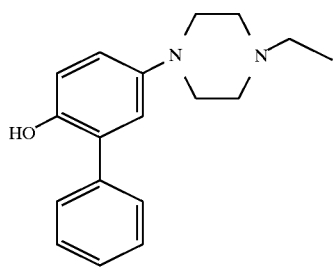

$^1$H-NMR(400 MHz, CDCl$_3$); δ(ppm) 7.5(4H, m), 7.4(1H, m), 6.9(2H, m), 6.85(1H, m), 3.15(4H, m), 2.6(4H, m), 2.5(2H, q), 1.1(3H, t).

Example 63

1-Ethyl-4-[2-methoxy-3-phenyl-5-(3-hydroxypropyl)]phenylpiperazine

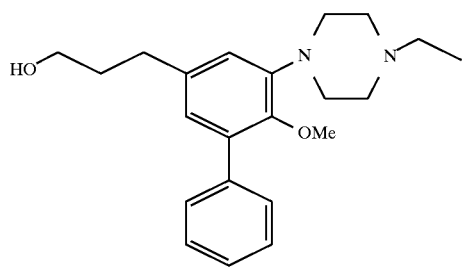

$^1$H-NMR(400 MHz, CDCl$_3$); δ(ppm) 7.60(2H, d), 7.40(2H, m), 7.35(1H, m), 6.8(2H, s), 3.6(2H, t), 3.3(3H, s), 3.2(4H, m), 2.8(2H, t), 2.6(5H, m), 2.5(2H, q), 1.9(2H, m), 1.15(3H, t).

Example 64

1-(2-Hydroxyethyl)-4-(3,5-diphenyl-4-methoxy)phenylpiperazine

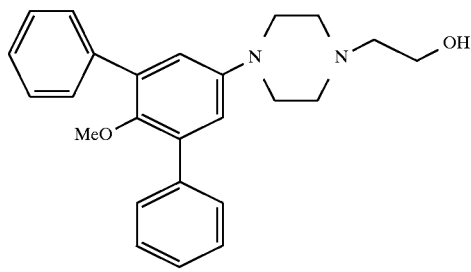

$^1$H-NMR(400 MHz, CDCl$_3$); δ(ppm) 7.6(4H, m), 7.4(4H, m), 7.35(2H, m), 6.9(2H, s), 3.65(2H, m), 3.2(4H, m), 3.1(3H, s), 2.7(4H, m), 2.6(2H, t).

Example 65

1-Ethyl-4-[3-(4-fluorophenyl)-4-methoxy-5-propyl)]phenylpiperazine

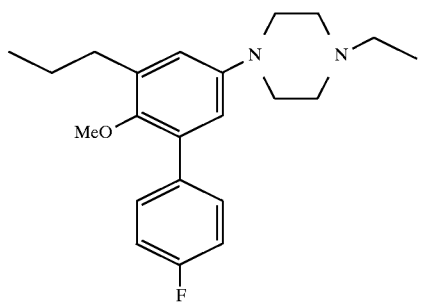

$^1$H-NMR(400 MHz, CDCl$_3$); δ(ppm) 7.6(2H, m), 7.1(2H, m), 6.75(2H, m), 3.3(3H, s), 3.2(4H, m), 2.6(4H, m), 2.45(2H, q), 1.65(2H, m), 1.1(3H, t), 1.0(3H, t).

Example 66

1-Ethyl-4-[3-phenyl-4-methoxy-5-(2-hydroxyethyl)]phenylpiperazine

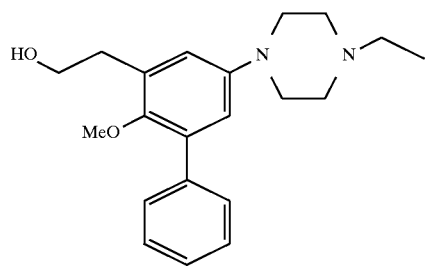

$^1$H-NMR(400 MHz, CDCl$_3$); δ(ppm) 7.6(2H, m), 7.4(2H, m), 7.35(1H, m), 6.8(2H, t), 3.8(2H, t), 3.3(3H, s), 3.2(4H, m), 3.1(2H, t), 2.6(4H, m), 2.5(2H, q), 1.1(3H, t).

Example 67

1-Ethyl-4-[2-methoxy-3-phenyl-5-(2-hydroxyethyl)]phenylpiperazine

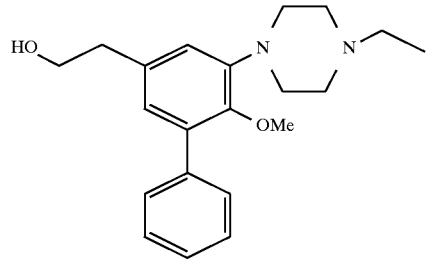

$^1$H-NMR(400 MHz, CDCl$_3$); δ(ppm) 7.6(2H, m), 7.4(2H, m), 7.35(1H, m), 6.8(2H, s), 3.9(2H, t), 3.3(3H, s), 3.2(4H, m), 2.9(2H, t), 2.6(4H, m), 2.5(2H, t), 1.1(3H, t).

Example 68

1-Ethyl-4-[3-phenyl-4-methoxy-5-(3-methoxypropyl)]phenylpiperazine

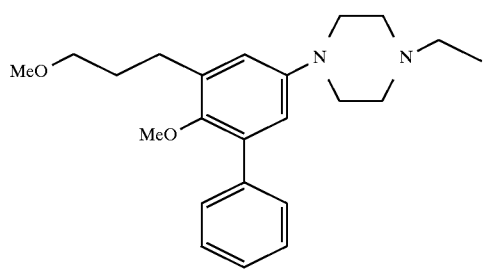

$^1$H-NMR(400 MHz, CDCl$_3$); δ(ppm) 7.6(2H, d), 7.4(2H, m), 7.3(1H, m), 6.8(2H, m), 3.45(2H, m), 3.40(3H, t), 3.30(3H, s), 3.20(4H, m), 2.7(2H, t), 2.6(4H, m), 2.5(2H, q), 1.9(2H, m), 1.1(3H, t).

Example 69

1-Ethyl-4-[3-phenyl-4-methoxy-5-(3-methoxymethoxypropyl)]phenylpiperazine

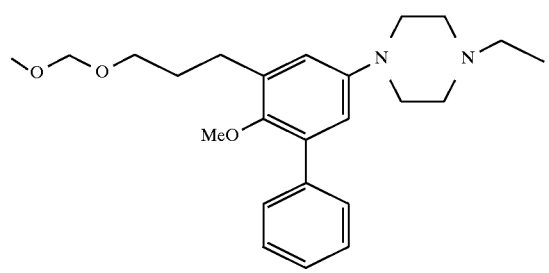

$^1$H-NMR(400 MHz, CDCl$_3$); δ(ppm) 7.6(2H, d), 7.4(2H, m), 7.35(1H, m), 6.8(2H, m), 3.6(2H, t), 3.4(3H, s), 3.3(3H, s), 3.2(4H, m), 2.8(2H, t), 2.6(4H, m), 2.5(2H, q), 2.0(2H, m), 1.1(3H, t).

Example 70

1-Ethyl-4-(3-phenyl-4-methoxy-5-ethyl)phenylpiperazine

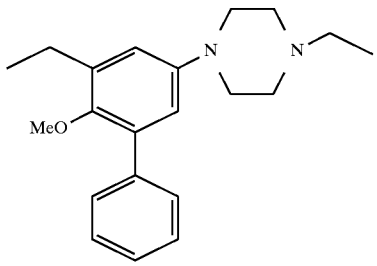

$^1$H-NMR(400 MHz, CDCl$_3$); δ(ppm) 7.6(2H, d), 7.4(2H, m), 7.35(1H, m), 6.8(2H, m), 3.3(3H, s), 3.2(4H, m), 2.7(2H, q), 2.6(4H, m), 2.5(2H, q), 1.25(3H, t), 1.1(3H, t).

Example 71

1-Ethyl-4-[3-phenyl-4-methoxy-5-(3-cyanopropyl)]phenylpiperazine

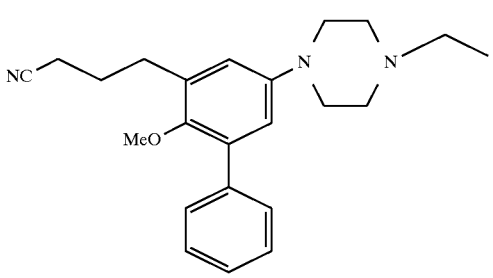

$^1$H-NMR(400 MHz, CDCl$_3$); δ(ppm) 7.6(2H, d), 7.4(2H, m), 7.35(1H, m), 6.8(2H, m), 3.3(3H, s), 3.2(4H, m), 2.8(2H, t), 2.6(4H, m), 2.5(2H, q), 2.4(2H, t), 2.0(2H, m), 1.1(3H, t).

Example 72

1-(2-Fluoroethyl)-4-[3-(4-fluorophenyl)-4-methoxy-5-propyl]phenylpiperazine

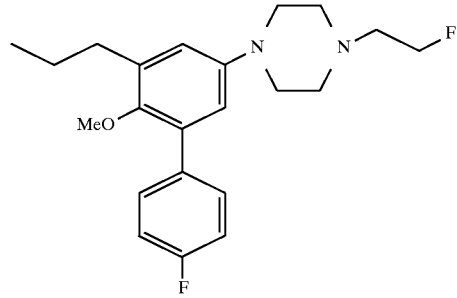

$^1$H-NMR(400 MHz, CDCl$_3$); δ(ppm) 7.6(2H, m), 7.1(2H, m), 6.75(2H, m), 4.6(2H, d-t), 3.3(3H, s), 3.2(4H, m), 2.7(4H, m), 2.7(2H, m), 1.7(2H, m), 1.0(3H, t).

Example 73

1-Ethyl-4-[3-(4-methoxyphenyl)-4-methoxy-5-propyl]phenylpiperazine

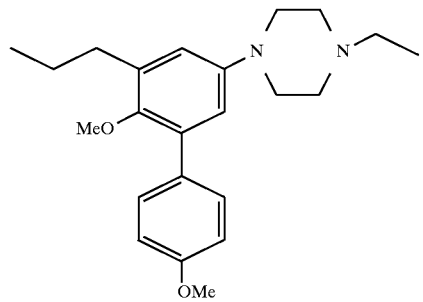

$^1$H-NMR(400 MHz, CDCl$_3$); δ(ppm) 7.5(2H, m), 6.95(2H, m), 6.75(2H, m), 3.85(3H, s), 3.3(3H, s), 3.2(4H, m), 2.6(4H, m), 2.45(2H, q), 1.7(2H, m), 1.1(3H, t), 1.0(3H, t).

Example 74

1-Ethyl-4-(3-phenyl-4-methoxy-5-methoxycarbonyl)phenylpiperazine

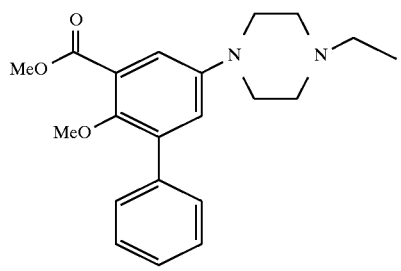

$^1$H-NMR(400 MHz, CDCl$_3$); δ(ppm) 7.6(2H, d), 7.4(2H, m), 7.3(1H, m), 7.0(1H, m), 3.95(3H, s), 3.4(3H, s), 3.2(4H, m), 2.6(4H, m), 2.5(2H, q), 1.1(3H, t).

Example 75

1-Ethyl-4-[3-phenyl-4-methoxy-5-(2-hydroxypropyl)]phenylpiperazine

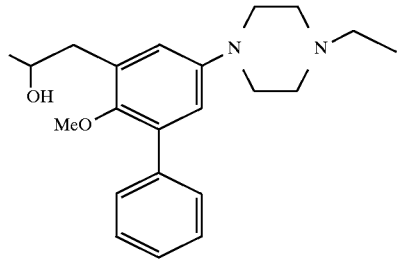

$^1$H-NMR(400 MHz, CDCl$_3$); δ(ppm) 7.6(2H, d), 7.4(2H, m), 7.35(1H, m), 6.8(2H, s), 4.1(1H, m), 3.3(3H, s), 3.2(4H, m), 3.0(1H, b-s), 2.8(2H, m), 2.6(4H, m), 2.4(2H, q), 1.25(3H, d), 1.1(3H, t).

Example 76

1-Ethyl-4-[3-phenyl-4-methoxy-5-(2-fluoroethyl)]phenylpiperazine

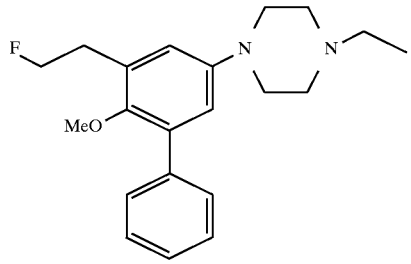

$^1$H-NMR(400 MHz, CDCl$_3$); δ(ppm) 7.6(2H, d), 7.4(2H, m), 7.35(1H, m), 6.8(2H, m), 4.75(2H, t), 4.6(2H, t), 3.3(3H, s), 3.2(4H, m), 3.1(2H, t), 3.05(2H, t), 2.6(4H, m), 2.5(2H, q), 1.15(3H, t).

Example 77

1-Ethyl-4-[3-phenyl-4-methoxy-5-(3-fluoropropyl)]phenylpiperazine

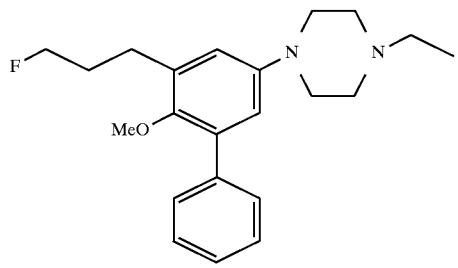

$^1$H-NMR(400 MHz, CDCl$_3$); δ(ppm) 7.6(2H, d), 7.4(2H, m), 7.35(1H, m), 6.8(2H, s), 4.6(2H, t), 4.45(2H, t), 3.3(3H, s), 3.2(4H, m), 2.8(2H, m), 2.6(4H, m), 2.5(H, q), 2.05(2H, m), 1.15(3H, t).

Example 78

1-Ethyl-4-[3-(4-fluorophenyl)-4-methoxy-5-isopropyl]phenylpiperazine

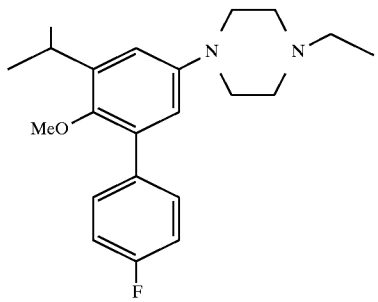

$^1$H-NMR(400 MHz, CDCl$_3$); δ(ppm) 7.55(2H, m), 7.1(2H, m), 6.8(1H, m), 6.7(1H, m), 3.4(1H, m), 3.3(3H, s), 3.2(4H, m), 2.6(4H, m), 2.5(2H, q), 1.25(6H, s), 1.1(3H, t).

Example 79

1-Ethyl-4-[3-(4-fluorophenyl)-4-methoxy-6-isopropyl]phenylpiperazine

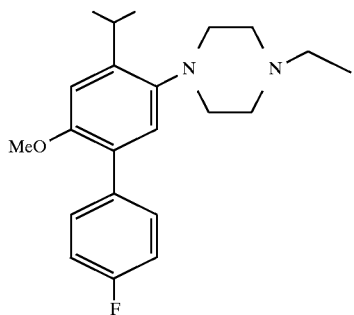

$^1$H-NMR(400 MHz, CDCl$_3$); δ(ppm) 7.55(2H, m), 7.4 (1H, m), 7.1(2H, m), 6.85(1H, m), 3.8(3H, s), 3.6(1H, m), 2.9(4H, m), 2.5(2H, q), 1.55(4H, b-s), 1.25(6H, d), 1.1(3H, t).

Example 80

1-Ethyl-4-[3-phenyl-4-methoxy-5-(1-hydroxyisopropyl)]phenylpiperazine

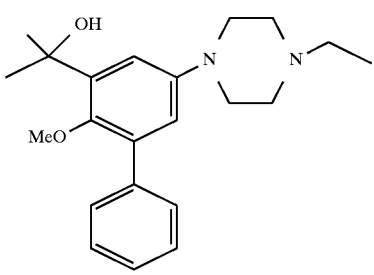

$^1$H-NMR(400 MHz, CDCl$_3$); δ(ppm) 7.6(2H, d), 7.4(2H, m), 7.35(1H, m), 6.95(1H, m), 6.8(1H, m), 3.3(3H, s), 3.2(4H, m), 2.6(4H, m), 2.45(2H, q), 1.6(6H, s), 1.1(3H, t).

Example 81

1-Ethyl-4-[3-phenyl-4-methoxy-5-(1-butoxypropyl)]phenylpiperazine

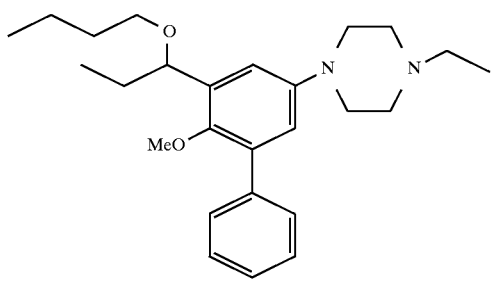

$^1$H-NMR(400 MHz, CDCl$_3$); δ(ppm) 7.6(2H, m), 7.4(2H, m), 7.35(1H, m), 7.0(1H, d), 6.8(1H, m), 4.6(1H, m), 3.4(1H, m), 3.35(1H, m), 3.3(3H, s), 3.2(4H, m), 2.6(4H, m), 2.5(2H, q), 1.75(2H, m), 1.6(2H, m), 1.4(2H, m), 1.1(3H, t), 1.0(3H, t), 0.9(3H, t).

Example 82

1-Ethyl-4-(3-phenyl-4-methoxy-5-propionyl)phenylpiperazine

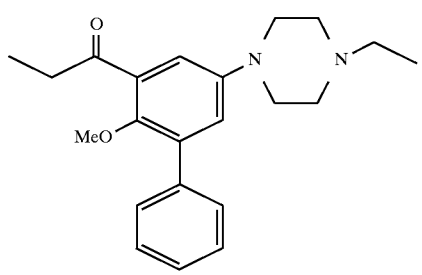

$^1$H-NMR(400 MHz, CDCl$_3$); δ(ppm) 7.55(2H, m), 7.4 (3H, m ), 7.0(2H, m), 3.3(3H, s), 3.2(4H, m), 3.0(2H, q), 2.6(4H, m), 3.42(2H, q), 1.2(3H, t), 1.1(3H, t).

Example 83

1-Ethyl-4-[3-phenyl-4-methoxy-5-(1-hydroxypropyl)] phenylpiperazine

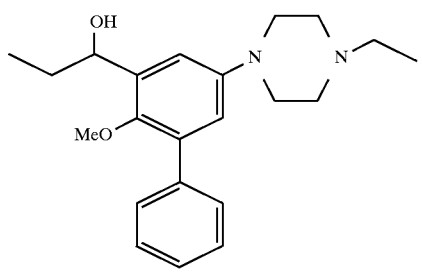

$^1$H-NMR(400 MHz, CDCl$_3$); δ(ppm) 7.5(2H, m), 7.35 (3H, m), 7.0(1H, m), 6.7(1H, m), 4.9(1H, m), 4.0(1H, b-s), 3.25(3H, s), 3.2–3.0(4H, m), 2.6(4H, m), 2.45(2H, m), 1.8(2H, m), 1.1(3H, t), 1.0(3H, t).

Example 84

1-Ethyl-4-[3-(2-fluorophenyl)-4-methoxy-5-propyl] phenylpiperazine

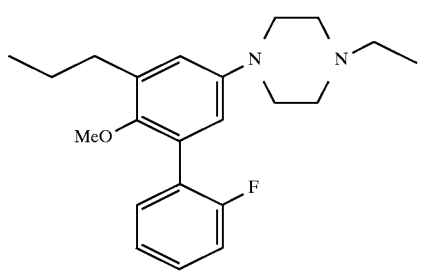

$^1$H-NMR(400 MHz, CDCl$_3$); δ(ppm) 7.4–7.3(2H, m), 7.2–7.1(2H, m), 6.8(1H, d), 6.7(1H, d), 3.3(3H, s), 3.2(4H, m), 2.6(6H, m), 2.5(2H, q), 1.7(2H, m), 1.15(3H, t), 1.0(3H, t).

Example 85

1-Ethyl-4-[3-(4-trifluoromethylphenyl)-4-methoxy-5-propyl]phenylpiperazine

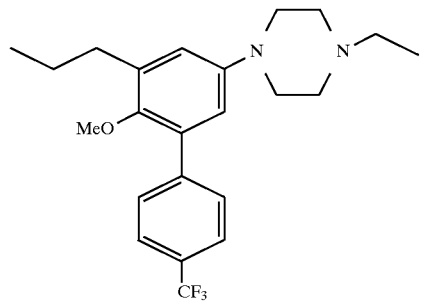

¹H-NMR(400 MHz, CDCl₃); δ(ppm) 7.7(4H, m), 6.8(1H, m), 6.7(1H, m), 3.3(3H, s), 3.2(4H, m), 2.6(6H, m), 2.45(2H, q), 1,7(2H, m), 1.15(3H, t), 1.0(3H, t).

Example 86

1-Ethyl-4-[3-phenyl-4-methoxy-5-(1-fluoroisopropyl)]phenylpiperazine

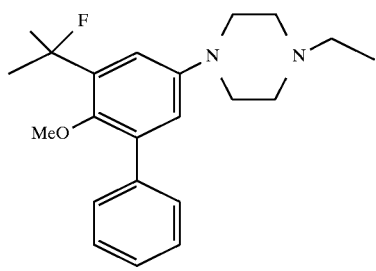

¹H-NMR(400 MHz, CDCl₃); δ(ppm) 7.55(2H, m), 7.4 (3H, m), 7.1(1H, d), 6.8(1H, d), 3.2(3H, s), 3.2(4H, m), 2.6(4H, m), 2.5(2H, q), 1.8(6H, d), 1.15(3H, t).

Example 87

1-Ethyl-4-[3-phenyl-4-methoxy-5-(2-hydroxyisopropyl)]phenylpiperazine

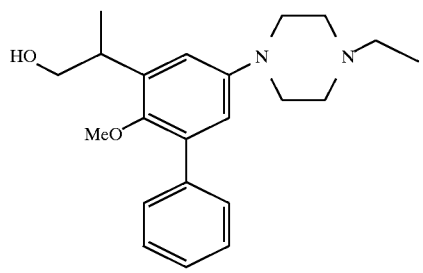

¹H-NMR(400 MHz, CDCl₃); δ(ppm) 7.6(2H, d), 7.4(2H, t), 7.35(1H, m), 6.8(2H, m), 3.75(2H, d), 3.4(1H, m), 3.3(3H, s), 3.2(4H, m), 2.6(4H, m), 2.5(2H, q), 1.95(2H, m), 1.6(2H, m), 1.3(3H, d), 1.1(3H, t).

Example 88

1-Ethyl-4-[3-phenyl-4-methoxy-5-(1-fluoropropyl)]phenylpiperazine

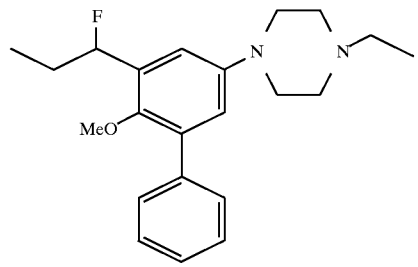

¹H-NMR(400 MHz, CDCl₃); δ(ppm) 7.6(2H, m), 7.4(3H, m), 7.0(1H, m), 6.85(1H, m), 5.75(1H, m), 3.3(3H, s), 3.2(4H, m), 2.6(4H, m), 2.5(2H, q), 2.0(2H, m), 1.15(3H, t), 1.05(3H, t).

Example 89

1-Ethyl-4-(3-phenyl-4-methoxy-5-cyano)phenylpiperazine

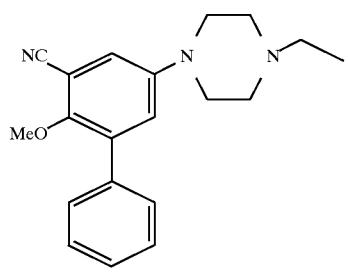

¹H-NMR(400 MHz, CDCl₃); δ(ppm) 7.5(2H, m), 7.4(3H, m), 7.1(1H, d), 7.1(1H, d), 3.6(3H, s), 3.2(4H, m), 2.6(4H, m), 2.5(2H, q), 1.1(3H, t).

Example 90

1-Ethyl-4-[3-phenyl-4-methoxy-5-(2-fluoro)]phenylpiperazine

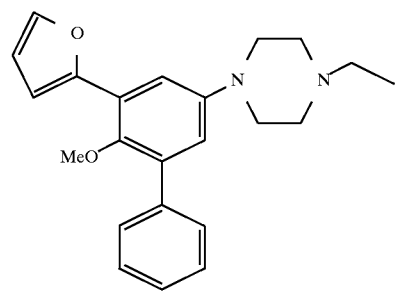

¹H-NMR(400 MHz, CDCl₃); δ(ppm) 7.6(2H, m), 7.5–7.3 (5H, m), 7.0(1H, d), 6.8(1H, d), 6.5(1H, d), 3.3(3H, s), 5.25(4H, m), 2.6(4H, m), 2.5(2H, q), 1.2(3H, t).

Example 91

1-Ethyl-4-[3-(2,4-difluorophenyl)-4-methoxy-5-propyl]phenylpiperazine

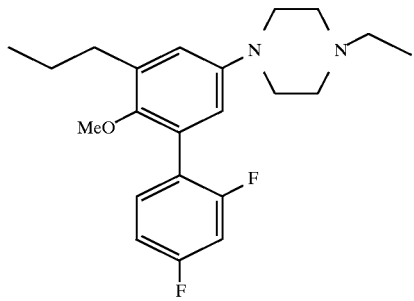

¹H-NMR(400 MHz, CDCl₃); δ(ppm) 7.4(1H, m), 7.0–6.9 (2H, m), 6.8(1H, m), 6.65(1H, m), 3.3(3H, s), 3.2(4H, m), 2.6(6H, m), 2.5(2H, q), 1.7(2H, m), 1.15(3H, t), 1.0(3H, t).

Example 92

1-Ethyl-4-(3-phenyl-4-methoxy-5-phenylacetyl)phenylpiperazine

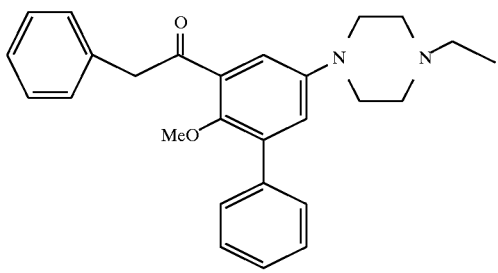

¹H-NMR(400 MHz, CDCl₃); δ(ppm) 7.6(2H, d), 7.45–7.2 (8H, m), 7.0(2H, s), 4.35(2H, s), 3.35(3H, s), 3.2(4H, m), 2.6(4H, m), 2.45(2H, m), 1.1(3H, t).

Example 93

1-Ethyl-4-[3-phenyl-4-methoxy-5-(4-fluorophenyl)acetyl]phenylpiperazine

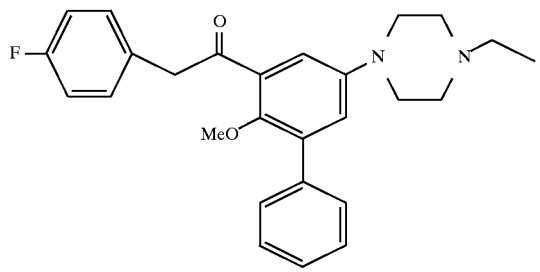

¹H-NMR(400 MHz, CDCl₃); δ(ppm) 7.6(2H, d), 7.4(3H, m), 7.25(2H, m), 7.0(4H, m), 4.3(2H, s), 3.35(3H, s), 3.2(4H, m), 2.6(4H, m), 2.45(2H, q), 1.1(3H, t).

Example 94

1-Ethyl-4-[3-phenyl-4-methoxy-5-(1-hydroxyphenethyl)]phenylpiperazine

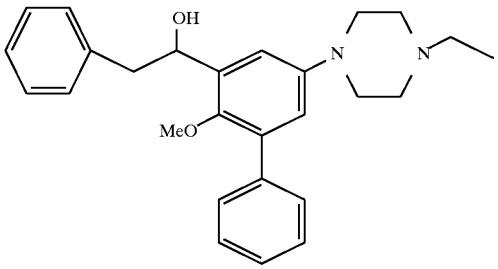

¹H-NMR(400 MHz, CDCl₃); δ(ppm) 7.6(2H, m), 7.4–7.2 (8H, m), 7.0(1H, m), 6.8(1H, m), 5.2(1H, m), 3.3(3H, s), 3.2(4H, m), 3.0(1H, m), 2.6(4H, m), 2.5(2H, q), 1.1(3H, t).

Example 95

1-Ethyl-4-[3-phenyl-4-methoxy-5-(2-tetrahydrofuranyl)]phenylpiperazine

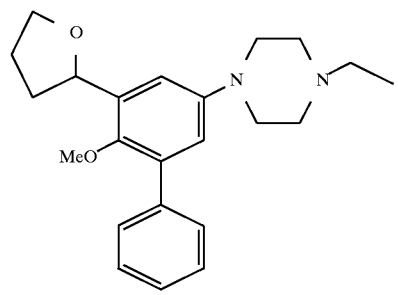

¹H-NMR(400 MHz, CDCl₃); δ(ppm) 7.6(2H, m), 7.4(2H, t), 7.35(1H, t), 7.0(1H, s), 6.8(1H, s), 5.2(1H, t), 4.1(1H, m), 3.95(1H, m), 3.3(3H, s), 3.2(4H, m), 2.6(4H, m), 2.5(2H, m), 2.0(2H, m), 1.8(2H, m), 1.15(3H, t).

Example 96

1-Ethyl-4-[3-phenyl-4-methoxy-5-(1-fluorophenethyl)]phenylpiperazine

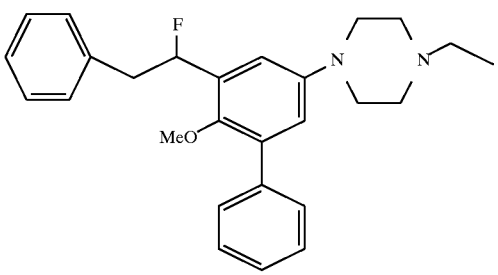

¹H-NMR(400 MHz, CDCl₃); δ(ppm) 7.6(2H, d), 7.4–7.2 (8H, m), 6.95(1H, m), 6.85(1H, m), 6.0(1H, m), 3.25(3H, s), 3.2(4H, m), 2.6(4H, m), 2.5(2H, q), 1.1(3H, t).

Example 97

1-Ethyl-4-[3-phenyl-4-methoxy-5-(2-pyridyl)]phenylpiperazine

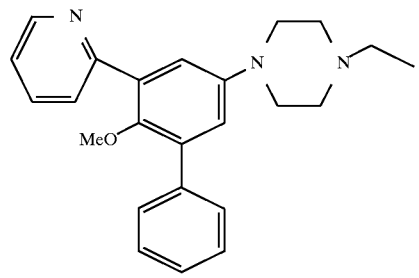

$^1$H-NMR(400 MHz, CDCl$_3$); δ(ppm) 8.7(1H, m), 7.8(1H, d), 7.7(1H, t), 7.6(2H, d), 7.4(2H, t), 7.35(1H, m), 7.3(1H, d), 7.0(1H, d), 3.3(4H, m), 3.2(3H, s), 2.6(4H, m), 2.5(2H, q), 1.1(3H, t).

Example 98

1-Ethyl-4-{3-phenyl-4-methoxy-5-[4-fluoro-(1-hydroxyimino)phenethyl]}phenylpiperazine

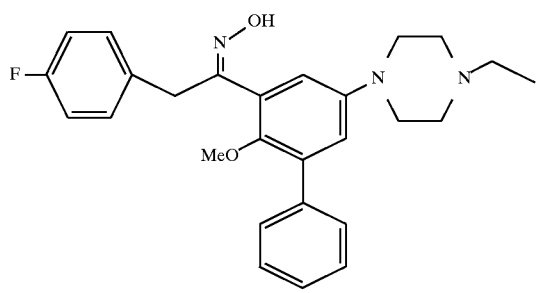

$^1$H-NMR(400 MHz, CDCl$_3$); δ(ppm) 7.55(2H, m), 7.4 (3H, m), 7.1(2H, m), 6.9(2H, m), 6.7(2H, m), 4.2(2H, s), 3.3(3H, s), 3.2(4H, m), 2.65(4H, m), 2.5(2H, q), 1.2(3H, t).

Example 99

1-Ethyl-4-{3-phenyl-4-methoxy-5-[1-fluoro-2-(2-pyridyl)ethyl]}phenylpiperazine

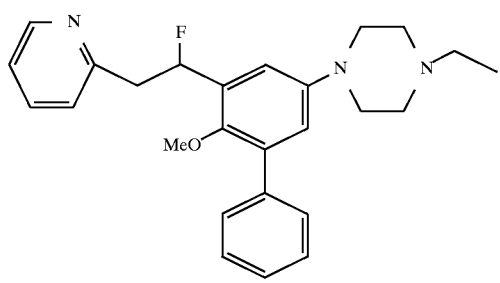

$^1$H-NMR(400 MHz, CDCl$_3$); δ(ppm) 8.6(1H, m), 7.6(3H, m), 7.4(2H, m), 7.35(1H, m), 7.25(1H, m), 7.15(1H, m), 7.05(1H, d), 6.9(1H, m), 6.25(1H, m), 3.4(2H, m), 3.3(3H, s), 3.2(4H, m), 2.6(4H, m), 2.5(2H, q), 1.15(3H, t).

Example 100

1-Ethyl-4-[3-phenyl-4-methoxy-5-(1-propenyl)]phenylpiperazine hydrochloride

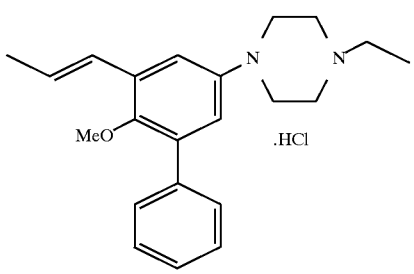

$^1$H-NMR(400 MHz, CDCl$_3$); δ(ppm) 7.95(1H, m), 7.6 (1H, m), 7.5(2H, m), 7.4(3H, m), 6.7(1H, d), 6.45(1H, m), 4.75(2H, t), 4.3(2H, m), 3.7(4H, m), 3.4(3H, s), 3.2(2H, m), 2.0(3H, d), 1.5(3H, t).

Example 101

1-Ethyl-4-[3-(3-fluorophenyl)-4-methoxy-5-propyl]phenylpiperazine

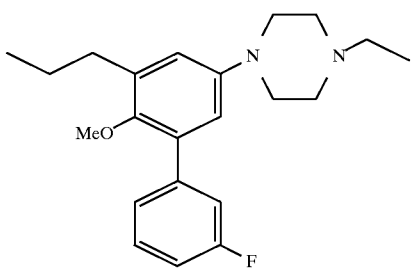

$^1$H-NMR(400 MHz, CDCl$_3$); δ(ppm) 7.4–7.2(3H, m), 7.0(1H, m), 6.75(2H, m), 3.3(3H, s), 3.2(4H, m), 2.6(6H, m), 2.45(2H, q), 1.7(2H, m), 1.1(3H, t), 1.0(3H, t).

Example 102

1-Ethyl-4-(3-phenyl-4-methoxy-5-hydroxymethyl)phenylpiperazine $^1$H-NMR(400 MHz, CDCl$_3$); δ(ppm) 7.6(2H, m), 7.4(3H, m), 6.9(1H, m), 6.8(1H, m), 4.7(2H, s), 3.35(3H, s), 3.2(4H, m), 2.65(4H, m), 2.5(2H, q), 1.2(3H, t).

Example 103

1-Ethyl-4-[3-phenyl-4-methoxy-5-(4-pyridyl)acetyl]phenylpiperazine

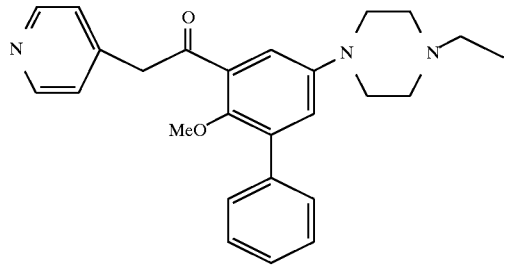

$^1$H-NMR(400 MHz, CDCl$_3$); δ(ppm) 8.6(2H, m), 7.6(2H, m), 7.4(3H, m), 7.2(2H, d), 7.05(2H, m), 4.4(2H, s), 3.35 (3H, s), 3.2(4H, m), 2.6(4H, m), 2.5(2H, q), 1.1(3H, t).

Example 104

1-Ethyl-4-(3-phenyl-4-methoxy-5-methanesulfinyl)phenylpiperazine

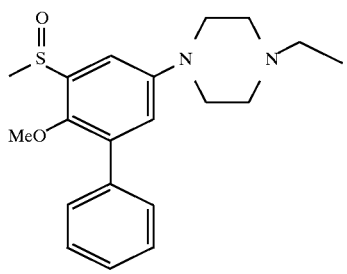

$^1$H-NMR(400 MHz, CDCl$_3$); δ(ppm) 7.6(2H, d), 7.4(4H, m), 6.95(1H, d), 3.35(3H, s), 3.3(4H,. m), 2.9(3H, s), 2.6(4H, m), 2.5(2H, q), 1.05(3H, t).

Example 105

1-Ethyl-4-(3-phenyl-4-methoxy-5-ethanesulfinyl)phenyl)phenylpiperazine

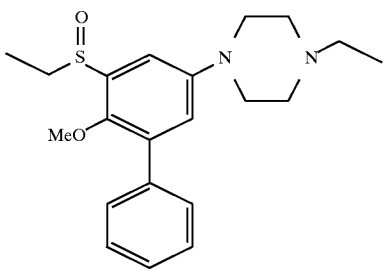

$^1$H-NMR(400 MHz, CDCl$_3$); δ(ppm) 7.6(2H, m), 7.4(3H, m), 7.3(1H, m), 6.95(1H, m), 3.35(3H, s), 3.3(4H, m), 3.15(2H, m), 2.9(2H, m), 2.6(4H, m), 2.5(2H, m), 1.3(3H, t), 1.15(3H, t).

Example 106

1-Ethyl-4-(3-phenyl-4-methoxy-5-formyl)phenylpiperazine

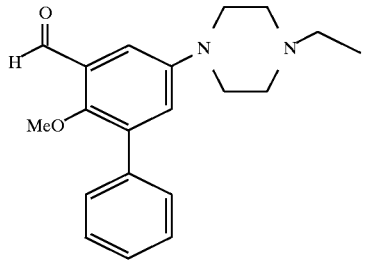

$^1$H-NMR(400 MHz, CDCl$_3$); δ(ppm) 10.43(1H, s), 7.34–7.6(5H, m), 7.17(2H, m), 3.4.6(3H, s), 3.40(4H, m), 2.81(4H, m), 2.66(2H, q), 1.25(3H, t).

Example 107

1-Ethyl-4-[3-phenyl-4-methoxy-5-(1,3-dioxan-2-yl)]phenylpiperazine

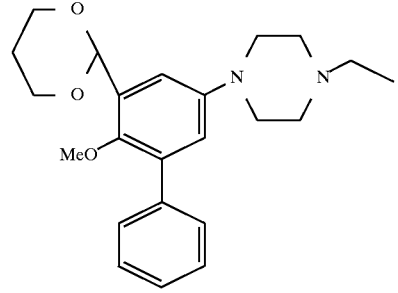

$^1$H-NMR(400 MHz, CDCl$_3$); δ(ppm) 7.3–7.54(5H, m), 7.18(1H, d), 6.89(1H, d), 5.85(1H, s), 4.26(2H, d-d), 4.04 (2H, d-t), 3.34(3H, s), 3.25(4H, m), 2.62(4H, m), 2.51(2H, q), 2.25(1H, m), 1.45(1H, m), 1.15(3H, t).

Example 108

1-Ethyl-4-(3-phenyl-4-methoxy-5-cyclopropaneacetyl)phenylpiperazine

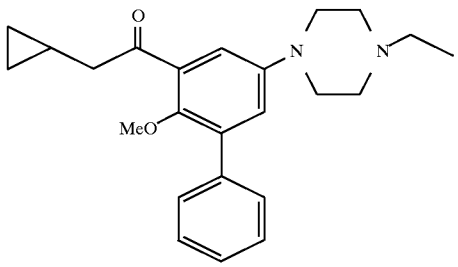

$^1$H-NMR(400 MHz, CDCl$_3$); δ(ppm) 7.6(2H, d), 7.4(3H, m), 7.0(2H, m), 5.9(1H, m), 5.1(2H, m), 3.35(3H, s), 3.2(4H, m), 3.15(2H, t), 2.6(4H, m), 2.45(4H, m), 1.1(3H, t).

Example 109

1-Ethyl-4-[3-phenyl-4-methoxy-5-(2-pyridylcarbonyl)]phenylpiperazine

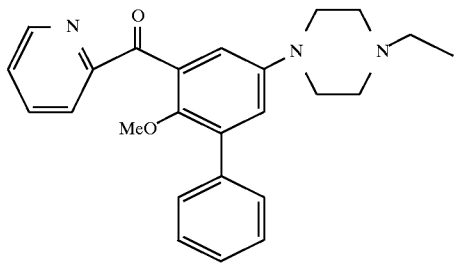

$^1$H-NMR(400 MHz, CDCl$_3$); δ(ppm) 8.7(1H, m), 8.05 (1H, d), 7.85(1H, m), 7.6(2H, m), 7.4(3H, m), 7.35(1H, m), 7.05(1H, m), 7.0(1H, m), 3.2(4H, m), 3.1(3H, s), 2.66(4H, m), 2.5(2H, q), 1.1(3H, t).

Example 110

1-Ethyl-4-[3-phenyl-4-methoxy-5-amino)phenylpiperazine

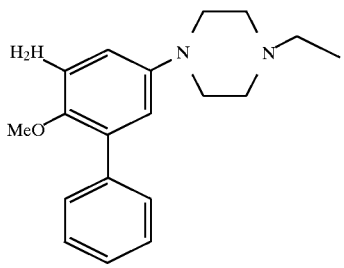

$^1$H-NMR(400 MHz, CDCl$_3$); δ(ppm) 7.6(2H, m), 7.4–7.3 (3H, m), 6.35(1H, m), 6.3(1H, m), 3.9(2H, b-s), 3.7(2H, q), 3.35(3H, s), 3.2(4H, m), 2.6(4H, m), 2.45(2H, q), 1.2(3H, t), 1.1(3H, t).

Example 111

1-Ethyl-4-[3-phenyl-4-methoxy-5-(2-ethoxycarbonylethyl)]phenylpiperazine

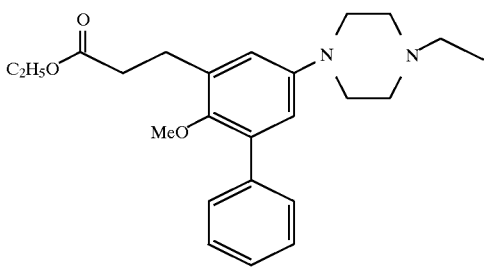

$^1$H-NMR(400 MHz, CDCl$_3$); δ(ppm) 7.3–7.59(5H, m), 6.78(2H, m), 4.14(2H, q), 3.30(3H, s), 3.21(4H, m), 2.97 (2H, t), 2.65(2H, t), 2.62(4H, m), 2.50(2H, q), 1.25(3H, t), 1.14(3H, t).

Example 112

1-Ethyl-4-[3-phenyl-4-methoxy-5-(2-pyridyl)hydroxymethyl]phenylpiperazine

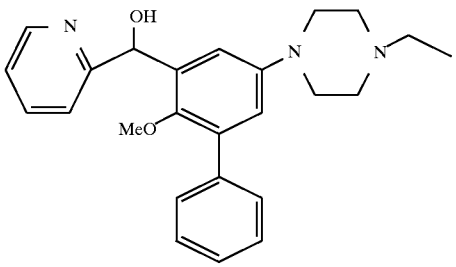

$^1$H-NMR(400 MHz, CDCl$_3$); δ(ppm) 8.6(1H, m), 7.65 (1H, t), 7.6(2H, m), 7.4(3H, m), 7.35(1H, m), 7.2(1H, m), 6.9(1H, m), 6.8(1H, m), 3.3(3H, s), 3.2(4H, m), 2.55(4H, m), 2.4(2H, q), 1.1(3H, t).

Example 113

1-Ethyl-4-(3-phenyl-5-propyl-6-methoxy)phenyl]phenylpiperazine hydrochloride

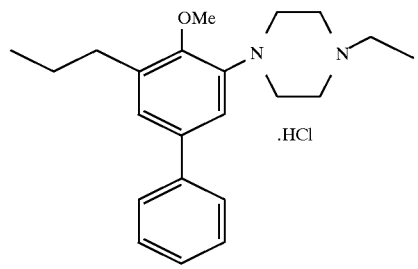

$^1$H-NMR (400 MHz, CDCl$_3$); δ(ppm) 13.5(1H, b-s), 8.05(1H, m), 7.6(2H, m), 7.5(1H, s), 4.8(2H, m), 4.4(1H, t), 4.8(2H, m), 4.4(2H, b-s), 4.2(3H, s), 3.8(2H, d), 3.6(2H, d), 3.25(2H, b-s), 2.8(2H, t), 1.75(2H, m), 1.6(3H, b-s), 1.0(3H, t).

Example 114

1-Ethyl-4-[3-phenyl-4-methoxy-5-(2-acetylethyl)]phenylpiperazine

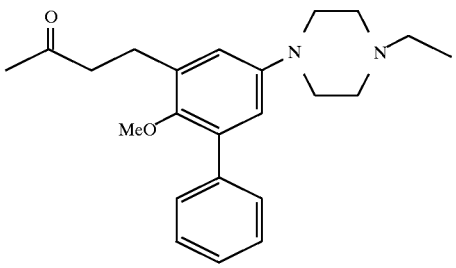

$^1$H-NMR(400 MHz, CDCl$_3$); δ(ppm) 7.30–7.59(5H, m), 6.75(2H, s), 3.28(3H, s), 3.19(4H, m), 2.89(2H, m), 2.82 (2H, m), 2.61(4H, m), 2.47(2H, q), 2.17(3H, s), 1.12(3H, t).

Example 115

1-Ethyl-4-{3-phenyl-4-methoxy-5-[1-(2-pyridylmethoxy)propyl]}phenylpiperazine

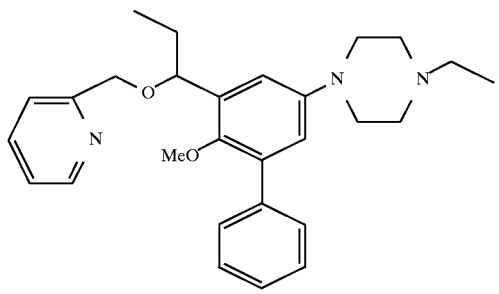

$^1$H-NMR(400 MHz, CDCl$_3$); δ(ppm) 8.7(1H, d), 8.2(1H, t), 7.85(1H, d), 7.6(1H, t), 7.5(2H, m), 7.4(1H, m), 7.35(1H, m), 7.1(1H, s), 6.8(1H, s), 4.8(3H, m), 3.6(6H, m), 3.25(3H, s), 3.15(2H, q), 3.0(2H, m), 1.9(2H, m), 1.5(3H, t), 1.0(3H, t).

Example 116

1-Ethyl-4-[3-(2-tolyl)-4-methoxy-5-propyl]phenylpiperazine

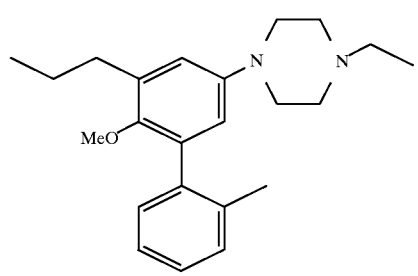

$^1$H-NMR(400 MHz, CDCl$_3$); δ(ppm) 7.18–7.25(4H, m), 6.78(1H, d), 6.59(1H, d), 3.24(3H, s), 3.18(4H, m), 2.58–2.62(6H, m), 2.48(2H, q), 2.19(3H, s), 1.66(2H, m), 1.13(3H, t), 0.99(3H, t).

Example 117

1-Ethyl-4-(3-phenyl-4-methoxy-5-propylamino)phenylpiperazine

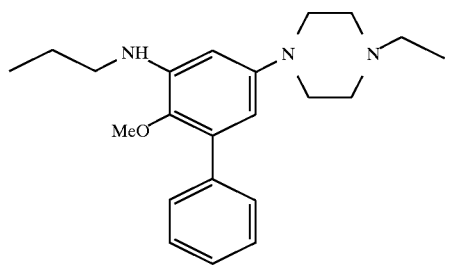

$^1$H-NMR(400 MHz, CDCl$_3$); δ(ppm) 7.6(2H, m), 7.4(2H, t), 7.3(1H, m), 6.25(1H, d), 6.2(1H, d), 4.3(1H, b-s), 3.3(3H, s), 3.2(4H, m), 3.1(2H, t), 2.6(4H, m), 2.5(2H, q), 1.7(2H, m), 1.1(3H, t), 1.0(3H, t).

Example 118

1-(3-Phenyl-4-hydroxy-5-phenylacetyl)phenylpiperazine

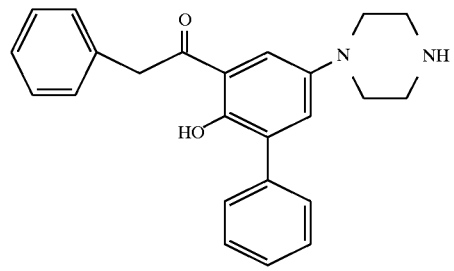

$^1$H-NMR(400 MHz, CDCl$_3$); δ (ppm) 7.55(2H, d), 7.4–7.25(5H, m), 4.35(2H, s), 3.2(8H, m).

Example 119

1-Ethyl-4-(3-phenyl-4-methoxy-5-benzylsulfinyl)phenylpiperazine

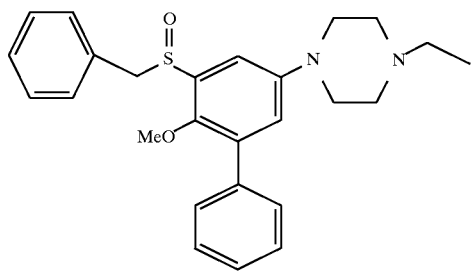

$^1$H-NMR(400 MHz, CDCl$_3$); δ(ppm) 7.6(2H, d), 7.5–7.35 (4H, m), 7.25(2H, m), 7.1(2H, m), 6.9(2H, m), 4.2(2H, q), 3.4(3H, s), 3.1(4H, m), 2.55(4H, m), 2.45(2H, q), 1.1(3H, t).

Example 120

1-Ethyl-4-(3-phenyl-4-methoxy-5-benzenesulfonylamino)phenylpiperazine

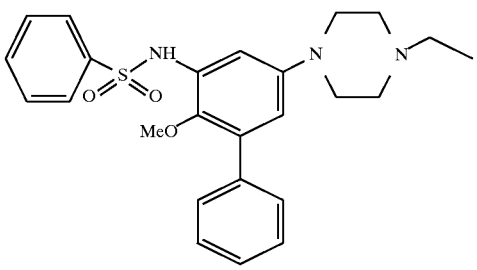

$^1$H-NMR(400 MHz, CDCl$_3$); δ(ppm) 7.8(2H, m), 7.6–7.3 (8H, m), 7.2(1H, d), 6.6(1H, d), 3.2(4H, m), 2.9(3H, s), 2.6(4H, m), 2.5(2H, q), 1.55(3H, t).

Example 121

1-Ethyl-4-{3-phenyl-4-methoxy-5-[1-fluoro-2-(4-pyridyl)ethyl]}phenylpiperazine

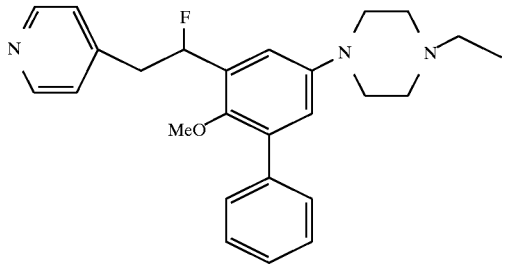

$^1$H-NMR(400 MHz, CDCl$_3$); δ(ppm) 8.5(2H, d), 7.6(2H, m), 7.4(2H, m), 7.35(1H, m), 7.2(2H, d), 6.85(2H, m), 5.95(1H, m), 3.2(3H, s), 3.15(4H, m), 2.6(4H, m), 2.4(2H, q), 1.1(3H, t).

Example 122

1-Ethyl-4-[3-phenyl-4-methoxy-5-(N-ethanesulfonyl-N-methylamino)]phenylpiperazine

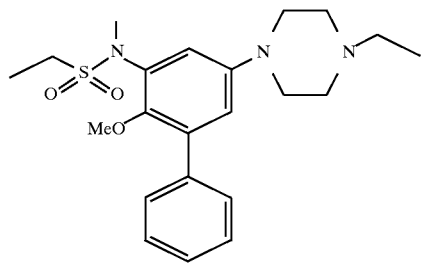

$^1$H-NMR(400 MHz, CDCl$_3$); δ(ppm) 7.6(1H, m), 7.5(2H, m), 7.4(3H, m), 6.8(1H, d), 3.7(2H, m), 3.4(3H, s), 3.2(4H, m), 2.6(4H, m), 2.5(2H, q), 1.25(3H, t), 1.15(3H, t).

Example 123

1-Ethyl-4-(3-phenyl-4-methoxy-5-ethylaminosulfonyl)phenylpiperazine

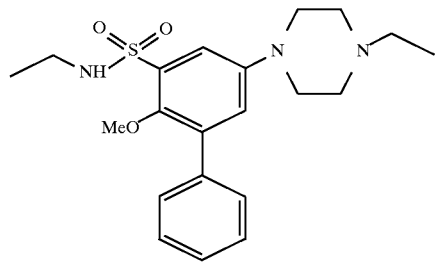

$^1$H-NMR(400 MHz, CDCl$_3$); δ(ppm) 7.55(2H, d), 7.4 (4H, m), 7.0(1H, d), 5.0(1H, t), 3.4(3H, s), 3.25(4H, m), 3.05(2H, q), 2.6(4H, m), 2.5(2H, q), 1.15(3H, t).

Example 124

1-Ethyl-4-(3-phenyl-4-methoxy-5-aminosulfonyl)phenylpiperazine

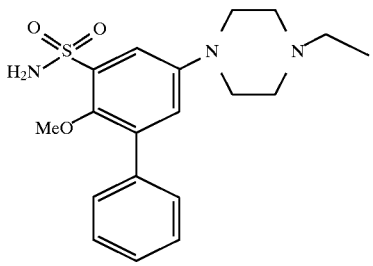

$^1$H-NMR(400 MHz, CDCl$_3$); δ(ppm) 7.55(2H, d), 7.4 (4H, m), 7.0(1H, d), 5.4(2H, s), 3.4(3H, s), 3.2(4H, m), 2.6(4H, m), 2.45(2H, q), 1.1(3H, s).

Example 125

1-(3-Phenyl-4-methoxy-5-phenylacetyl)phenylpiperazine

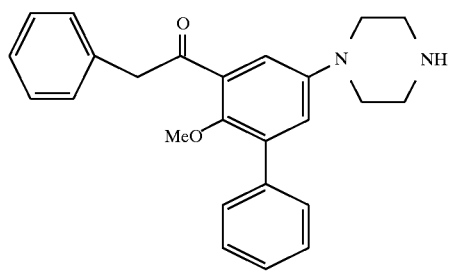

$^1$H-NMR(400 MHz, CDCl$_3$); δ(ppm) 7.6(2H, d), 7.5–7.2 (8H, m), 7.0(2H, s), 4.4(2H, s), 3.35(3H, s), 3.1(4H, m), 3.0(4H, m).

Example 126

1-Benzyl-4-(3-phenyl-4-methoxy-5-phenylacetyl)phenylpiperazine

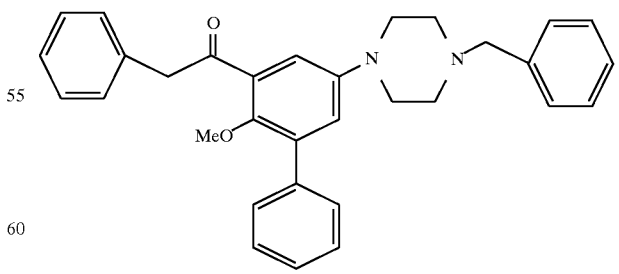

$^1$H-NMR(400 MHz, CDCl$_3$); δ(ppm) 7.6(2H, d), 7.45–7.2 (8H, m), 7.0(2H, s), 4.35(2H, s), 3.6(2H, s), 3.35(3H, s), 3.2(4H, m), 2.6(4H, m).

Example 127

1-Ethyl-4-[3-phenyl-4-chloro-5-(1-fluoropropyl)]phenylpiperazine

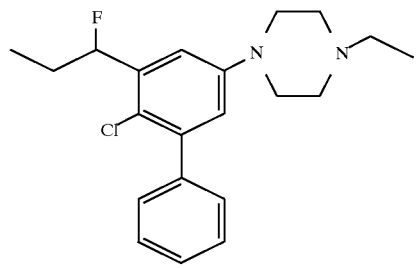

$^1$H-NMR(400 MHz, CDCl$_3$); δ(ppm) 7.4(5H, m), 7.05 (1H, d), 6.8(1H, d), 5.8(1H, m), 3.25(4H, m), 2.6(4H, m), 2.5(2H, q), 2.0(2H, m), 1.15(3H, t), 1.05(3H, t).

Example 128

1-(2-Hydroxyethyl)-4-(3-phenyl-4-methoxy-5-phenylacetyl)phenylpiperazine

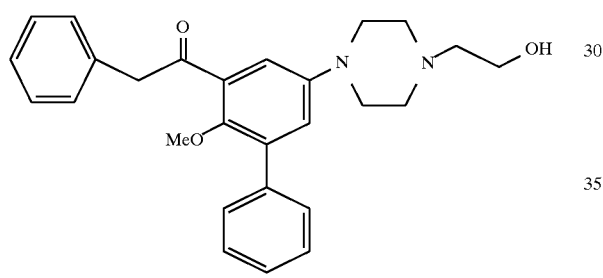

$^1$H-NMR (400 MHz, CDCl$_3$); δ(ppm) 7.6(2H, d), 7.5–7.2 (8H, m), 7.0(2H, s), 4.4(2H, s), 3.65(2H, t), 3.35(3H, s), 3.2(4H, m), 2.65(4H, m), 2.6(2H, t).

Example 129

1-Ethyl-4-[3-phenyl-5-(1-fluoropropyl)]phenylpiperazine

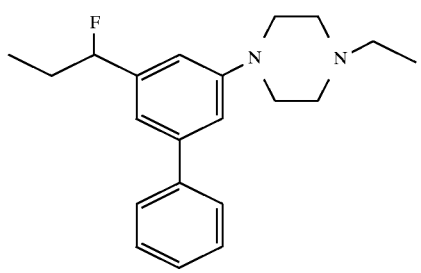

$^1$H-NMR (400 MHz, CDCl$_3$); δ(ppm) 7.6(2H, d), 7.4(2H, m), 7.35(1H, m), 7.05(1H, s), 6.9(1H, s), 5.4(1H, m), 3.3(4H, m), 2.6(4H, m), 2.5(2H, q), 2.0(2H, m), 1.15(3H, t), 1.0(3H, t).

Example 130

1-Ethyl-4-(3-phenyl-5-propionyl)phenylpiperazine

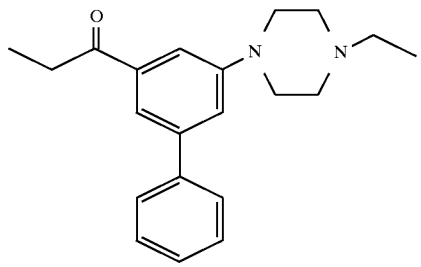

$^1$H-NMR(400 MHz, CDCl$_3$); δ(ppm) 7.6(2H, d), 7.6–7.3 (7H, m), 3.35(4H, m), 3.0(2H, q), 2.6(4H, m), 2.5(2H, q), 1.2(3H, t), 1.1(3H, t).

Example 131

1-Ethyl-4-[3-(2-tolyl)-4-chloro-5-(1-fluoropropyl)]phenylpiperazine

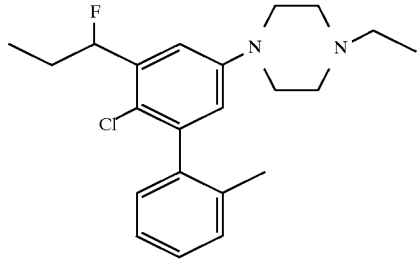

$^1$H-NMR(400 MHz, CDCl$_3$); δ(ppm) 12.9(1H, b-s), 7.4–7.2(3H, m), 7.1(2H, m), 6.8(1H, s), 5.8(1H, m), 3.8–3.6 (6H, m), 3.2(2H, b-s), 3.0(2H, b-s), 2.1(3H, d), 1.9(2H, m), 1.5(3H, t), 1.05(3H, t).

Example 132

1-Ethyl-4-[3-(2-methoxyphenyl)-4-methoxy-5-propyl]phenylpiperazine

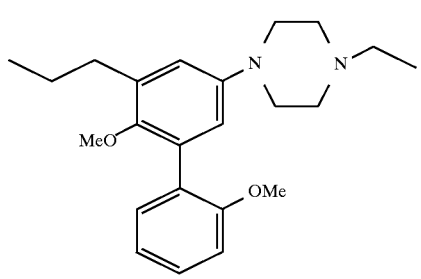

$^1$H-NMR(400 MHz, CDCl$_3$); δ(ppm) 7.3(2H, m), 7.0(2H, m), 6.75(2H, m), 3.8(3H, s), 3.3(3H, s), 3.2(4H, m), 2.6(6H, m), 2.45(2H, q), 1.7(2H, m), 1.15(3H, t), 1.0(3H, t).

Example 133

1-Ethyl-4-(3-phenyl-4-methoxy-5-ethanesulfonyl)phenylpiperazine

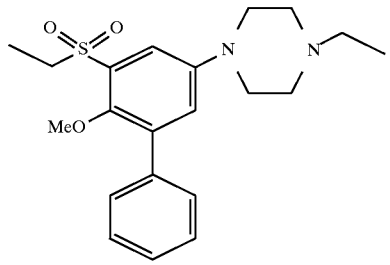

$^1$H-NMR(400 MHz, CDCl$_3$); δ(ppm) 7.6(2H, d), 7.4(4H, m), 7.1(1H, d), 3.5(2H, q), 3.4(3H, s), 3.25(4H, m), 2.6(4H, m), 2.5(2H, q) 1.3(3H, t), 1.1(3H, t).

Example 134

1-Ethyl-4-(3-phenyl-4-methoxy-5-dimethylaminosulfonyl)phenylpiperazine

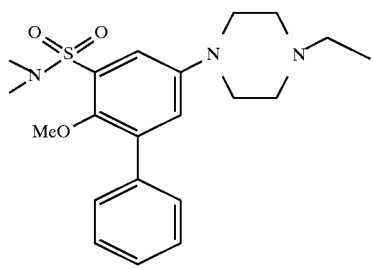

$^1$H-NMR(400 MHz, CDCl$_3$); δ(ppm) 7.6(2H, d), 7.5–7.3(4H, m), 7.0(1H, d), 3.4(3H, s), 3.2(4H, m), 2.95(6H, s), 2.6(4H, m), 2.5(2H, q), 1.15(3H, t).

Example 135

1-Ethyl-4-[3-phenyl-4-methoxy-5-(1-pyrrolidinylsulfonyl)]phenylpiperazine

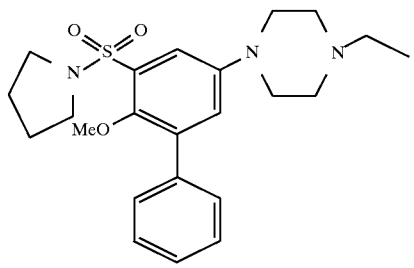

$^1$H-NMR(400 MHz, CDCl$_3$); δ(ppm) 7.55(2H, m), 7.4 (4H, m), 7.0(1H, d), 3.45(4H, m), 3.4(3H, s), 3.25(4H, m), 2.6(4H, m), 2.5(2H, q), 1.9(4H, m), 1.15(3H, t).

Example 136

1-Ethyl-4-[3-(2-tolyl)-4-chloro-5-(2,2,2-trifluoroethyl)sulfonylamino]phenylpiperazine

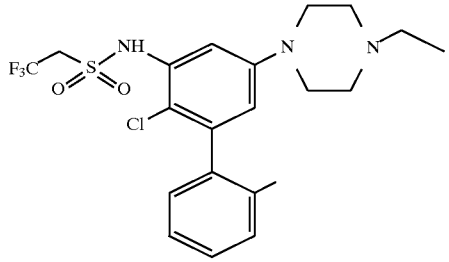

$^1$H-NMR(400 MHz, CDCl$_3$); δ(ppm) 7.4–7.2(4H, m), 7.1(1H, m), 6.6(1H, m), 5.1(1H, b-s), 3.85(2H, q), 3.2(4H, m), 2.65(4H, m), 2.6(2H, q), 2.1(3H, s), 1.2(3H, t).

Example 137

1-Ethyl-4-[3-(2-tolyl)-4-chloro-5-(4-fluorophenylsulfonylamino)]phenylpiperazine

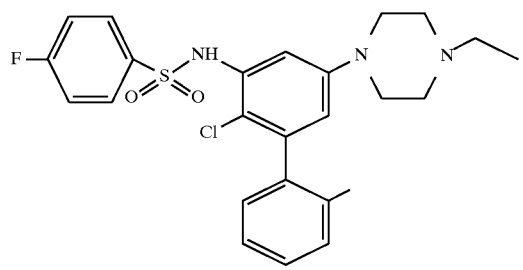

$^1$H-NMR(400 MHz, CDCl$_3$); δ(ppm) 7.8(2H, m), 7.3–7.1 (4H, m), 7.1(2H, m), 7.0(1H, d), 6.55(1H, s), 3.2(4H, m), 2.6(4H, m), 2.5(2H, q), 1.85(3H, s), 1.1(3H, t).

Example 138

1-Ethyl-4-[3-phenyl-4-chloro-5-(1-hydroxypropyl)]phenylpiperazine

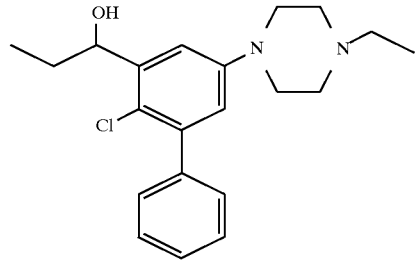

$^1$H-NMR(400 MHz, CDCl$_3$); δ(ppm) 7.27–7.43(5H, m), 7.16(1H, d), 6.62(1H, d), 5.06(1H, d-d), 3.12(2H, m), 2.95 (2H, m), 2.56(4H, m), 2.38–2.54(2H, m), 1.64–1.83(2H, m), 1.17(3H, t), 1.02(3H, t).

Example 139

1-Ethyl-4-(3-phenyl-4-chloro-5-ethanesulfonyl)phenylpiperazine

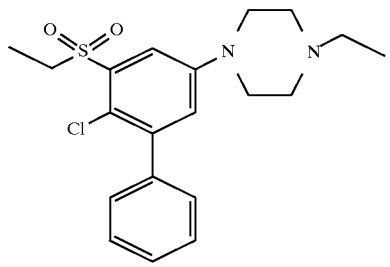

$^1$H-NMR (400 MHZ, CDCl$_3$); δ(ppm) 7.7(1H, d), 7.5–7.4 (5H, m), 7.0(1H, m), 3.5(2H, q), 3.3(4H, m), 2.6(4H, m), 2.5(2H, q), 1.35(3H, t), 1.15(3H, t).

Example 140

1-Ethyl-4-(3-phenyl-4-chloro-5-propionyl)phenylpiperazine

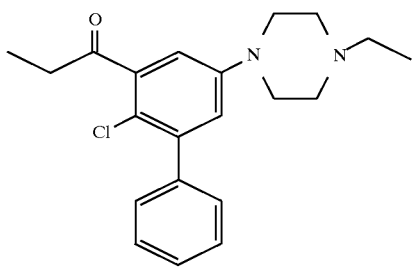

$^1$H-NMR(400 MHz, CDCl$_3$); δ(ppm) 7.30–7.43(5H, m ), 6.89(1H, d), 6.80(1H, d), 3.22(4H, m), 2.94(2H, q), 2.58(4H, m), 2.45(2H, q), 1.22(3H, t), 1.11(3H, t).

Example 141

1-Ethyl-4-[3-(2-tolyl)-4-chloro-5-(1-pyrrolidylsulfonyl)]phenylpiperazine

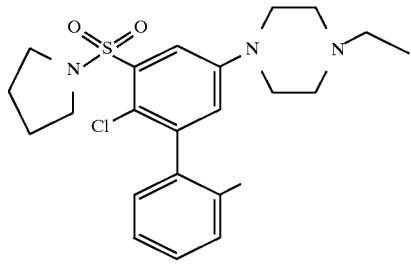

$^1$H-NMR(400 MHz, CDCl$_3$); δ(ppm) 7.7(1H, d), 7.4–7.2 (3H, m), 7.1(1H, d), 6.8(1H, m), 3.4(4H, m), 3.3(4H, m), 2.45(2H, q), 2.1(3H, s), 1.9(4H, m), 1.1(3H, t).

Example 142

1-Ethyl-4-{3-[2-(4-fluorotolyl)]-4chloro-5-(1-fluoropropyl)}phenylpiperazine

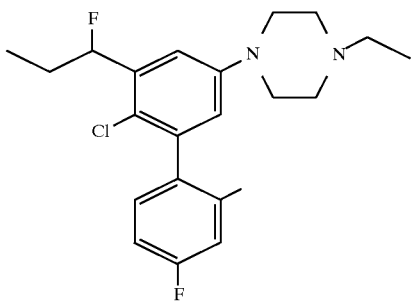

$^1$H-NMR(400 MHz, CDCl$_3$); δ(ppm) 7.1–7.0(2H, m), 7.0–6.9(2H, m), 6.7(1H, d), 5.8(2H, m), 3.2(4H, m), 2.6(4H, m), 2.45(2H, q), 1.9(2H, m), 2.1(3H, d), 1.1(3H, t), 1.05(3H, m).

Example 143

1-Ethyl-4-[3-(2-methoxyphenyl-4-chloro-5-(1-fluoropropyl)]phenylpiperazine

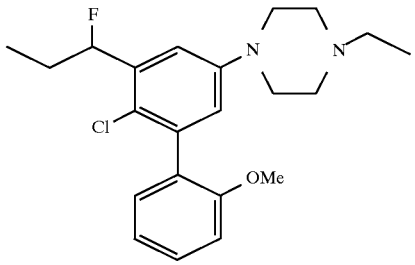

$^1$H-NMR(400 MHz, CDCl$_3$); δ(ppm) 7.4(1H, m), 7.2(1H, m), 7.0(3H, m), 6.8(1H, d), 5.8(1H, m), 3.8(3H, s), 3.25(4H, m), 2.6(4H, m), 2.5(2H, q), 1.15(3H, t), 1.05(3H, t).

Example 144

1-Ethyl-4-[3-(2,4-difluorophenyl)-4-chloro-5-(1-fluoropropyl)]phenylpiperazine

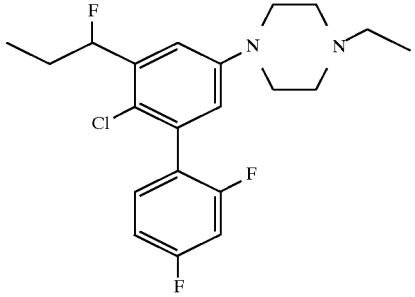

$^1$H-NMR(400 MHz, CDCl$_3$); δ(ppm) 7.2(1H, m), 7.1(1H, m), 7.0–6.9(2H, m), 6.8(1H, m), 5.8(1H, m), 3.2(4H, m), 2.6(4H, m), 2.45(2H, q), 1.9(2H, m), 1.1(3H, t), 1.05(3H, m).

Example 145

1-Ethyl-4-[3-(2-methoxymethylphenyl)-4-chloro-5-(1-fluoropropyl)]phenylpiperazine

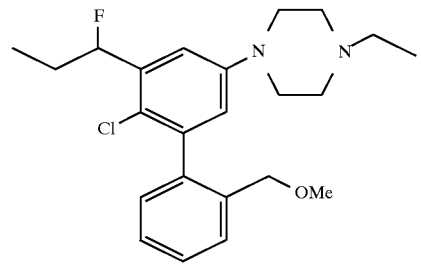

$^1$H-NMR(400 MHz, CDCl$_3$); δ(ppm) 7.55(1H, m), 7.4 (1H, m), 7.35(1H, m), 7.2(1H, m), 7.05(1H, m), 6.8(1H, m), 5.75(1H, m), 4.3–4.1(2H, m), 3.3(4H, m), 3.25(3H, d), 2.7(4H, m), 2.55(2H, m), 2.0(2H, m), 1.2(3H, t), 1.05(3H, t).

Example 146

1-Ethyl-4-{3-[2-(4-fluorotolyl)]-4-chloro-5-cyclopropaneaminosulfonyl}phenylpiperazine

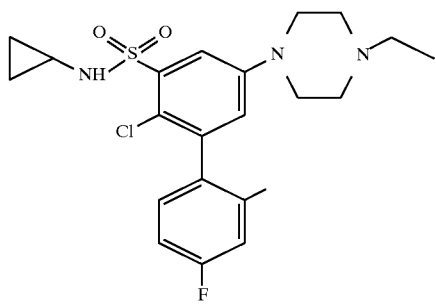

$^1$H-NMR(400 MHz, CDCl$_3$); δ(ppm) 7.75(1H, s), 7.1–6.8 (5H, m), 5.55(1H, s), 3.3(4H, m), 2.6(4H, m), 2.5(2H, q), 2.2(1H, m), 2.1(3H, s), 1.1(3H, t), 0.7–0.6(4H, m).

Example 147

1-Ethyl-4-[3-phenyl-4-chloro-5-(1-methylpropyl)]phenylpiperazine

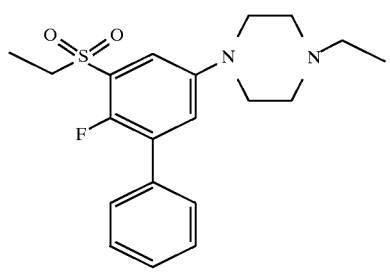

$^1$H-NMR(400 MHz, CDCl$_3$); δ(ppm) 7.4(5H, m), 6.69 (2H, d), 6.65(2H, d), 3.18–3.30(1H, m), 3.18(4H, m), 2.60 (4H, m), 2.48(2H, m), 1.17–1.92(2H, m), 1.2(3H, d), 1.12 (3H, t), 0.89(3H, t).

Example 148

1-Ethyl-4-{3-[2-(4-fluorotolyl)]-4-chloro-5-cyclopropylmethylsulfonyl}phenylpiperazine

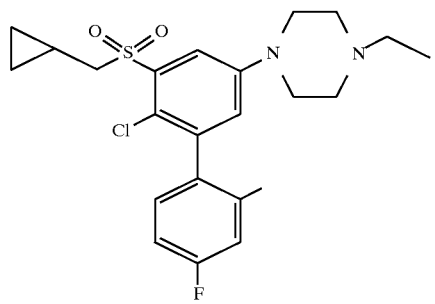

$^1$H-NMR(400 MHz, CDCl$_3$); δ(ppm) 7.75(1H, d), 7.05 (1H, m), 7.0–6.9(3H, m), 3.4(2H, d), 3.3(4H, m), 2.6(4H, m), 2.5(2H, q), 2.1(3H, s), 1.1(3H, t), 1.0(1H, m), 0.6(2H, m), 0.25(2H, m).

Example 149

1-Ethyl-4-(3-phenyl-4-fluoro-5-ethanesulfonyl)phenylpiperazine

NMR(CDCl$_3$) d; 7.55–7.4(5H, m), 7.2(1H, m), 3.35(2H, q), 3.25(4H, m), 2.6(4H, m), 2.5(2H, q), 1.3(3H, t), 1.1(3H, t).

Example 150

1-[3-(4-pyridyl)propyl]-4-[3-(2-tolyl)-4-chloro-5-(1-fluoropropyl)]phenylpiperazine

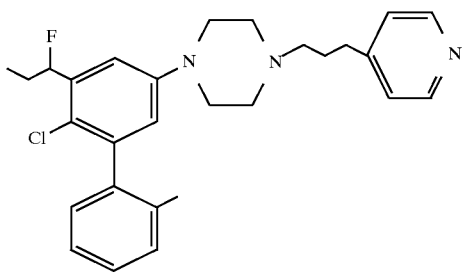

$^1$H-NMR(400 MHz, CDCl$_3$); δ(ppm) 8.48(2H, d), 7.20–7.32(4H, m), 7.1(2H, d), 7.02(1H, d), 6.71(1H, d), 5.78(1H, d-t), 3.22(4H, m), 2.68(2H, t), 2.60(4H, m), 2.41 (2H, t), 2.12(2H, q), 2.08(3H, d), 1.80–1.94(2H, m), 1.07 (3H, d-t).

Example 151

1-Propyl-4-[3-(2-tolyl)-4-chloro-5-(1-fluoropropyl)]phenylpiperazine

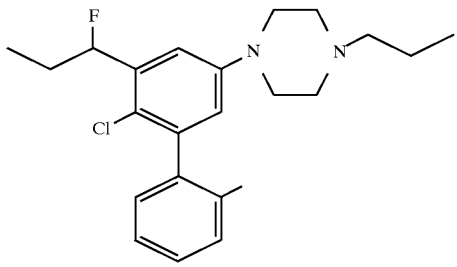

¹H-NMR(400 MHz, CDCl₃); δ(ppm) 7.1–7.28(4H, m), 7.02(1H, d), 6.70(1H, d), 5.78(1H, d-t), 3.22(4H, m), 2.59 (4H, m), 2.37(2H, d-d), 2.11(3H, d), 1.8–1.96(2H, m), 1.5–1.6(2H, m), 1.06(3H, d-t), 0.92(3H, t).

Example 152

1-Ethyl-4-[3-(2-hydroxymethylphenyl)-4-chloro-5-(1-fluoropropyl)]phenylpiperazine

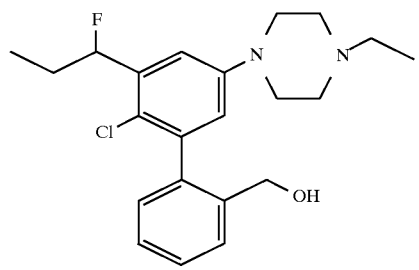

¹H-NMR(400 MHZ, CDCl₃); δ(ppm) 7.6(1H, m), 7.45 (1H, m), 7.35(1H, m), 7.2(1H, d), 7.05(1H, d), 6.75(1H, d), 5.75(1H, m), 4.5–4.4(2H, m), 3.25(4H, m), 2.6(4H, m), 2.5(2H, q), 1.9(2H, m), 1.15(3H, t), 1.05(3H, t).

Example 153

1-Ethyl-4-[3-(2-tolyl)-4-chloro-5-propanesulfonylamino]phenylpiperazine

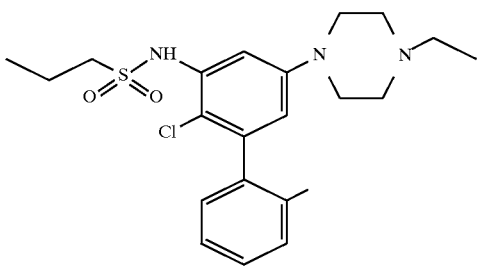

¹H-NMR(400 MHz, CDCl₃); δ(ppm) 7.4(1H, t), 7.4–7.2 (3H, m), 7.2–7.0(2H, m), 3.2(4H, m), 3.1(2H, d-d), 2.6(4H, m), 2.5(3H, s), 2.45(2H, q), 1.8(2H, m), 1.1(3H, t), 1.0(3H, t).

Example 154

1-Ethyl-4-[3-(2-tolyl)-4-chloro-5-dimethylaminosulfonyl]phenylpiperazine

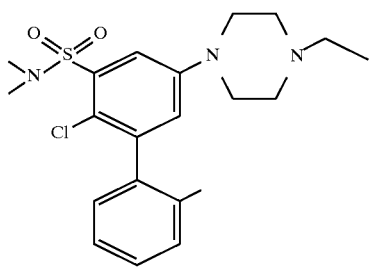

¹H-NMR(400 MHz, CDCl₃); δ(ppm) 7.65(1H, t), 7.3–7.2 (3H, m), 7.1(1H, m), 6.9(1H, d), 3.25(4H, m), 2.9(6H, s), 2.6(4H, m), 2.45(2H, q), 2.1(3H, s), 1.1(3H, t).

Example 155

1-Ethyl-4-[3-(2-tolyl-4-fluoro-5-methanesulfonyl]phenylpiperazine

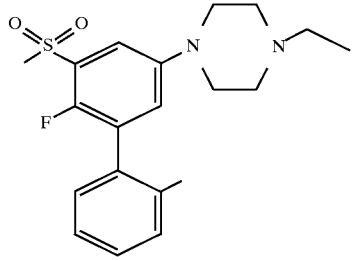

¹H-NMR(400 MHz, CDCl₃); δ(ppm) 7.4(1H, m), 7.4–7.2 (4H, m), 7.0(1H, m), 3.25(4H, m), 3.2(3H, s), 2.6(4H, m), 2.5(2H, q), 2.2(3H, s), 1.1(3H, t).

Example 156

1-Ethyl-4-[3-(2-chloro-4-fluorophenyl-4-chloro-5-(1-fluoropropyl)]phenylpiperazine

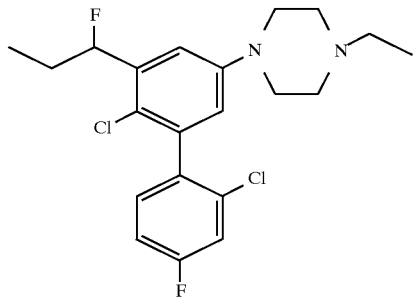

¹H-NMR(400 MHz, CDCl₃); δ(ppm) 7.4(2H, m), 7.0(2H, m), 6.7(1H, m), 5.8(1H, m), 3.2(4H, m), 2.6(4H, m), 2.45 (2H, q), 2.0(2H, m), 1.1(3H, t), 1.05(3H, m).

Example 157

1-Ethyl-4-[3-(2-tolyl)-4-chloro-5-(1ethylpropyl)]phenylpiperazine

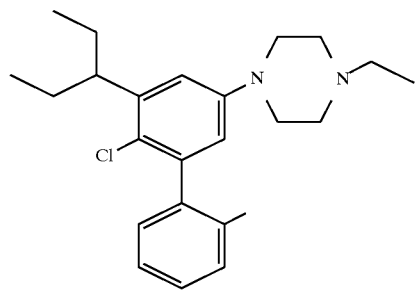

$^1$H-NMR(400 MHz, CDCl$_3$); δ(ppm) 7.06–7.24(4H, m), 6.74(1H, d), 6.61(1H, d), 3.20(4H, m), 3.15(1H, m), 2.60 (4H, m), 2.46(2H, q), 2.00(3H, s), 1.23(3H, t), 1.56–1.74 (4H, m), 0.78(3H, t), 0.76(3H, t).

Example 158

1-Ethyl-4-[3-(2-tolyl)-4-chloro-5-methanesulfonyl]phenylpiperazine

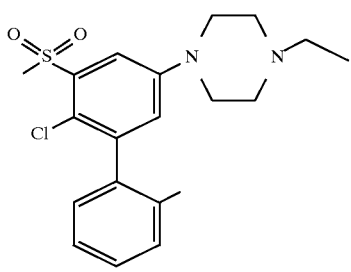

$^1$H-NMR(400 MHz, CDCl$_3$); δ(ppm) 7.7(1H, d), 7.3(3H, m), 7.1(1H, m), 6.95(1H, d), 3.3(3H, s), 3.3(4H, m), 2.6(4H, m), 2.45(2H, q), 2.1(3H, s), 1.1(3H, t).

Example 159

1-Ethyl-4-[3-(2-tolyl)-4-chloro-5-propanesulfonyl]phenylpiperazine

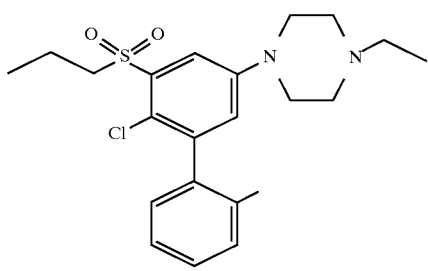

$^1$H-NMR(400 MHz, CDCl$_3$); δ(ppm) 7.75 (1H, m), 7.4–7.2 (3H, m), 7.1(1H, d), 6.95(1H, d), 3.4(2H, m), 3.3(4H, m), 2.6(4H, m), 2.45(2H, q), 2.1(3H, s), 1.8(2H, m), 1.1(3H, t), 1.0(3H, t).

Example 160

1-Ethyl-4-[3-(2-tolyl)-4-chloro-5-(1-fluoro-4-pentenyl)]phenylpiperazine

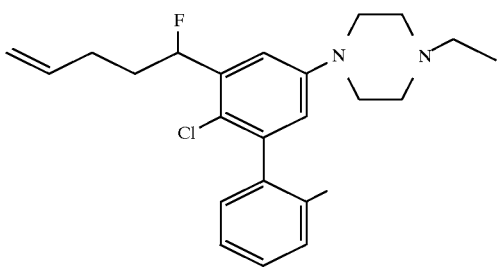

$^1$H-NMR(400 MHz, CDCl$_3$); δ(ppm) 7.3–7.2(4H, m), 7.15(1H, m), 7.05(1H, m), 5.9–5.8(1H, m), 5.1–5.0(2H, m), 3.2(4H, m), 2.6(4H, m), 2.45(2H, q), 2.3(2H, m), 2.1(3H, m), 2.0(2H, m), 1.1(3H, t).

Example 161

1-Ethyl-4-[3-(2-tolyl)-4-chloro-5-propylaminosulfonyl]phenylpiperazine

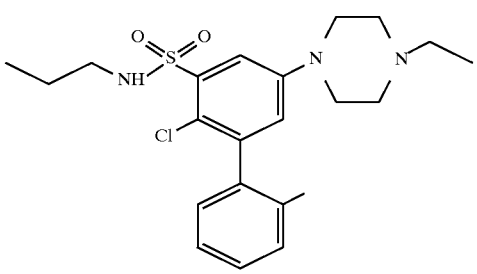

$^1$H-NMR(400 MHz, CDCl$_3$); δ(ppm) 7.75(1H, d), 7.4–7.2 (3H, m), 7.1(1H, d), 6.9(1H, d), 5.1(1H, t), 3.3(4H, m), 2.95(2H, q), 2.6(4H, m), 2.45(2H, q), 2.1(3H, s), 1.5(2H, m), 1.1(3H, t), 0.9(3H, t).

Example 162

1-Ethyl-4-[3-(2-tolyl)-4-chloro-5-ethanesulfonylamino]phenylpiperazine

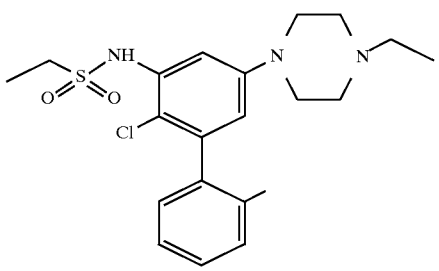

$^1$H-NMR(400 MHz, CDCl$_3$); δ(ppm) 7.7(1H, m), 7.45 (1H, m), 7.25(3H, m), 7.1(1H, m), 3.2(4H, m), 3.15(2H, q), 2.6(4H, m), 2.45(2H, q), 2.1(3H, s), 1.4(3H, t), 1.1(3H, t).

Example 163

1-Ethyl-4-[3-(2-chlorophenyl)-4-chloro-5-(2,2,2-trifluoroethylsulfonylamino]phenylpiperazine

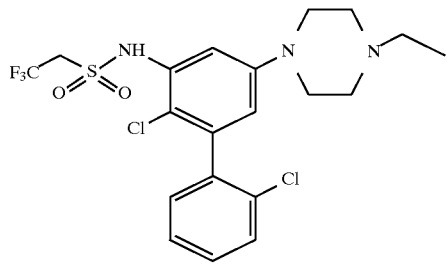

¹H-NMR(400 MHz, CDCl₃); δ(ppm) 7.7(2H, m), 7.5(2H, m), 7.4(2H, m), 6.65(1H, d), 3.9(2H, q), 3.2(4H, m), 2.6(4H, m), 2.5(2H, q), 1.1(3H, t).

Example 164

1-Ethyl-4-[3-(2-tolyl-4-cyano-5-(1-fluoropropyl)]phenylpiperazine

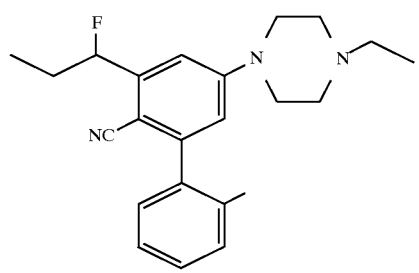

¹H-NMR(400 MHz, CDCl₃); δ(ppm) 7.3–7.2(4H, m), 7.0(1H, m), 6.65(1H, d), 5.75(1H, m), 3.4(4H, m), 2.6(4H, m), 2.45(2H, q), 2.2(3H, d), 2.0(2H, m), 1.1(3H, t), 1.05(3H, t).

Example 165

1-Ethyl-4-[3-(2-tolyl)-4-chloro-5-(3-chloropropyl)sulfonylamino]phenylpiperazine

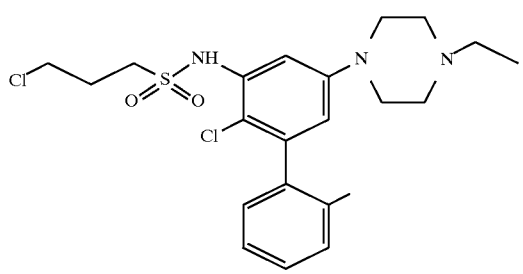

¹H-NMR(400 MHz, CDCl₃); δ(ppm) 7.7(2H, m), 7.55(1H, m), 7.45(2H, m), 7.3(1H, m), 3.6(2H, t), 3.2(4H, m), 2.6(4H, m), 2.45(2H, m), 2.3(2H, m), 2.1(3H, s), 1.1(3H, t).

Example 166

1-Ethyl-4-[3-(2-tolyl)-4-chloro-5-phenylaminosulfonyl]phenylpiperazine

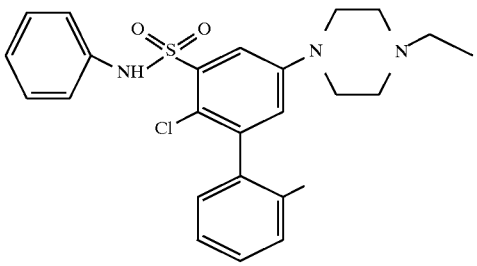

¹H-NMR(400 MHz, CDCl₃); δ(ppm) 7.55(1H, d), 7.4–7.0 (9H, m), 6.8(1H, d), 3.2(4H, m), 2.55(4H, m), 2.4(2H, q), 2.0(3H, s), 1.1(3H, t).

Example 167

1-Ethyl-4-[3-(2-tolyl)-4-chloro-5-benzyloxymethyl]phenylpiperazine

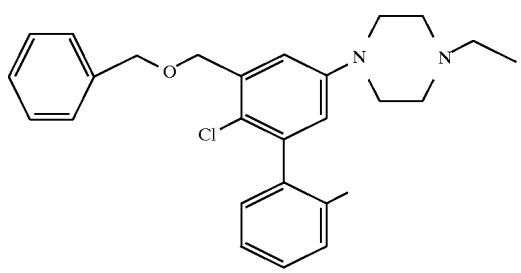

¹H-NMR(400 MHz, CDCl₃); δ(ppm) 7.65(1H, m), 7.6–7.1(9H, m), 6.7(1H, d), 4.65(2H, s), 3.2(4H, m), 2.6(4H, m), 2.45(2H, q), 2.1(3H, s), 1.1(3H, t).

Example 168

1-Ethyl-4-[3-(2-tolyl)-4-chloro-5-propoxymethyl]phenylpiperazine

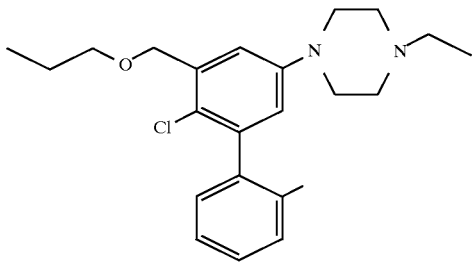

¹H-NMR(400 MHz, CDCl₃); δ(ppm) 7.65(1H, m), 7.45 (1H, m), 7.3–7.2(2H, m), 7.1(1H, m), 6.7(1H, d), 4.6(2H, s), 3.6(2H, t), 3.2(4H, m), 2.6(4H, m), 2.45(2H, q), 2.1(3H, s), 1.7(2H, m), 1.1(3H, t), 1.0(3H, t).

Example 169

1-Ethyl-4-[3-(2-tolyl)-4-chloro-5-(4-pyridyl)methoxymethyl]phenylpiperazine

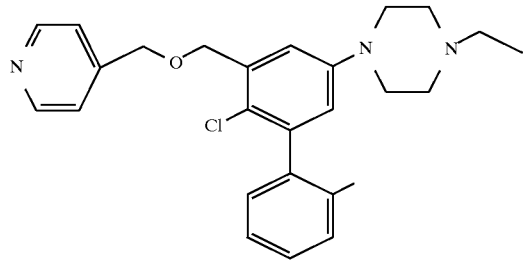

$^1$H-NMR(400 MHz, CDCl$_3$); δ(ppm) 8.6(2H, m), 7.4–7.2 (5H, m), 7.15(2H, m), 6.75(1H, d), 4.71(2H, s), 4.70(2H, s), 3.2(4H, m), 2.6(4H, m), 2.45(2H, q), 2.1(3H, s), 1.1(3H, t).

Example 170

1-Ethyl-4-(3-phenyl-4-methoxy-5-propanesulfonyl)phenylpiperazine

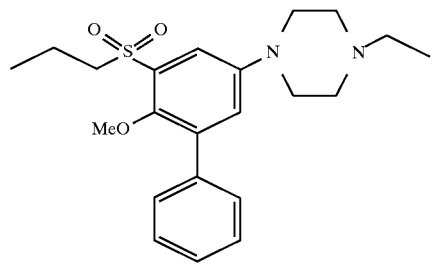

$^1$H-NMR(400 MHz, CDCl$_3$); δ(ppm) 7.6(1H, d), 7.4(4H, m), 7.1(1H, m), 3.45(2H, m), 3.4(3H, s), 3.25(4H, m), 2.6(4H, m), 2.5(2H, q), 1.8(2H, m), 1.15(3H, t), 1.0(3H, t).

Example 171

1-Ethyl-4-(3-phenyl-4-methoxy-5-butanesulfonyl)phenylpiperazine

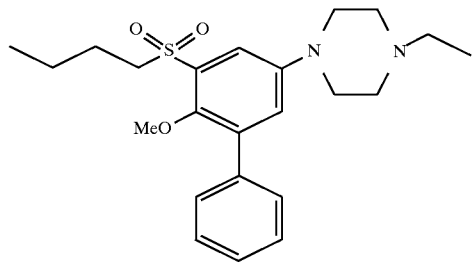

$^1$H-NMR(400 MHz, CDCl$_3$); δ(ppm) 7.55(1H, d), 7.4 (4H, m), 7.1(1H, d), 3.45(2H, m), 3.4(3H, s), 3.2(4H, m), 2.6(4H, m), 2.5(2H, q), 1.75(2H, m), 1.4(2H, m), 1.1(3H, t), 0.95(3H, t).

Example 172

1-Ethyl-4-[3-phenyl-4-methoxy-5-(2-fluoroethane)sulfonyl]phenylpiperazine

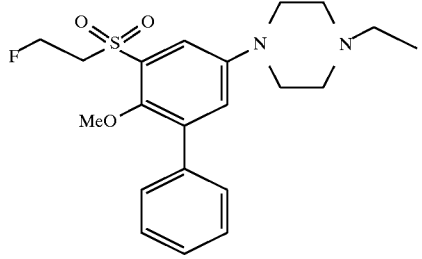

$^1$H-NMR(400 MHz, CDCl$_3$); δ(ppm) 7.55(1H, d), 7.4 (4H, m), 7.1(1H, m), 4.9(1H, t), 4.8(1H, t), 3.95(1H, t), 3.85(1H, t), 3.4(3H, s), 3.25(4H, m), 2.6(4H, m), 2.5(2H, q), 1.1(3H, t).

Example 173

1-Ethyl-4-[3-(2-tolyl)-4-chloro-5-ethoxymethyl]phenylpiperazine

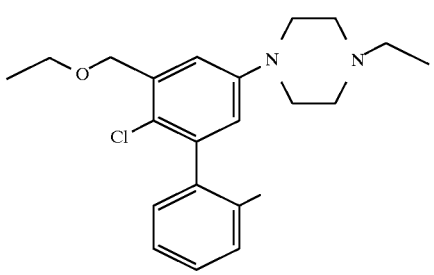

$^1$H-NMR(400 MHz, CDCl$_3$); δ(ppm) 7.7(1H, m), 7.45 (1H, m), 7.25(1H, m), 7.1(2H, m), 6.7(1H, m), 4.6(2H, s), 3.65(2H, q), 3.2(4H, m), 2.6(4H, m), 2.45(2H, q), 2.1(3H, s), 1.3(3H, t), 1.1(3H, t).

Example 174

1-Methyl-4-[3-(2-tolyl)-4-chloro-5-(1-hydroxybutyl)]phenylpiperazine

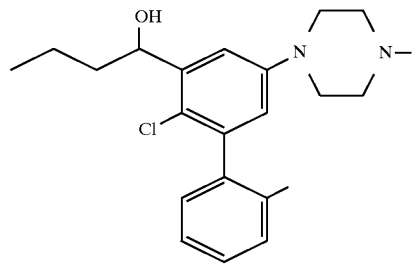

$^1$H-NMR(400 MHz, CDCl$_3$); δ(ppm) 7.3–7.1(5H, m), 6.65(1H, m), 5.15(1H, m), 3.2(4H, m), 2.6(4H, m), 2.35(3H, s), 2.1(3H, d), 1.8–1.4(4H, m), 1.0(3H, t).

Example 175

1-Ethyl-4-[3-(2-tolyl)-4-chloro-5-allyloxymethyl]phenylpiperazine

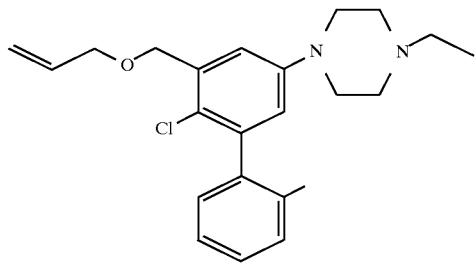

$^1$H-NMR(400 MHz, CDCl$_3$); δ(ppm) 7.25(3H, m), 7.1 (2H, m), 6.7(1H, d), 6.0(1H, m), 5.3(2H, m), 4.6(2H, s), 4.2(2H, m), 3.2(4H, m), 2.6(4H, m), 2.45(2H, q), 2.1(3H, s), 1.1(3H, t).

Example 176

1-Ethyl-4-[3-(2-tolyl)-4-chloro-5-cyclopropylmethoxymethyl]phenylpiperazine

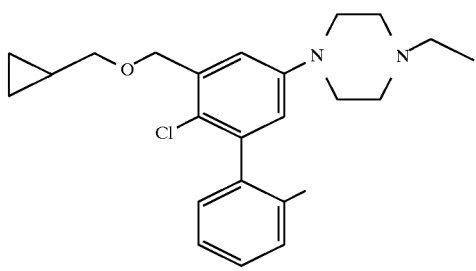

$^1$H-NMR(400 MHz, CDCl$_3$); δ(ppm) 7.25(3H, m), 7.1 (2H, m), 6.7(1H, d), 4.6(2H, s), 3.4(2H, d), 3.2(4H, m), 2.6(4H, m), 2.45(2H, q), 2.1(3H, s), 1.25(1H, m), 1.1(3H, t), 0.6(2H, m), 0.25(2H, m).

Example 177

1-Ethyl-4-[3-(2-tolyl)-4-chloro-5-(1-pyrrolidinyl)]phenylpiperazine

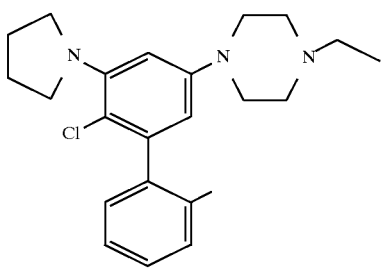

$^1$H-NMR(400 MHz, CDCl$_3$); δ(ppm) 7.18–7.28(4H, m), 6.21(1H, d), 6.10(1H, d), 3.51(4H, m), 3.26(4H, m), 2.61 (1H, d), 2.48(2H, q), 2.30(3H, s), 1.99(4H, m), 1.14(3H, t).

Example 178

1-Methyl-4-[3-(2-chlorophenyl)-4-chloro-5-(1-fluorobutyl)]phenylpiperazine

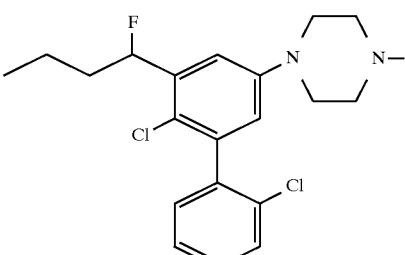

$^1$H-NMR(400 MHz, CDCl$_3$); δ(ppm) 7.45(1H, m), 7.3 (3H, m), 7.1(1H, d), 6.75(1H, d), 5.5(1H, m), 3.2(4H, m), 2.6(4H, m), 2.35(3H, s), 1.9(2H, m), 1.6(2H, m), 1.0(3H, t).

Example 179

1-Methyl-4-[3-(2-chlorophenyl)-4-chloro-5-benzylsulfonylamino]phenylpiperazine

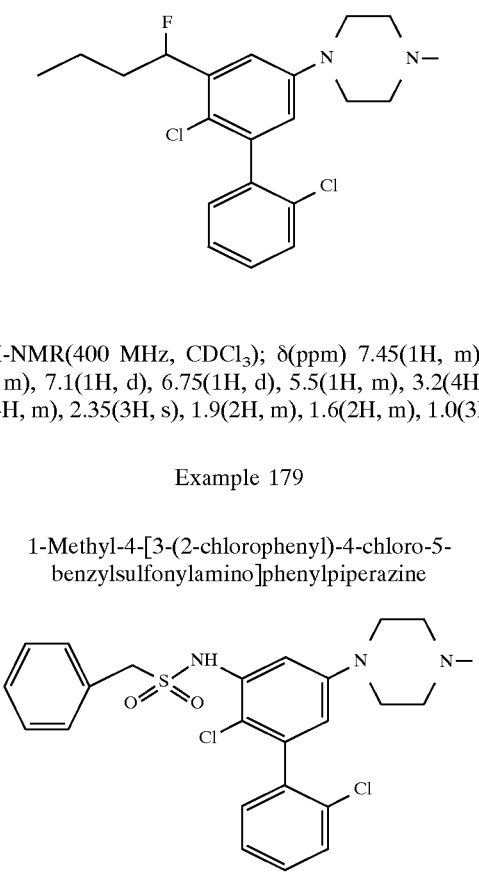

$^1$H-NMR(400 MHz, CDCl$_3$); δ(ppm) 7.5(1H, m), 7.4(5H, m), 7.25(4H, m), 6.6(1H, d), 4.4(2H, d-d), 3.2(4H, m), 2.6(4H, m), 2.4(3H, s).

Example 180

1-Methyl-4-[3-(2-chlorophenyl)-4-chloro-5-propanesulfonyl]phenylpiperazine

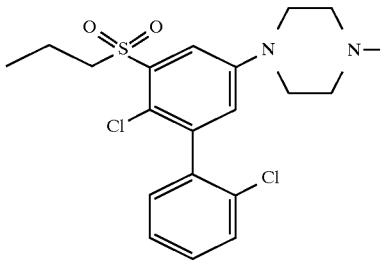

$^1$H-NMR(400 MHz, CDCl$_3$); δ(ppm) 7.7(1H, d), 7.5(1H, m), 7.4(2H, m), 7.25(1H, m), 7.0(1H, d), 3.5–3.4(2H, m), 3.3(4H, m), 2.6(4H, m), 2.4(3H, s). 1.8(2H, m), 1.6(3H, s), 1.0(3H, t).

Example 181

1-Ethyl-4-{3-phenyl-4-methoxy-5-[3-(4-fluorophenoxy)propane]sulfonyl}phenylpiperazine

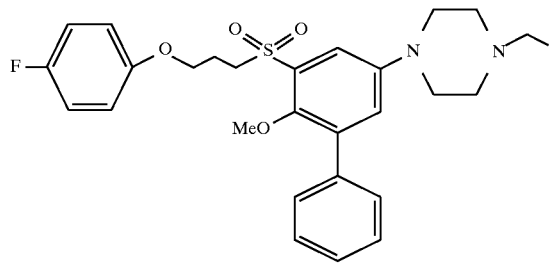

¹H-NMR(400 MHz, CDCl₃); δ(ppm) 7.55(2H, m), 7.4 (3H, m), 7.1(1H, d), 7.0(2H, m), 6.8(2H, m), 4.0(2H, t), 3.7(2H, d-d), 3.4(3H, s), 3.25(4H, m), 2.6(4H, m), 2.5(2H, q), 2.25(2H, m), 1.1(3H, t).

Example 182

1-Methyl-4-[3-(2-chlorophenyl)-4-chloro-5-isopropylsulfonylamino]phenylpiperazine

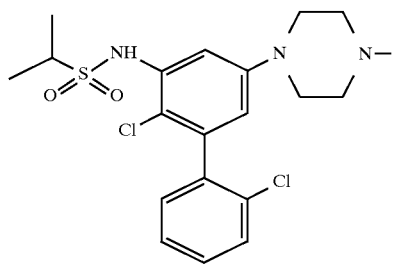

¹H-NMR(400 MHz, CDCl₃); δ(ppm) 7.41–7.46(2H, m), 7.30–7.38(2H, m), 7.24(1H, m), 6.60(1H, d), 3.24(1H, m), 3.21(4H, m), 2.57(4H, m), 2.35(3H, s), 1.96(6H, d).

Example 183

1-Ethyl-4-[3-phenyl-4-methoxy-5-(2-cyanoethylsulfonyl)]phenylpiperazine

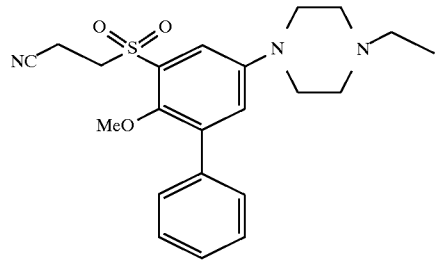

¹H-NMR(400 MHz, CDCl₃); δ(ppm) 7.6(2H, m), 7.5–7.4 (4H, m), 7.15(1H, d), 3.8(2H, t), 3.4(3H, s), 3.25(4H, m), 2.85(2H, t), 2.6(4H, m), 2.5(2H, q), 1.15(3H, t).

Example 184

1-Ethyl-4-(3-phenyl-4-chloro-5-propanesulfonylamino)phenylpiperazine

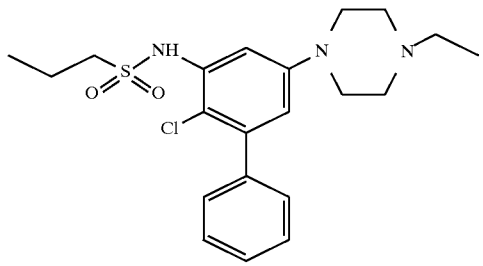

¹H-NMR(400 MHz, CDCl₃); δ(ppm) 7.36–7.48(5H, m), 7.24(1H, d), 6.65(1H, d), 3.26(4H, m), 3.10(2H, m), 2.58 (4H, m), 2.46(2H, q), 1.82–1.90(2H, m), 1.12(3H, t), 1.02 (3H, t).

Example 185

1-Ethyl-4-[3-(2-tolyl)-4-chloro-5-difluoromethyl]phenylpiperazine

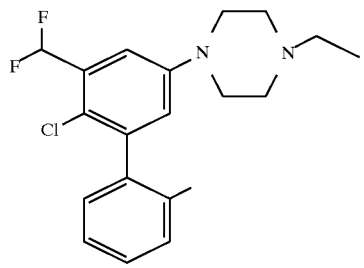

¹H-NMR(400 MHz, CDCl₃); δ(ppm) 7.4–7.2(4H, m), 7.1(1H, m), 6.85(1H, m), 3.25(4H, m), 2.6(4H, m), 2.45(2H, q), 2.1(3H, s), 1.1(3H, t).

Example 186

1-Ethyl-4-[3-phenyl-4-methoxy-5-(1,1-difluoropropyl)]phenylpiperazine

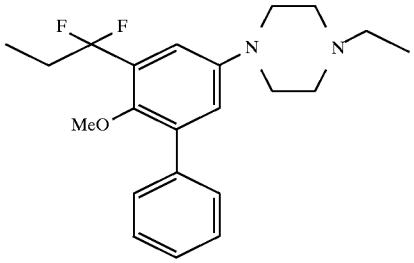

¹H-NMR(400 MHz, CDCl₃); δ(ppm) 7.6(2H, m), 7.4(3H, m), 7.05(1H, d), 6.95(1H, d), 3.25(3H, s), 3.2(4H, m), 2.6(4H, m), 2.5(2H, q), 2.4(2H, m), 1.15(3H, t), 1.0(3H, t).

Example 187

1-Ethyl-4-[3-(4-methoxyphenyl)-4-chloro-5-propanesulfonylamino]phenylpiperazine

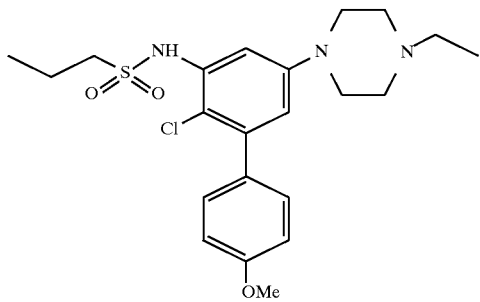

¹H-NMR(400 MHz, CDCl₃); δ(ppm) 7.35(2H, m), 7.25 (1H, m), 7.0(2H, m), 6.65(1H, m), 3.85(3H, s), 3.25(4H, m), 3.1(2H, m), 2.6(4H, m), 2.45(2H, q), 1.85(2H, m), 1.1(3H, t), 1.0(3H, t).

Example 188

1-Methyl-4-[3-(2-chlorophenyl)-4-chloro-5-methanesulfonylamino]phenylpiperazine

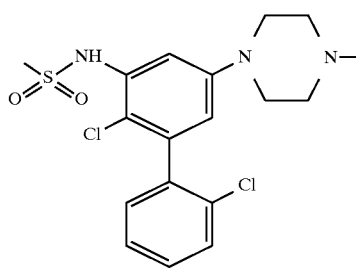

¹H-NMR(400 MHz, CDCl₃); δ(ppm) 7.23–7.48(5H, m), 6.62(1H, d), 3.24(4H, m), 3.02(3H, s), 2.54(4H, m), 2.34 (3H, s).

Example 189

1-Ethyl-4-[3-(2,4-dichlorophenyl)-4-chloro-5-propanesulfonylamino]phenylpiperazine

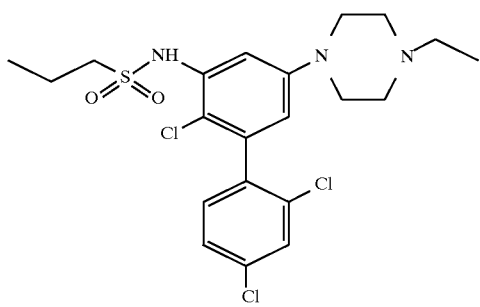

¹H-NMR(400 MHz, CDCl₃); δ(ppm) 7.7(2H, m), 7.5(2H, m), 7.3(1H, m), 3.25(4H, m), 3.1(2H, m), 2.6(4H, m), 2.45(2H, q), 1.85(2H, m), 1.1(3H, t), 1.0(3H, t).

Example 190

1-Ethyl-4-[3-(2-tolyl)-4-chloro-5-1,3-dithian-2-yl)phenylpiperazine

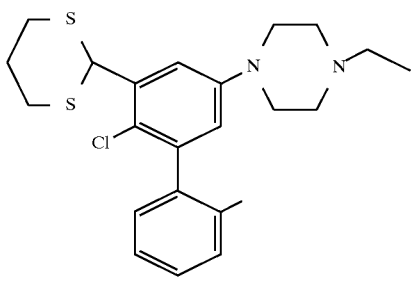

¹H-NMR(400 MHz, CDCl₃); δ(ppm) 7.45(2H, d), 7.3–7.2 (3H, m), 7.15(1H, d), 6.7(1H, m), 6.1(1H, s), 3.5–3.3(4H, m), 3.2(4H, m), 2.6(4H, m), 2.1(3H, s), 1.1(3H, t).

Example 191

1-Ethyl-4-[3-phenyl-4-chloro-5-propanedithio)]phenylpiperazine

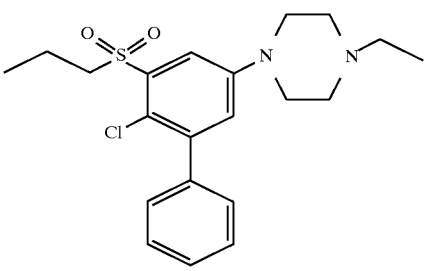

¹H-NMR(400 MHz, CDCl₃); δ(ppm) 7.7(2H, m), 7.5–7.4 (4H, m), 7.0(1H, d), 3.4(2H, m), 3.3(4H, m), 2.6(4H, m), 2.45(2H, q), 1.8(2H, m), 1.15(3H, t), 1.0(3H, t).

Example 192

1-Ethyl-4-[3-(2-tolyl)-4-chloro-5-propanesulfonylaminomethyl]phenylpiperazine

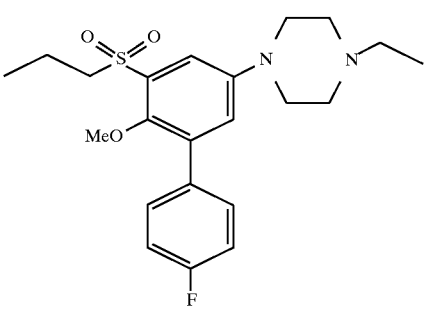

¹H-NMR(400 MHz, CDCl₃); δ(ppm) 7.65(2H, m), 7.45 (2H, m), 7.1(1H, m), 6.6(1H, d), 3.2(4H, m), 3.1(2H, m), 2.6(4H, m), 2.45(2H, q), 2.1(3H, s), 1.85(2H, m), 1.1(3H, t), 1.0(3H, t).

Example 193

1-Methyl-4-[3-(4-fluorophenyl)-4-methoxy-5-propanesulfonyl]phenylpiperazine

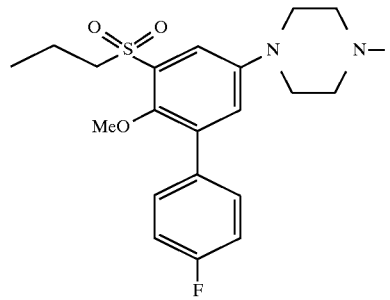

¹H-NMR(400 MHz, CDCl₃); δ(ppm) 7.55(2H, m), 7.4 (1H, d), 7.2(2H, m), 7.05(1H, d), 3.4(2H, m), 3.4(3H, s), 3.25(4H, m), 2.6(4H, m), 2.4(3H, s), 1.8(2H, m), 1.05(3H, t).

Example 194

1-Ethyl-4-[3-(2-ethylphenyl)-4-chloro-5-propanesulfonylamino]phenylpiperazine

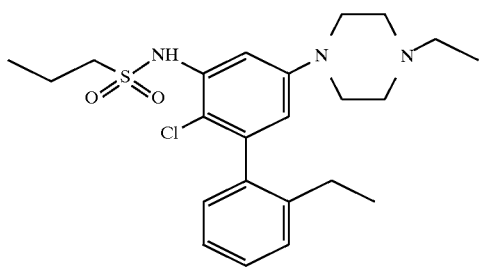

¹H-NMR(400 MHz, CDCl₃); δ(ppm) 7.4–7.2(4H, m), 7.1(1H, d), 6.6(1H, d), 3.25(4H, m), 3.1(2H, m), 2.6(4H, m), 2.5–2.3(4H, m), 1.85(2H, m), 1.2–1.0(9H, m).

Example 195

1-(2-Hydroxyethyl)-4-[3-(4-fluorophenyl)-4-methoxy-5-ethanesulfonyl]phenylpiperazine

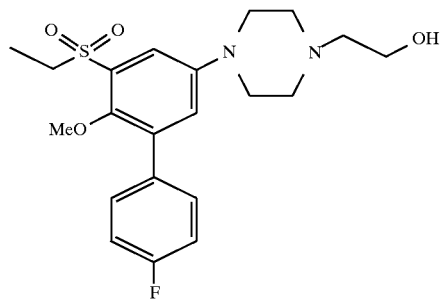

¹H-NMR(400 MHz, CDCl₃); δ(ppm) 7.55(2H, m), 7.4 (1H, d), 7.2(2H, m), 7.05(1H, d), 3.7(2H, t), 3.5(2H, q), 3.4(3H, s), 3.2(4H, m), 2.7(4H, m), 2.6(2H, t), 1.3(3H, t).

Example 196

1-Ethyl-4-[3-(2-formylphenyl)-4-chloro-5-propanesulfonylamino]phenylpiperazine

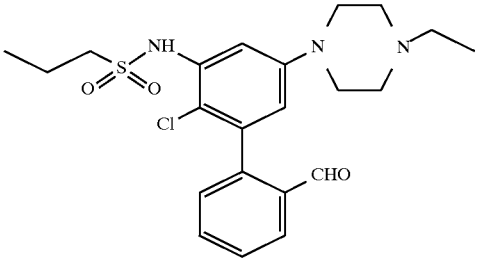

¹H-NMR(400 MHz, CDCl₃); δ(ppm) 9.8(1H, s), 8.0(1H, d), 7.35(2H, m), 6.6(1H, m), 3.3(4H, m), 3.1(2H, m), 2.6(4H, m), 2.5(2H, q), 1.9(2H, m), 1.1(3H, t), 1.0(3H, t).

Example 197

1-Ethyl-4-[3-(2-cyanophenyl)-4-chloro-5-propanesulfonylamino]phenylpiperazine

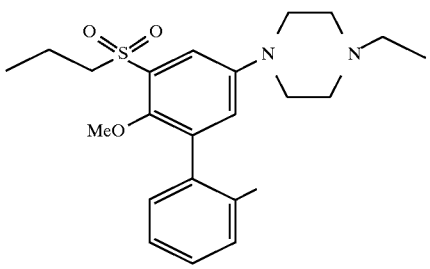

¹H-NMR(400 MHz, CDCl₃); δ(ppm) 7.8(1H, d), 7.7(2H, m), 7.5(2H, m), 6.6(1H, m), 3.3(4H, m), 3.1(2H, m), 2.6(4H, m), 2.5(2H, q), 1.9(2H, m), 1.1(3H, t), 1.0(3H, t).

Example 198

1-[2-(2-Pyridyl)ethyl]-4-[3-(4-fluorophenyl)-4-methoxy-5-ethanesulfonyl]phenylpiperazine

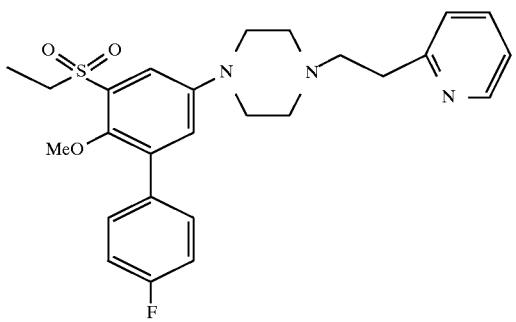

¹H-NMR(400 MHz, CDCl₃); δ(ppm) 8.6(1H, m), 7.6(1H, m), 7.55(2H, m), 7.4(1H, d), 7.2(1H, d), 7.15(3H, m), 7.05(1H, d), 3.5(2H, q), 3.4(3H, s), 3.25(4H, m), 3.0(2H, m), 2.8(2H, m), 2.7(4H, m), 1.3(3H, t).

Example 199

1-(2-Pyridylmethyl)-4-[3-(4-fluorophenyl)-4-methoxy-5-ethanesulfonyl]phenylpiperazine

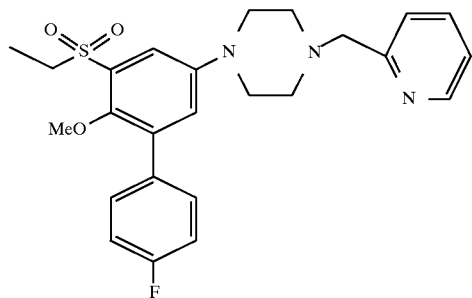

¹H-NMR(400 MHz, CDCl₃); δ(ppm) 8.6(1H, m), 7.7(1H, m), 7.55(2H, m), 7.4(2H, m), 7.2–7.1(3H, m), 7.05(1H, d), 3.75(2H, s), 3.5(2H, q), 3.4(3H, s), 3.3(4H, m), 2.7(4H, m), 1.3(3H, t).

Example 200

1-(3-Pyridylmethyl)-4-[3-(4-fluorophenyl)-4-methoxy-5-ethanesulfonyl]phenylpiperazine

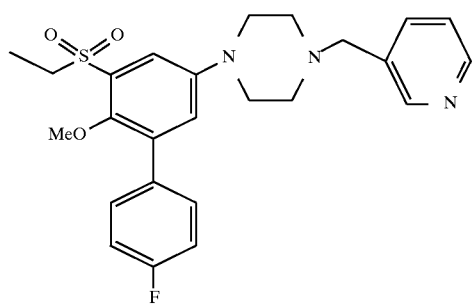

¹H-NMR(400 MHz, CDCl₃); δ(ppm) 8.6(1H, s), 8.55(1H, m), 7.7(1H, m), 7.55(2H, m), 7.4(1H, d), 7.3(1H, m), 7.2(2H, m), 7.0(1H, d), 3.6(2H, s), 3.5(2H, q), 3.4(3H, s), 3.2(4H, m), 2.6(4H, m), 1.3(3H, t), 1.2(3H, t).

Example 201

1-[2-(4-Pyridyl)ethyl]-4-[3-(4-fluorophenyl)-4-methoxy-5-ethanesulfonyl]phenylpiperazine

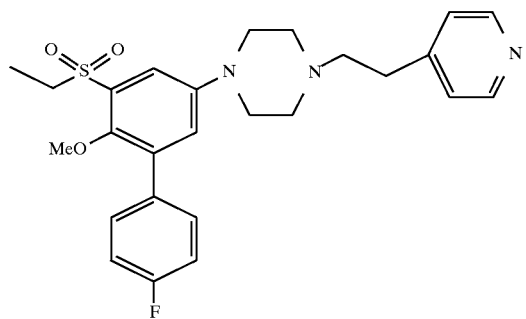

¹H-NMR(400 MHz, CDCl₃); δ(ppm) 8.5(2H, m), 7.55(2H, m), 7.45(1H, d), 7.2(4H, m), 7.05(1H, d), 3.5(2H, q), 3.4(3H, s), 3.25(4H, m), 2.8(2H, m), 2.7(6H, m), 1.3(3H, t), 1.2(3H, t).

Example 202

1-[3-(4-Fluorophenyl)-4-methoxy-5-ethanesulfonyl]phenylpiperazine

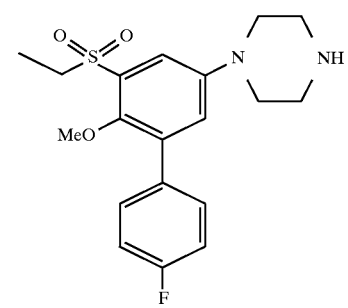

¹H-NMR(400 MHz, CDCl₃); δ(ppm) 7.55(2H, m), 7.45(1H, s), 7.2(2H, m), 7.05(1H, d), 3.9(1H, b-s), 3.5(2H, q), 3.4(3H, s), 3.25(4H, m), 3.1(4H, m), 1.3(3H, t).

Example 203

1-(2-Fluoroethyl)-4-[3-(4-fluorophenyl)-4-methoxy-5-ethanesulfonyl]phenylpiperazine

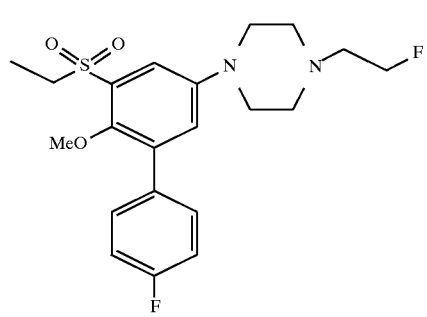

¹H-NMR(400 MHz, CDCl₃); δ(ppm) 7.55(2H, m), 7.4(1H, m), 7.15(2H, m), 7.05(1H, d), 4.6(2H, m), 3.5(2H, q), 3.4(3H, s), 3.25(4H, m), 2.75(2H, d-t), 2.7(4H, m), 1.3(3H, m).

Example 204

1-Ethyl-4-[3-(2-chlorophenyl)-4-chloro-5-(1-propenyl)]phenylpiperazine

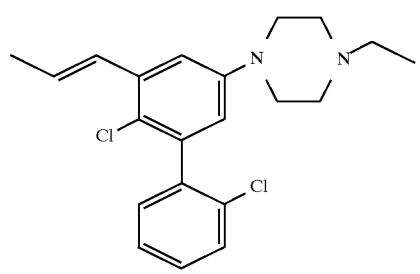

¹H-NMR(400 MHz, CDCl₃); δ(ppm) 7.5(1H, m), 7.3(3H, m), 7.05(1H, m), 6.8(1H, m), 6.7(1H, d), 6.2(1H, m), 3.2(4H, m), 2.6(4H, m), 2.5(2H, q), 1.95(3H, d), 1.15(3H, t).

Example 205

1-Ethyl-4-[3-(2-chlorophenyl)-4-chloro-5-(1-chloropropyl)]phenylpiperazine

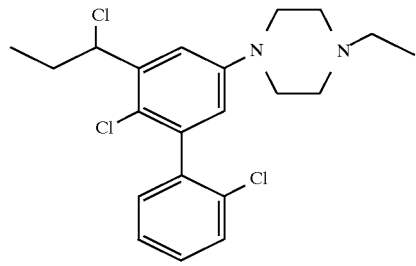

¹H-NMR(400 MHz, CDCl₃); δ(ppm) 7.46(1H, m), 7.17–7.36(4H, m), 6.73(1H, d), 5.40(1H, m), 3.23(4H, m), 2.60(4H, m), 2.46(2H, q), 2.02–2.13(2H, m), 1.13(3H, t), 1.08(3H, t).

Example 206

1-Methyl-4-[3-phenyl-4-chloro-5-(1-fluoropropyl)]phenylpiperazine

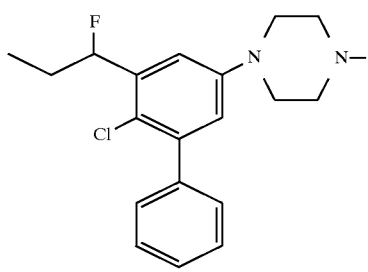

¹H-NMR(400 MHz, CDCl₃); δ(ppm) 7.4(5H, m), 7.05 (1H, d), 6.8(1H, s), 5.8(1H, m), 3.2(4H, m), 2.6(4H, m), 2.35(3H, s), 2.0(2H, m), 1.05(3H, t).

Example 207

1-Methyl-4-[3-(2-hydroxymethylphenyl)-4-chloro-5-(1-fluoropropyl)]phenylpiperazine

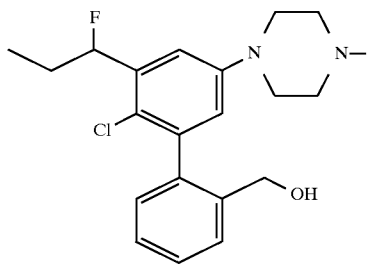

¹H-NMR(400 MHz, CDCl₃); δ(ppm) 7.6(1H, m), 7.4(1H, t), 7.35(1H, m), 7.2(1H, d), 7.05(1H, d), 6.75(1H, d), 5.75 (1H, m), 4.45(2H, m), 3.2(4H, m), 2.6(4H, m), 2.3(3H, s), 2.0(2H, m), 1.05(3H, t).

Example 208

1-Ethyl-4-[3-(2-fluoromethylphenyl)-4-chloro-5-(1-fluoropropyl)]phenylpiperazine

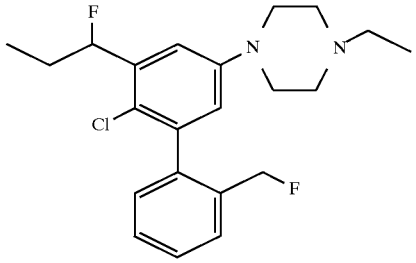

¹H-NMR(400 MHz, CDCl₃); δ(ppm) 7.6(1H, m), 7.4(2H, m), 7.2(1H, d), 7.05(1H, d), 6.8(1H, d), 5.75(1H, m), 5.3–5.0 (2H, m), 3.2(4H, m), 2.6(4H, m), 2.45(2H, q), 2.0(2H, m), 1.1(3H, t), 1.05(3H, t).

Example 209

1-Methyl-4-{3-(2-fluoromethylphenyl)-4-chloro-5-[1-(R)-fluoropropyl)]}phenylpiperazine

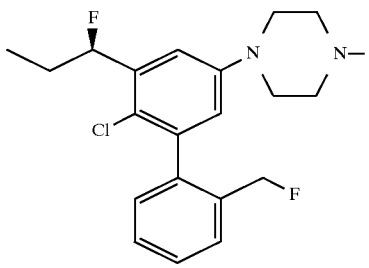

¹H-NMR(400 MHz, CDCl₃); δ(ppm) 7.6(1H, m), 7.4(2H, m), 7.2(1H, d), 7.05(1H, d), 6.8(1H, d), 5.75(1H, m), 5.3–5.0(2H, m), 3.2(4H, m), 2.6(4H, m), 2.35(3H, s), 1.9(2H, m), 1.05(3H, t).

Example 210

1-Methyl-4-{3-(2-fluoromethylphenyl)-4-chloro-5-[1-(S)-fluoropropyl]}phenylpiperazine

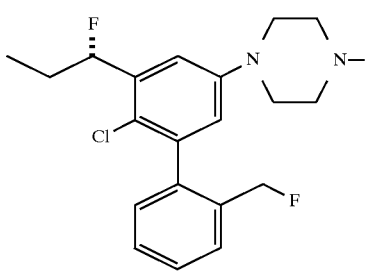

¹H-NMR(400 MHz, CDCl₃); δ(ppm) 7.6(1H, m), 7.4(2H, m), 7.2(1H, d), 7.05(1H, d), 6.8(1H, d), 5.75(1H, m), 5.3–5.0 (2H, m), 3.2(4H, m), 2.6(4H, m), 2.35(3H, s), 1.9(2H, m), 1.05(3H, t).

Example 211

1-Ethyl-4-{3-[2(4-fluorotolyl)]-4-chloro-5-[1-fluoropropyl]}phenylpiperazine

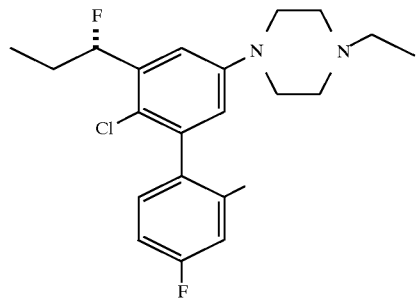

¹H-NMR(400 MHz, CDCl₃); δ(ppm) 7.1–7.0(2H, m), 7.0–6.9(2H, m), 6.7(1H, d), 5.75(1H, m), 3.25(4H, m), 2.6(4H, m), 2.5(2H, q), 2.1(3H, d), 1.15(3H, t), 1.05(3H, m).

Example 212

1-Ethyl-4-{3-[2-(4-fluorotolyl)]-4-chloro-5-[1-(R)-fluoropropyl]}phenylpiperazine

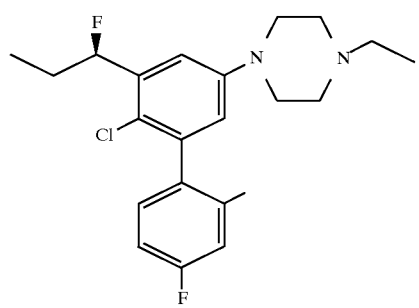

¹H-NMR(400 MHz, CDCl₃); δ(ppm) 7.1–7.0(2H, m), 7.0–6.9(2H, m), 6.7(1H, d), 5.75(1H, m), 3.25(4H, m), 2.6(4H, m), 2.5(2H, q), 2.1(3H, d), 1.15(3H, t), 1.05(3H, m).

Example 213

1-[2-(2-Pyridyl)ethyl]-4-[3-(2-tolyl)-4-chloro-5-(1-fluoropropyl)]phenylpiperazine

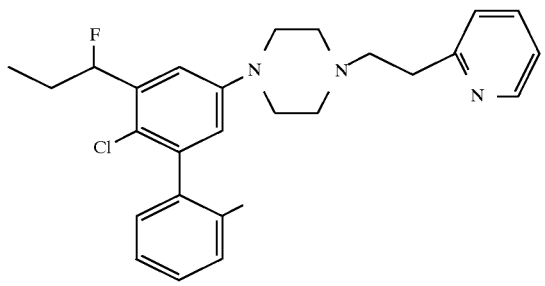

¹H-NMR(400 MHz, CDCl₃); δ(ppm) 8.55(1H, d), 7.6 (1H, m), 7.3–7.2(4H, m), 7.1(2H, m), 7.05(1H, d), 6.7(1H, d), 5.8(1H, m), 3.2(4H, m), 3.0(2H, m), 2.8(2H, m), 2.7(4H, m), 2.1(3H, d), 1.9(2H, m), 1.05(3H, m).

Example 214

1-[2-(2-Pyridyl)ethyl]-4-[3-(2-cyanophenyl)-4-chloro-5-(1-fluoropropyl)]phenylpiperazine

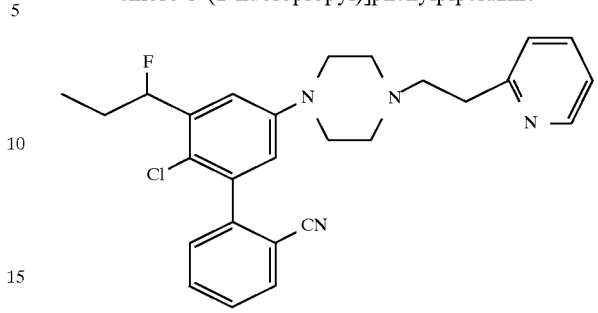

¹H-NMR(400 MHz, CDCl₃); δ(ppm) 8.55(1H, d), 7.8 (1H, d), 7.6(2H, m), 7.45(2H, m), 7.2(1H, d), 7.1(2H, m), 6.8(1H, d), 5.8(1H, m), 3.25(4H, m), 3.0(2H, m), 2.8(2H, m), 2.7(4H, m), 2.0(2H, m), 1.05(3H, t).

Example 215

1-Ethyl-4-[3-(2,6-xylyl)-4-chloro-5-(1-fluoropropyl)] phenylpiperazine

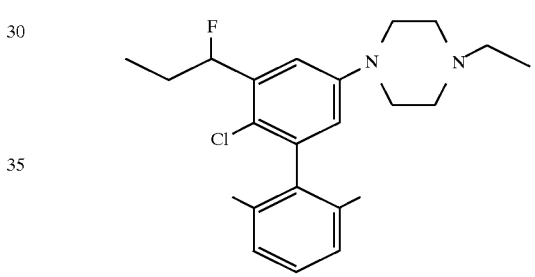

¹H-NMR(400 MHz, CDCl₃); δ(ppm) 7.2–7.0(4H, m), 6.65(1H, d), 5.8(1H, m), 3.2(4H, m), 2.6(4H, m), 2.5(2H, q), 2.0(6H, d), 1.9(2H, m), 1.15(3H, t), 1.05(3H, t).

Example 216

1-Ethyl-4-{3-(2-trifluoromethylphenyl)-4-chloro-5-[1-(R)-fluoropropyl]}phenylpiperazine

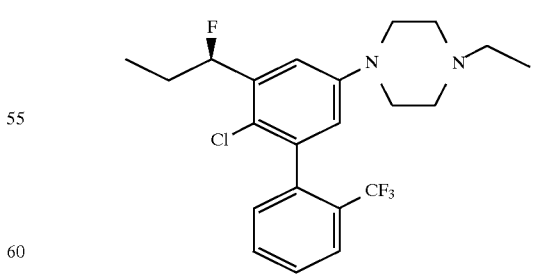

¹H-NMR(400 MHz, CDCl₃); δ(ppm) 7.8(1H, m), 7.6(1H, m), 7.5(1H, m), 7.25(1H, m), 7.05(1H, d), 6.75(1H, m), 5.8(1H, m), 3.2(4H, m), 2.6(4H, m), 2.45(2H, q), 1.9(2H, m), 1.15(3H, t), 1.05(3H, d-t).

Example 217

1-Ethyl-4-[3-(2-ethylphenyl)-4-chloro-5-(1-fluoropropyl)]phenylpiperazine

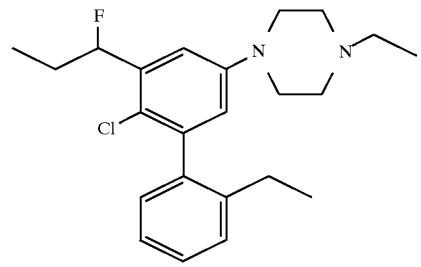

$^1$H-NMR(400 MHz, CDCl$_3$); δ(ppm) 7.4–7.2(3H, m), 7.1(1H, d), 7.05(1H, m), 6.75(1H, d), 5.8(1H, m), 3.2(4H, m), 2.6(4H, m), 2.5–2.3(4H, m), 1.9(2H, m), 1.2–1.0(6H, m).

Example 218

1-(2-Hydroxyethyl)-4-[3-(2-ethylphenyl)-4-chloro-5-(1-fluoropropyl)]phenylpiperazine

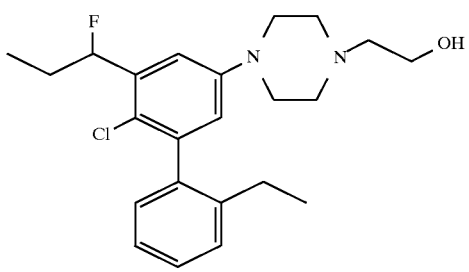

$^1$H-NMR(400 MHz, CDCl$_3$); δ(ppm) 7.4–7.2(3H, m), 7.1(1H, d), 7.05(1H, d), 6.75(1H, d), 5.8(1H, d), 3.6(2H, t), 3.2(4H, m), 2.65(4H, m), 2.60(2H, t), 2.40(2H, m), 1.9(2H, m), 1.05(6H, m).

Example 219

1-(2-Hydroxyethyl)-4-{3-(2-trifluoromethylphenyl)-4-chloro-5-[1-(R)-fluoropropyl]}phenylpiperazine

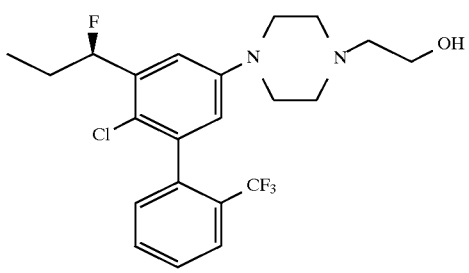

$^1$H-NMR(400 MHz, CDCl$_3$); δ(ppm) 7.8(1H, m), 7.6(1H, m), 7.5(1H, m), 7.25(1H, m), 7.05(1H, d), 6.75(1H, m), 5.8(1H, m), 3.2(4H, m), 2.6(4H, m), 2.45(2H, q), 1.9(2H, m), 1.15(3H, t), 1.05(3H, d-t).

Example 220

1-Methyl-4-{3-(2-tolyl)-4-chloro-5-[1-(R)-fluoropropyl]}phenylpiperazine

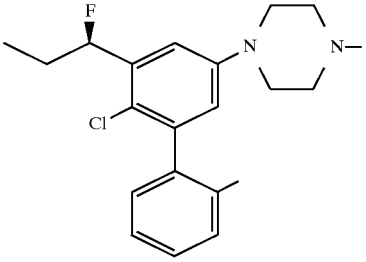

$^1$H-NMR(400 MHz, CDCl$_3$); δ(ppm) 7.09–7.28(4H, m), 7.03(2H, d), 6.71(2H, d), 5.78(1H, m), 3.22(4H, m), 2.58(4H, m), 2.37(3H, s), 2.12(3H, d), 1.82–2.03(2H, m), 1.07(3H, d-t).

Example 221

1-Methyl-4-{3-(2-tolyl)-4-chloro-5-[1-(S)-fluoropropyl]}phenylpiperazine

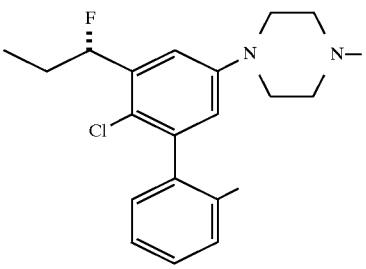

$^1$H-NMR(400 MHz, CDCl$_3$); δ(ppm) 7.09–7.28(4H, m), 7.03(2H, d), 6.71(2H, d), 5.78(1H, m), 3.22(4H, m), 2.58(4H, m), 2.37(3H, s), 2.12(3H, d), 1.82–2.03(2H, m), 1.07(3H, d-t).

Example 222

1-(2-Hydroxyethyl)-4-{3-[2-(4-fluorotolyl)]-4-chloro-5-[1-(S)-fluoropropyl]}phenylpiperazine

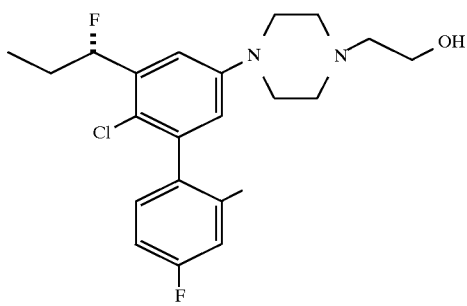

$^1$H-NMR(400 MHz, CDCl$_3$); δ(ppm) 7.1(2H, m), 6.95(2H, m), 6.7(1H, d), 5.8(1H, m), 3.7(2H, m), 3.2(4H, m), 2.7(4H, m), 2.6(2H, m), 2.1(3H, d), 1.9(2H, m), 1.05(3H, m).

Example 223

1-(2-Hydroxyethyl)-4-{3-[2-(4-fluorotolyl)]-4-chloro-5-[1-(R)-fluoropropyl]}phenylpiperazine

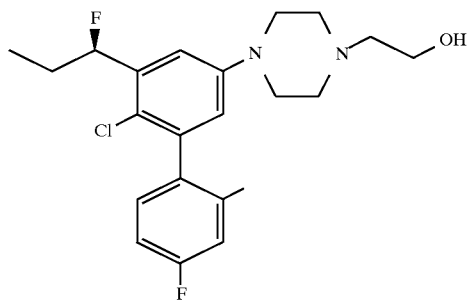

$^1$H-NMR(400 MHz, CDCl$_3$); δ(ppm) 7.1(2H, m), 6.95 (2H, m), 6.7(1H, d), 5.8(1H, m), 3.7(2H, m), 3.2(4H, m), 2.7(4H, m), 2.6(2H, m), 2.1(3H, d), 1.9(2H, m), 1.05(3H, m).

Example 224

Synthesis of 2-chloro-3-bromo-3-nitrobenzoic acid

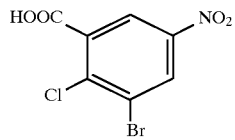

26.63 g (86.3 mmol) of ethyl 2-chloro-3-bromo5-nitrobenzoate was dissolved in a mixture comprising 150 ml of ethanol and 80 ml of THF, followed by the addition of 55 ml of a 2N aqueous solution of sodium hydroxide. The obtained mixture was stirred at room temperature for one hour, followed by the addition of water and 19 ml of 6N hydrochloric acid. The obtained mixture was concentrated under reduced pressure and extracted with ethyl acetate. The ethyl acetate phase was washed with a saturated aqueous solution of common salt, dried and distilled to remove the solvent, giving 24.11 g of the title compound (yield: quantitative).

m.p.; 162°–163.5° C.

$^1$H-NMR(400 MHz, DMSO-d$_6$); δ(ppm) 8.47(1H, d, J=2.7 Hz), 8.68(1H, d, J=2.7 Hz).

MS m/z: 280[M−H]$^-$, 278[M−H]$^-$.

Example 225

Synthesis of 2-chloro-3-bromo-5-nitrobenzoyl chloride

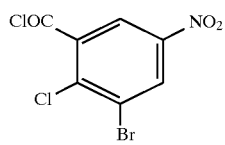

5.1 ml (69.9 mmol) of thionyl chloride and a solvent mixture comprising 50 ml of benzene and 0.2 ml of DMF were added to 14.07 g (50.2 mmol) of 2-chloro-3-bromo-5-nitrobenzoic acid. The obtained mixture was heated under reflux for 2 hours and distilled to remove the solvent. Benzene was added to the residue and the obtained mixture was distilled again to remove the solvent. Thus, 15.07 g of the title compound was obtained (yield: quantitative).

This product was used in the following reaction without any additional purification.

$^1$H-NMR(400 MHz, CDCl$_3$); δ(ppm) 8.71(1H, d, J=2.7 Hz), 8.74(1H, d, J=2.7 Hz).

Example 226

Synthesis of diethyl 2-(2-chloro-3-bromo-5-nitrobenzoyl)-2-methylmalonate

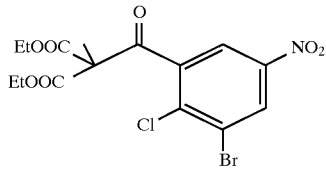

2.2 g of 55% sodium hydride was suspended in 30 ml of THF, followed by the addition of 50 ml of a THF solution of 8.65 ml (50.3 mmol) of diethyl methylmalonate under cooling with ice. The obtained mixture was stirred at room temperature for 20 minutes and cooled with ice again, followed by the dropwise addition of 85 ml of a THF solution of the 2-chloro-3-bromo-5-nitrobenzoyl chloride prepared in the above Example. The obtained mixture was stirred as such for 1.5 hours and then poured into an aqueous solution of ammonium chloride. The resulting mixture was extracted with ethyl acetate. The ethyl acetate phase was washed with a saturated aqueous solution of sodium hydrogen carbonate and a saturated brine, dried and distilled to remove the solvent. 30 ml of methylene chloride was added to the residue. The resulting mixture was freed from insolubles by filtration and concentrated under reduced pressure to give 21.77 g of the title compound (yield: quantitative).

m.p.; 75°–76.5° C.

$^1$H-NMR(400 MHz, CDCl$_3$); δ(ppm) 1.24(6H, t, J=7.1 Hz), 1.84(3H, s), 4.22(2H, q, J=7.1 Hz), 4.23(2H, q, J=7.1 Hz), 8.43(1H, d, J=2.6 Hz), 8.55(1H, d, J=2.6 Hz), MS m/z: 438[MH]$^+$, 436[MH]$^+$.

Example 227

Synthesis of 2-chloro-3-bromo-5-nitropropiophenone

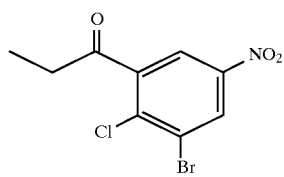

90 ml of acetic acid, 14.0 ml of concentrated hydrochloric acid and 7.0 ml of concentrated sulfuric acid were added to 21.72 g of diethyl 2-(2-chloro-3-bromo-5-nitrobenzoyl)-2-methylmalonate. The obtained mixture was heated under reflux for 13 hours and then poured into a mixture comprising 350 ml of ice-water and 100 ml of ethyl acetate. The resulting mixture was extracted with ethyl acetate. The ethyl acetate phase was washed with a saturated brine and a saturated aqueous solution of sodium hydrogen carbonate successively, dried and distilled to remove the solvent, giving 10.56 g of the title compound (yield: 72%).

m.p.; 81.5°–83° C.

$^1$H-NMR(400 MHz, CDCl$_3$); δ(ppm) 1.25(3H, t, J=7.1 Hz), 2.96(2H, q, J=7.1 Hz), 8.17(1H, d, J=2.6 Hz), 8.57(1H, d, J=2.6 Hz).

MS m/z: 292[MH]$^+$, 294[MH]$^+$, 296[MH]$^+$.

Example 228

Synthesis of 1-(2-chloro-3-bromo-5-nitrophenyl)-1-propanol

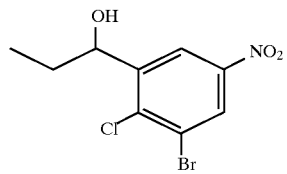

7.48 g (25.6 mmol) of 2-chloro-3-bromo-5-nitropropiophenone was dissolved in 50 ml of methanol, followed by the addition of 735 mg (19.4 mmol) of sodium borohydride under cooling with ice. The obtained mixture was stirred for 30 minutes, followed by the addition of an aqueous solution of ammonium chloride. The resulting mixture was extracted with ethyl acetate. The ethyl acetate phase was washed with a saturated brine, dried and distilled to remove the solvent, giving 7.42 g of the title compound (yield: quantitative).

m.p.; 110°–113° C.

$^1$H-NMR(400 MHz, CDCl$_3$); δ(ppm) 1.05(3H, t, J=7.5 Hz), 1.69(1H, m), 1.88(1H, m), 2.15(1H, d, J=4.0 Hz), 5.13(1H, dt, J=7.9, 4.0 Hz), 8.42(1H, d, J=2.6 Hz), 8.46(1H, d, J=2.6 Hz).

MS m/z: 295[MH]$^-$, 293[M–H]$^-$.

Example 229

Synthesis of 3-bromo-4-chloro-5-(1-fluoropropyl)-1-nitrobenzene

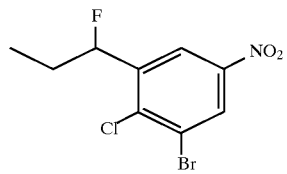

9.0 ml of hexafluoropropenediethylamine and 80 ml of a chloroform solution of 7.32 g (25.0 mol) of 1-(2-chloro-3-bromo-5-nitrophenyl)-1-propanol were dropwise added to 25 ml of chloroform under cooling with ice in this order. The obtained mixture was stirred as such for 40 minutes, followed by the addition of a saturated aqueous solution of sodium hydrogen carbonate. The obtained mixture was stirred for 30 minutes and left standing to cause liquid-liquid separation. The chloroform phase was separated. The aqueous phase was further extracted with ethyl acetate and the ethyl acetate phase was washed with a saturated brine. The resulting ethyl acetate phase and the above chloroform phase were combined, dried and distilled to remove the solvent.

The obtained residue was purified by silica gel column chromatography to give 6.64 g of the title compound (yield: 90%).

$^1$H-NMR(400 MHz, CDCl$_3$); δ(ppm) 1.09(3H, t, J=7.5 Hz), 1.78–2.12(2H, m), 5.78(1H, ddd, J=47.1, 7.9, 3.5 Hz), 8.33(1H, d, J=2.7 Hz), 8.48(1H, d, J=2.7 Hz).

Example 230

Synthesis of 3-bromo-4-chloro-5-(1-fluoropropyl) aniline

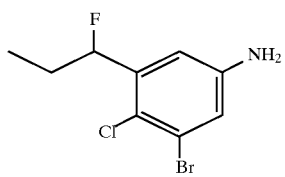

6.54 g (22.1 mmol) of 3-bromo-4-chloro-5-(1-fluoropropyl)-1-nitrobenzene was dissolved in a solvent mixture comprising 30 ml of methanol and 90 ml of acetonitrile, followed by the addition of 120 ml of a 20% solution of titanium trichloride in diluted hydrochloric acid under a nitrogen stream under cooling with ice. The obtained mixture was stirred at room temperature for 3 hours and then poured into water. The resulting mixture was extracted with ethyl acetate. The ethyl acetate phase was washed with a saturated aqueous solution of sodium hydrogen carbonate and a saturated brine successively, dried and distilled to remove the solvent. The residue was purified by silica gel column chromatography to give 5.04 g of the title compound (yield: 86%).

$^1$H-NMR(400 MHz, CDCl$_3$); δ(ppm) 1.03(3H, t, J=7.5 Hz), 1.7–2.1(2H, m), 3.77(2H, brs), 5.66(1H, ddd, J=47.4, 7.9, 3.6 Hz), 6.74(1H, d, J=2.7 Hz), 6.91(1H, d, J=2.7 Hz).

MS m/z: 267[M$^+$], 265[M$^+$].

Example 231

Synthesis of 1-[3-bromo-4-chloro-5-(1-fluoropropyl)]phenylpeperazine

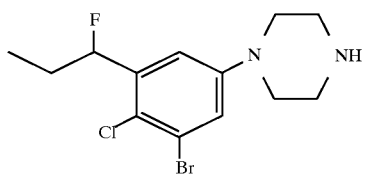

1.81 g (6.79 mmol) of 3-bromo-4-chloro-5-(1-fluoropropyl)aniline and 1.28 g (7.17 mmol) of bis(2-chloroethyl)amine hydrochloride were suspended in 6 ml of 1,2-dichlorobenzene. The obtained suspension was heated on an oil bath of 153° C. under a nitrogen stream for 11 hours, cooled, adjusted to pH8 with a 2N aqueous solution of sodium hydroxide and extracted with ethyl acetate. The ethyl acetate phase was washed with a saturated brine, dried and distilled to remove the solvent. The obtained residue was purified by silica gel column chromatography to give 1.25 g (yield: 55%) of the title compound and 0.50 g (yield: 23%) of (E)-1-[3-bromo-4-chloro-5-(1-propenyl)] phenylpiperazine

(E)-1-[3-bromo-4-chloro-5-(1-propenyl)]phenylpiperazine

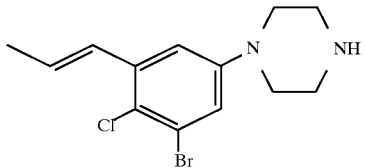

$^1$H-NMR(400 MHz, CDCl$_3$); δ(ppm) 1.91(3H, dd, J=6.8, 1.8 Hz), 3.66(1H, br), 6.68(1H, dq, J=15.7 Hz, 6.8 Hz), 6.72(1H, dd, J=15.7, 1.8 Hz), 6.73(1H, d, J=2.7 Hz), 6.85 (1H, d, J=2.7 Hz).

MS m/z: 317[MH]$^+$, 315[MH]$^+$.

Example 232

Synthesis of 1-(t-butoxycarbonyl)-4-(3-bromo-4-chloro-5-carboxy)phenylpiperazine

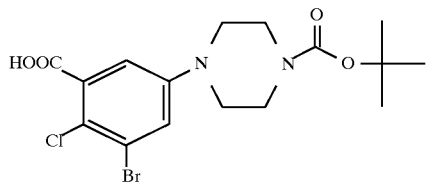

20 ml of water, 150 ml of ethanol and 61 ml of a 2N aqueous solution of sodium hydroxide were added to 5.2 g (13.56 mmol) of 1-(3-bromo-4-chloro-5-ethoxycarbonyl) phenylpiperazine hydrochloride, followed by the addition of a solution of 5.29 g (2 equivalents) of di(t-butyl) dicarbonate [Boc$_2$O] in 25 ml of ethanol under cooling with ice. The obtained mixture was freed from insolubles by filtration and distilled to remove the solvent, followed by the addition of 23 ml of 2N hydrochloric acid under cooling with ice. The obtained mixture was extracted with ethyl acetate. The ethyl acetate phase was dried and distilled to remove the solvent. Isopropyl ether was added to the obtained residue to precipitate a crystal. This crystal was recovered by filtration to give 4.64 g of the title compound (yield: 82%).

m.p.; 183°–184.5° C. (dec.)

$^1$H-NMR(400 MHz, CDCl$_3$); δ(ppm) 1.48(9H, s), 3.17 (4H, m), 3.58(4H, m), 4.2(1H, br), 7.30(1H, d, J=2.9 Hz), 7.36(1H, d, J=2.9 Hz).

MS m/z: 420[M$^+$], 418[M$^+$].

Example 233

Synthesis of 1-(t-butoxycarbonyl)-4-[3-bromo-4-chloro-5-(2-pyridylthio)carbonyl]phenylpiperazine

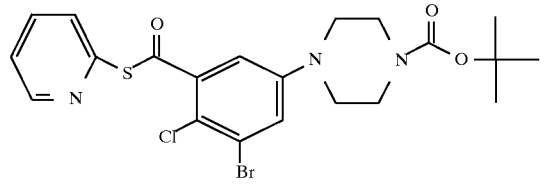

1.06 ml (13.7 mmol) of N,N-dimethylformamide (hereinafter abbreviated to "DMF") and 0.99 ml (13.6 mmol) of thionyl chloride were added to 20 ml of tetrahydrofuran (hereinafter abbreviated to "THF"), followed by stirring at room temperature for at least 30 minutes. A solution of 5 g (11.9 mmol) of 1-(t-butoxycarbonyl)-4-(3-bromo-4-chloro-5-carboxy)phenylpiperazine in 25 ml of THF was dropwise added to the mixture prepared above under cooling with ice, followed by stirring at 50° C. for one hour. A solution of 2.07 g (18.6 mmol) of 2-mercaptopyridine and 5.2 ml (37.3 mmol) of triethylamine in 30 ml of THF was dropwise added to the resulting mixture under cooling with ice. The obtained mixture was stirred at room temperature for about one hour and then poured into ice-water. The resulting mixture was extracted with ethyl acetate. The organic phase was washed with a 1N aqueous solution of sodium hydroxide and a saturated brine, dried and distilled to remove the solvent. Isopropyl ether was added to the residue to precipitate a crystal. This crystal was recovered by filtration to give 5.61 g of the title compound (yield: 92%).

Example 234

Synthesis of 1-(t-butoxycarbonyl)-4-[3-bromo-4-chloro-5-(2-pyridylthio)carbonyl]phenylpiperazine 5 g (11.9 mmol) of 1-(t-Butoxycarbonyl)-4-(3-bromo-4-chloro-5-carboxy)phenylpiperazine and 3.5 ml (25.1 mmol) of triethylamine were dissolved in 20 ml of THF. 30 ml of a solution of 2.7 ml (13.0 mmol) of diphenylphosphoric chloride in THF was dropwise added to the solution prepared above under cooling with ice, followed by stirring at room temperature for one hour. A solution of 1.51 g (1.14 equivalents) of 2-mercaptopyridine in 30 ml of THF was dropwise added to the resulting mixture under cooling with ice. The obtained mixture was stirred at 50° C. for one hour and then poured into ice-water. The resulting mixture was extracted with ethyl acetate. The organic phase was washed with a 1N aqueous solution of sodium hydroxide and a saturated brine, dried and distilled to remove the solvent. Isopropyl ether was added to the residue to precipitate a crystal. This crystal was recovered by filtration to give 5.93 g of the title compound (yield: 97%).

m.p.; 156°~157° C.

$^1$H-NMR(400 MHz, CDCl$_3$); δ(ppm) 1.48(9H, s), 3.19 (4H, m), 3.58(4H, m), 7.15(1H, d, J=2.9 Hz), 7.24(1H, d, J=2.9 Hz), 7.35(1H, ddd, J=7.3, 4.8, 1.5 Hz), 7.77(1H, ddd, J=7.9, 1.5, 0.9 Hz), 7.82(1H, ddd, J=7.9, 7.3, 1.8 Hz), 8.67(1H, ddd, J=4.8, 1.8, 0.9 Hz).

MS m/z: 514[MH]$^+$, 512[MH]$^+$.

Example 235

Synthesis of 1-(t-butoxycarbonyl)-4-(3-bromo-4-chloro-5-propionyl)phenylpiperazine

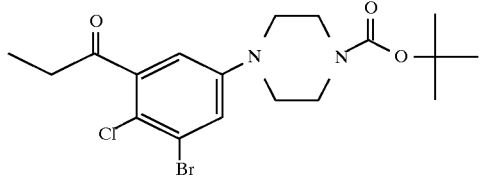

4.5 g (8.78 mmol) of 1-(t-butoxycarbonyl)-4-[3-bromo-4-chloro-5-(2-pyridylthio)carbonyl]phenylpiperazine was dissolved in 50 ml of THF. 9.7 ml of a 1M solution of ethylmagnesium bromide in THF was dropwise added to the obtained solution in 30 minutes, followed by the addition of a saturated aqueous solution of ammonium chloride and water in this order. The resulting mixture was extracted with ethyl acetate. The organic phase was washed with a 1N aqueous solution of sodium hydroxide and a saturated brine, dried and distilled to remove the solvent. The residue was purified by silica gel column chromatography (with ethyl acetate/hexane) to give 2.28 g of the title compound (yield: 60%).

m.p.; 119°~122.5° C.

¹H-NMR(400 MHz, CDCl₃); δ(ppm) 1.20(3H, t, J=7.3 Hz), 1.48(9H, s), 2.91(2H, q, J=7.3 Hz), 3.15(4H, m), 3.57(4H, m), 6.72(1H, d, J=2.9 Hz), 7.19(1H, d, J=2.9 Hz).

MS m/z: 432[M⁺], 430[M⁺].

Example 236

Synthesis of 1-(3,5-dibromo-4-chloro)phenylpiperazine

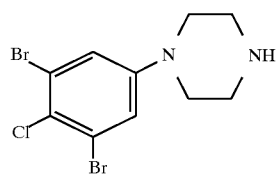

10.0 g (35 mmol) 3,5-dibromo-4-chloroaniline (CAS registration No. 35754-04-2) and 15.6 g (87.5 mmol) of bis(2-chloroethyl)amine hydrochloride were suspended in 120 ml of 1,2-dichlorobenzene. The obtained suspension was heated on an oil bath of 180° C. under a nitrogen stream for 8 hours. 300 ml of ethyl acetate was added to the resulting mixture to form a precipitate. This precipitate was recovered by filtration, washed with ethyl acetate and suspended in 500 ml of methanol. The obtained suspension was heated under reflux, freed from insolubles by filtration, and distilled to remove the solvent. The crystal thus precipitated was recovered by filtration to give 13.7 g of the title compound (yield: 100%).

m.p.; over 270° C.

¹H-NMR(400 MHz, DMSO-d₆); δ(ppm) 3.14(4H, m), 3.46(4H, m), 7.38(2H, s).

MS m/z: 357[MH]⁺, 355[MH]⁺, 353[MH]⁺.

Example 237

Synthesis of 1-(t-butoxycarbonyl)-4-(3,5-dibromo-4-chloro)phenylpiperazine

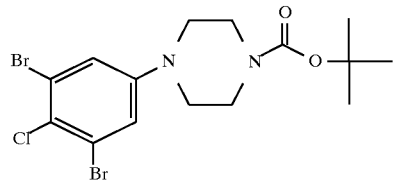

13.7 g (35 mmol) of 1-(3,5-dibromo-4-chloro)phenylpiperazine was suspended in 200 ml of acetonitrile, followed by the dropwise addition of 14.4 ml (70 mmol) of triethylamine under cooling with ice. A solution of 11.1 g (42 mmol) of di(t-butyl)dicarbonate in 15 ml of acetonitrile was dropwise added to the resulting mixture under cooling with ice in 10 minutes. The obtained mixture was stirred at room temperature for 15 hours, followed by the addition of water. The resulting mixture was extracted with ethyl acetate. The organic phase was washed with water, dried and concentrated under reduced pressure. The obtained residue was purified by silica gel chromatography (with ethyl ether/hexane) to give 17.8 g of the title compound as a colorless crystal (yield: 83.3%).

m.p.; 149°~151° C.

¹H-NMR(400 MHz, CDCl₃); δ(ppm) 1.48(9H, s), 3.13 (4H, m), 3.57(4H, m), 7.10(2H, s).

MS m/z: 456[M]⁺, 454[M]⁺, 452[M]⁺.

Example 238

Synthesis of 1-(t-butoxycarbonyl)-4-(3-bromo-4-chloro-5-propionyl)phenylpiperazine

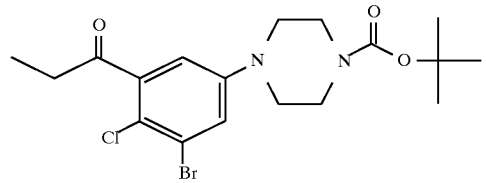

3.8 ml of a 1.66M solution of n-butyllithium in n-hexane was dropwise added to a solution of 2.5 g (5.5 mmol) of 1-(t-butoxycarbonyl)-4-(3,5-dibromo-4-chloro)phenylpiperazine in 10 ml of THF in about 5 minutes at −100° C. Then, a solution of 860 mg (6.6 mmol) of propionic anhydride in 2.5 ml of THF was dropwise added to the above-prepared mixture at −100° C. in about 3 minutes. The obtained mixture was stirred as such for one hour (during this stirring, the temperature rose from −100° C. to −20° C.). A saturated aqueous solution of ammonium chloride was added to the resulting mixture, followed by extraction with ethyl acetate. The organic phase was washed with water and a saturated brine, dried and distilled to remove the solvent. The residue was purified by silica gel column chromatography (with ethyl acetate/n-hexane) to give 1.55 g of the title compound (yield: 65%).

15 ml of isopropanol was added to the above product. The product was dissolved in the isopropanol by heating and the obtained solution was stirred under cooling with ice for one hour to precipitate a crystal. This crystal was recovered by filtration to give 1.0 g of the title compound as a crystal (yield: 42.1%).

m.p.; 121°~123° C.

¹H-NMR(400 MHz, CDCl₃); δ(ppm) 1.20(3H, t, J=7.3 Hz), 1.48(9H, s), 2.91(2H, q, J=7.3 Hz), 3.15(4H, m), 3.57(4H, m), 6.72(1H, d, J=2.9 Hz), 7.19(1H, d, J=2.9 Hz).

Example 239

Synthesis of 1-(t-butoxycarbonyl)-4-[3-bromo-4-chloro-5-(1-hydroxypropyl)]phenylpiperazine

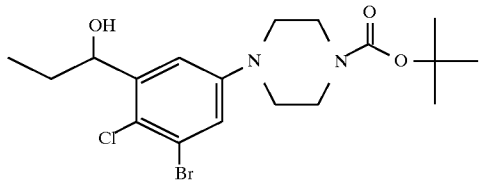

0.8 ml (1.2 equivalents) of a 1.66M solution of n-butyllithium in n-hexane was dropwise added to a solution of 500 g (1.1 mmol) of 1-(t-butoxycarbonyl)-4-(3,5-dibromo-4-chloro)phenylpiperazine in 10 ml of THF at −76° C. in about 4 minutes, followed by the dropwise addition of a solution of 77 mg (1.3 mmol) of propionaldehyde in 0.5 ml of THF at −76° C. in about 2 minutes. The obtained mixture was stirred as such for one hour (during this stirring, the temperature rose from −76° C. to −10° C.). A saturated aqueous solution of ammonium chloride was added to the resulting mixture, followed by extraction with ethyl acetate. The organic phase was washed with water and a saturated brine, dried and distilled to remove the solvent. The residue was purified by silica gel column chromatography (with ethyl acetate/n-hexane) to give 0.31 g of the title compound as a colorless oil (yield: 65%).

$^1$H-NMR(400 MHz, DMSO-$d_6$); δ(ppm) 1.01(3H, t, J=7.6 Hz), 1.48(9H, s), 1.6–1.9(2H, m), 3.15(4H, m), 3.58(4H, m), 5.03(1H, m), 6.07(1H, d, J=2.9 Hz), 7.10(1H, d, J=2.9 Hz).

MS m/z: 434[M]$^+$, 432[M]$^+$.

Example 240

Synthesis of 1-(2-trimethylsilyloxyethyl)-4-[3-bromo-4-chloro-5-(1-fluoropropyl)]phenylpiperazine

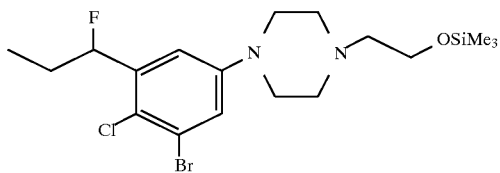

500 mg (1.05 mmol) of 1-(2-hydroxyethyl)-4-[3-bromo-4-chloro-5-(1-fluoropropyl)]phenylpiperazine methanesulfonate was suspended in 5 ml of ethyl acetate, followed by the addition of 0.35 ml (2.56 mmol) of triethylamine under cooling with ice. A solution of 0.16 ml (1.26 mmol) of trimethylsilyl chloride in 1 ml of ethyl acetate was dropwise added to the resulting mixture while stirring the mixture under cooling with ice. The obtained mixture was stirred at room temperature for 1.5 hours, followed by the addition of 5 ml of n-hexane. The obtained mixture was filtered to remove insolubles and the filtrate was concentrated under reduced pressure to give 0.51 g of the title compound. This product was used in the following reaction without any additional purification.

$^1$H-NMR(400 MHz, CDCl$_3$); δ(ppm) 0.13(9H, s), 1.04 (3H, t, J=7.3 Hz), 1.7–2.0(2H, m), 2.58(2H, t, J=6.2 Hz), 2.66(4H, m), 3.19(4H, m), 3.75(2H, J=6.2 Hz), 5.69(1H, ddd, J=47.5, 7.9, 3.7 Hz), 6.95(1H, d, J=2.9 Hz), 7.09(1H, d, J=2.9 Hz).

Example 241

Synthesis of 1-(2-hydroxyethyl)-4-[3-(2-cyanophenyl)-4-chloro-5-(1-fluoropropyl)]phenylpiperazine hydrochloride

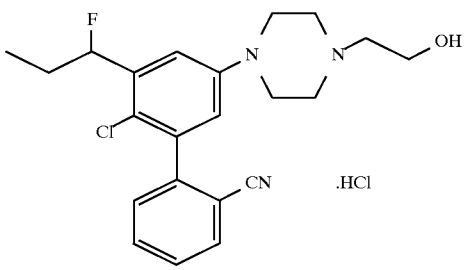

1-(2-Trimethylsilyloxyethyl)-4-[3-bromo-4-chloro-5-(1-fluoropropyl)]phenylpiperazine was dissolved in 4 ml of DMF, followed by the addition of 334 mg (1.58 mmol) of potassium phosphate and 61 mg (0.05 mmol) of tetrakis (triphenylphosphine)palladium (0). A solution of 236 mg (1.26 mmol) of 2-(1,3,2-dioxaborinan-2-yl)benzonitrile in 3 ml of DMF was dropwise added to the resulting mixture at 100° C. in 30 minutes. The obtained mixture was stirred as such at 100° C. for 30 minutes and cooled, followed by the addition of water. The resulting mixture was extracted with ethyl acetate. The organic phase was washed with water and a saturated brine, dried and distilled to remove the solvent, giving 0.52 g of a residue.

This residue was dissolved in 1 ml of ethanol, followed by the dropwise addition of 0.57 g of a 10% solution of hydrochloric acid in ethanol under cooling with ice. The obtained mixture was stirred at 4° C. for 20 hours to give a precipitate. The precipitate was recovered by filtration and dried to give 0.39 g of the title compound (yield: 83.9%).

Example 242

Synthesis of 1-(t-butoxycarbonyl)-4-{3-bromo-4-chloro-5-[1-(S)-hydroxypropyl]}phenylpiperazine

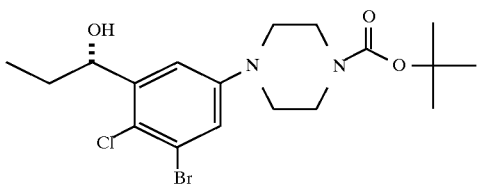

55.8 g (173 mmol) of (−)-Dip-chloride [CAS registration No. 85116-37-6] was added to a solution of 30.0 g (69.7 mmol) of 1-(t-butoxycarbonyl)-4-(3-bromo-4-chloro-5-propionyl)phenylpiperazine in 450 ml of THF. The obtained mixture was stirred at room temperature for 24 hours. Water and ethyl acetate were added to the reaction mixture to conduct partition. The organic phase was washed with water and a brine, dried and distilled to remove the solvent. The residue was purified by silica gel chromatography to give 27.2 g of the title compound (yield: 90%, optical purity; 94% ee).

<Method for the determination of optical purity>

A proper amount of a sample was deprotected with trifluoroacetic acid and treated with carbobenzoxy chloride (hereinafter abbreviated to "Z—Cl") to form an N—Z derivative, which was used as a test sample.

<Conditions of determination>
   stationary phase: CHIRALPAK AD (a product of Daicel Chemical Industries, Ltd.)
   Φ 4.6×250 mm
   mobile phase: ethanol (0.5 ml/min.)
   detector: UV detector, at 254 nm
<Retention time>
   S isomer: 23 to 24 min.
   R isomer: 28 to 30 min.

Example 243

Synthesis of 1-(t-butoxycarbonyl)-4-{3-bromo-4-chloro-5-[1-(R)-fluoropropyl]}phenylpiperazine

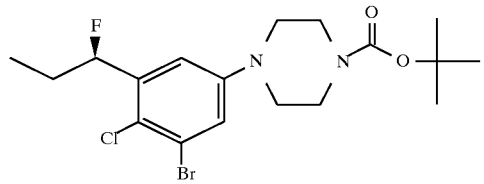

19.4 g (41.5 mmol) of hexafluoropropenediethylamine was dropwise added to a solution of 18.0 g (41.5 mmol, 94% ee) of 1-(t-butoxycarbonyl)-4-{3-bromo-4-chloro-5-[1-(S)-hydroxypropyl]}phenylpiperazine in 90 ml of chloroform under cooling with ice. The obtained mixture was stirred as such for 2 hours. 90 ml of carbon tetrachloride was added to the reaction mixture to precipitate a salt, which was filtered out. 80 ml of water was added to the filtrate to conduct partition. The organic phase was washed with a brine and distilled to remove the solvent. The obtained residue was purified by silica gel chromatography to give 11.2 g of the title compound (yield: 62%, optical purity: 55% ee).
<Method for the determination of optical purity>
   The optical purity was determined under the same conditions as those described above.
<Retention time>
   S isomer: 17 to 19 min.
   R isomer: 20 to 21 min.

Example 244

Synthesis of 1-(t-butoxycarbonyl)-4-{3-bromo-4-chloro-5-[1-(R)-fluoropropyl]}phenylpiperazine A solution of 15.0 g (34.6 mmol) of 1-(t-butoxycarbonyl)-4-{3-bromo-4-chloro-5-[1-(S)-hydroxypropyl]} phenylpiperazine in 30 ml of methylene chloride was dropwise added to a solution of 6.15 g (38.0 mmol) of diethylaminosulfur trifluoride in 15 ml of methylene chloride at −70° C. The resulting mixture was stirred as such for one hour, brought to room temperature and neutralized with a saturated aqueous solution of sodium hydrogen carbonate. The resulting mixture was extracted with methylene chloride. The organic phase was washed with water and distilled to remove the solvent. The residue was purified by silica gel chromatography to give 12.5 g of the title compound (yield: 83%, optical purity: 34% ee).
<Method for the determination of optical purity>
   The optical purity was determined under the same conditions as those described above.

Example 245

Synthesis of 1-{3-bromo-4-chloro-5-[1-(R)-fluoropropyl]}phenylpiperazine

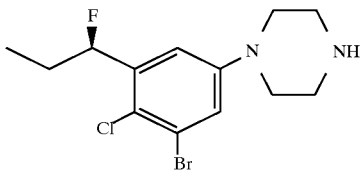

A solution of 6.75 g (68.8 mmol) of concentrated sulfuric acid in 25 ml of ethanol was added to a solution of 15.0 g (34.4 mmol) of 1-(t-butoxycarbonyl)-4-{3-bromo-4-chloro-5-[1-(R)-fluoropropyl]}phenylpiperazine in 50 ml of ethanol. The obtained mixture was stirred at 50° C. for 3 hours and then concentrated under reduced pressure. Ethyl acetate and a 5N aqueous solution of sodium hydroxide were added to the obtained residue to conduct partition. The organic phase was washed with a brine and distilled to remove the solvent, giving 10.3 g of the title compound (yield: 89%).
<Method for the determination of optical purity>
   The optical purity was determined under the same conditions as those described above.
<Retention time>
   S isomer: 17 to 19 min.
   R isomer: 20 to 21 min.

Example 246

Synthesis of 1-{3-(2-cyanophenyl)-4-chloro-5-[1-(R)-fluoropropyl]}phenylpiperazine

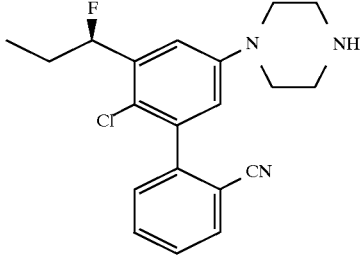

14.0 g (41.7 mmol) of 1-{3-bromo-4-chloro-5-[1-(R)-fluoropropyl]}phenylpiperazine, 2.4 g (2.08 mmol) of tetrakis(triphenylphosphine)palladium and 13.3 g (62.6 mmol) of anhydrous tripotassium phosphate were suspended in 28 ml of DMF, followed by the dropwise addition of a solution of 9.5 g (50.0 mmol) of 2-(1,3,2-dioxaborinan-2-yl)benzonitrile in 19 ml of DMF at 100° C. The obtained mixture was stirred as such for 3 hours and then cooled to room temperature. Water and ethyl acetate were added to the resulting mixture to conduct-partition. The organic phase was washed with a brine and distilled to remove the solvent. The obtained residue was purified by silica gel chromatography to give 10.6 g of the title compound (yield: 71%).
<Method for the determination of optical purity>
   The optical purity was determined under the same conditions as those described above.
<Retention time>
   S isomer: 10 to 12 min.
   R isomer: 12 to 14 min.

Example 247

Optical purification of 1-{3-(2-cyanophenyl)-4-chloro-5-[1-(R)-fluoropropyl]}phenylpiperazine A solution of 4.0 g (10.5 mmol) of (+)-di-p-toluoyl-D-tartaric acid in 100 ml of methanol was added to a solution of 10.0 g (27.9 mmol, 55% ee) of the title compound prepared in the above Example in 300 ml of methanol at room temperature. After the precipitation of a crystal, the resulting mixture was stirred under cooling with ice for one hour and then filtered to recover the crystal. The crystal was neutralized with a 5N aqueous solution of sodium hydroxide and the resulting mixture was extracted with ethyl acetate. The organic phase was washed with a brine and distilled to remove the solvent, giving 6.4 g of the title compound as an optically active substance (yield: 64%, optical purity: 90% ee).

<Method for the determination of optical purity>

The optical purity was determined under the same conditions as those described above.

Example 248

Synthesis of 1-(2-hydroxyethyl)-4-{3-(2-cyanophenyl)-4-chloro-5-[1-(R)-fluoropropyl]}phenylpiperazine hydrochloride

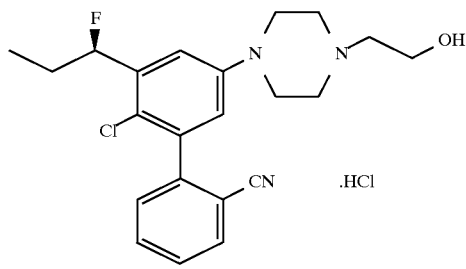

2.8 g (28.0 mmol) of triethylamine and 3.5 g (28.0 mmol) of 2-bromoethanol were added to a solution of 5.0 g (14.0 mmol) of the optically active 1-{3-(2-cyanophenyl)-4-chloro-5-[1-(R)-fluoropropyl]}phenylpiperazine prepared in the above Example in 10 ml of DMF. The obtained mixture was stirred at 50° C. for 3 hours and then cooled to room temperature. Water and toluene were added to the resulting mixture to conduct partition. The organic phase was washed with water and distilled to remove the solvent, giving 5.5 g of the title compound as a crude product (yield: 98%).

A solution of 5.5 g (13.7 mmol) of this crude product in 55 ml of 3% methanol/ethanol was dropwise added to a solution of 1.52 g (15.1 mmol) of concentrated hydrochloric acid in 27.5 ml of ethanol at 60° C. After the completion of the dropwise addition, the resulting mixture was stirred while cooled by allowing to stand. After the precipitation of a crystal, the resulting mixture was further stirred under cooling with ice for one hour and filtered to recover the crystal. Thus, 5.2 g of the title compound (i.e., a hydrochloride) was obtained (yield: 86%).

The compounds of the present invention were subjected to each of serotonin $S_2$ receptor binding test, dopamine $D_2$ receptor binding test and adrenergic $\alpha_1$ receptor binding test. The methods and results, which exhibit the effect of the present invention, will be given hereinafter.

<Method>

1. Reagent

The following reagents were used in this test.

(1) Methylsergide maleate (a product of RBI)

(2) Spiperone (a product of Sigma)

(3) Phentolamine (a product of Sigma)

Further, the following reagents (all of which are products of NEN) were used as radioisotope-labeled compounds.

(4) Ketanserin hydrochloride [ethylene-$^3$H]

(5) Spiperone [benzene ring-$^3$H]

(6) Prazosin [7-methoxy-$^3$H]

These reagents and samples were each dissolved in 10% ethanol before use. Among them, water-insoluble compounds were each dissolved in ethanol and the obtained solution was diluted with distilled water to an ethanol concentration of 10%. Further, Methylsergide maleate was used in a state dissolved in distilled water.

2. Animal

SD rats aged 6 to 8 weeks were used.

3. Preparation of receptor sources

SD rats were each slaughtered with a guillotine to extirpate its cerebrum. The cortex and corpus striatum were separated from the cerebrum. The former was used in serotonin $S_2$ receptor binding test and adrenergic $\alpha_1$ receptor binding test, while the latter was used in dopamine $D_2$ receptor binding test.

The cortex was homogenized in a 0.32M sucrose solution in an amount ten times the wet weight of the cortex by the use of a teflon glass homogenizer and the resulting mixture was cetrifuged at 10,000×G for 20 minutes. The obtained sediment was suspended in 50 mM Tris hydrochloride (pH 7.4) in an amount ten times the initial wet weight of the cortex by the use of a histocothrom, and the obtained suspension was centrifuged at 10,000×G for 20 minutes. This operation was repeated twice. The obtained sediment was suspended in 50 mM Tris hydrochloride (pH 7.4) in an amount 20 times the initial wet weight of the cortex by the use of a histocothrom. The suspension thus prepared was used as a receptor fraction. This receptor fraction was stored at −80° C. until use.

On the other hand, the corpus striatum was homogenized in a 0.32M sucrose solution in an amount ten times the wet weight of the corpus striatum by the use of a teflon glass homogenizer and the obtained mixture was centrifuged at 1,000×G for 20 minutes. The obtained supernatant was centrifuged at 10,000×G for 20 minutes. The obtained sediments were suspended together in 50 mM Tris hydrochloride (pH 7.4) in an amount ten times the initial wet weight of the corpus striatum by the use of a histocothrom, and the obtained suspension was centrifuged at 10,000×G for 20 minutes. This operation was repeated thrice. The resulting sediment was suspended in 50 mM Krebs-Tris (pH 7.4) in an amount 100 times the initial wet weight of the corpus striatum by the use of a histocothrom. The obtained suspension was used as a receptor fraction. This receptor fraction was stored at −80° C. until use.

4. [$^3$H] Ketanserin binding test

The receptor fraction prepared from the cortex was molten and suspended by the use of a histocothrom. The resulting suspension was incubated together with 1 nM-[$^3$H] Ketanserin at 37° C. for 15 minutes. The resulting reaction system was filtered through a Whatman GF/B glass filter with an MR-30R type cell harvester mfd. by Blandel. The resulting filter was washed twice with 5 ml of 50 mM Tris hydrochloride (pH 7.4) cooled with ice and the radioactivity of the Ketanserin bound the receptor was determined by the use of a liquid scintillation counter with 5 ml of ACS II. The binding detected in the presence of 1 μl of Methylsergide was regarded as nonspecific binding.

Each $IC_{50}$ value was calculated by the probit method and each Ki value was determined by the following formula:

$$Ki = \frac{IC_{50}}{1 + C/Kd}.$$

In the above formula, C represents the concentration of radioligand, and Kd represents the affinity of radioligand for the receptor as determined by the Scatchard analysis.

5. [³H] Spiperone binding test

This test was conducted in the same manner as that of the binding test of [³H] Ketanserin except that the receptor fraction prepared from the corpus striatum was molten and suspended with a histocothrom, and the obtained suspension was incubated together with 1 nM-[³H] Spiperone at room temperature for 60 minutes and that the binding detected in the presence of 10 μl of Spiperone was regarded as nonspecific binding.

6. [³H] Prazosin binding test

This test was conducted in the same manner as that of the binding test of [³H] Ketanserin except that the receptor fraction prepared from the cortex was molten and suspended with a histocothrom, and the obtained suspension was incubated together with 1 nM-[³H] Prazosin at room temperature for 60 minutes and that the binding detected in the presence of 10 μl of Phentolamine was regarded as nonspecific binding.

<Result>

The results of the evaluation of compounds according to the present invention are given in Tables 1 to 8.

TABLE 1

| | Ki value (nM) | | |
|---|---|---|---|
| Ex. | serotonin $S_2$ receptor | dopamine $D_2$ receptor | adrenergic $\alpha_1$ receptor |
| 13 | 24.9 | 4.05 | 404 |
| 17 | 374 | >100 | 550 |
| 18 | 6.15 | 0.75 | 53.7 |
| 19 | 1.95 | 0.64 | 81.6 |
| 20 | 6.11 | 2.82 | 313.6 |
| 21 | 14.4 | 1.85 | 418 |
| 22 | 19.2 | 2.84 | 809 |
| 23 | 51.2 | 7.22 | — |
| 24 | 40.9 | 3.60 | 537 |
| 25 | 8.27 | 2.40 | >1000 |
| 26 | 21.6 | 2.67 | >1000 |
| 27 | 10.9 | 11.2 | 455 |
| 28 | 5.67 | 1.60 | 50.8 |
| 29 | 4.86 | 1.19 | 50.1 |
| 30 | 2.24 | 0.86 | 92.5 |
| 31 | 12.4 | 0.69 | 36.1 |
| 32 | 3.36 | 0.38 | 19.5 |
| 33 | 6.46 | 2.02 | 86.9 |
| 34 | 7.77 | 0.37 | 25.8 |
| 35 | 3.37 | 0.50 | 17.0 |
| 36 | 4.04 | 1.26 | 25.3 |
| 40 | 3.64 | 9.25 | >1000 |

TABLE 2

| | Ki value (nM) | | |
|---|---|---|---|
| Ex. | serotonin $S_2$ receptor | dopamine $D_2$ receptor | adrenergic $\alpha_1$ receptor |
| 45 | 192 | 26.9 | 183 |
| 46 | 2.16 | 9.78 | >1000 |
| 47 | 5.72 | 12.9 | >1000 |
| 48 | 4.32 | 25.8 | >1000 |
| 49 | 20.1 | 6.09 | >1000 |
| 50 | 17.7 | 9.14 | >1000 |
| 51 | 164 | 27.2 | >1000 |
| 52 | 21.6 | 0.99 | >1000 |
| 53 | 12.4 | 6.73 | >1000 |
| 54 | 37.5 | 6.06 | >1000 |
| 55 | 113.04 | 3.10 | >1000 |

TABLE 3

| | Ki value (nM) | | |
|---|---|---|---|
| Ex. | serotonin $S_2$ receptor | dopamine $D_2$ receptor | adrenergic $\alpha_1$ receptor |
| 56 | 212 | 111 | 503 |
| 57 | >1000 | >1000 | >1000 |
| 58 | >1000 | >1000 | 290 |
| 59 | 36.7 | 47.0 | 301 |
| 60 | >1000 | >1000 | >1000 |
| 61 | >1000 | >1000 | >1000 |
| 62 | >1000 | >1000 | >1000 |
| 63 | 703 | >1000 | >1000 |
| 64 | 284 | 384 | 459 |
| 65 | 26.6 | 6.60 | 79.0 |
| 66 | 65.9 | 18.3 | 127 |
| 67 | >1000 | >1000 | 687 |
| 68 | 32.0 | 35.1 | 195 |
| 69 | 67.1 | 171 | 321 |
| 70 | 128 | 41.9 | 322 |
| 71 | 90.9 | 14.7 | 131 |
| 72 | 108 | 50.3 | 270 |
| 73 | 635 | 577 | 332 |
| 74 | 374 | >1000 | >1000 |
| 75 | 486 | >1000 | >1000 |
| 76 | 145 | 50.1 | 112 |
| 77 | 24.3 | 40.0 | 182 |
| 78 | 33.2 | 4.22 | 74.8 |
| 79 | 192 | 28.5 | 69.8 |
| 80 | 177 | 810 | >1000 |

TABLE 4

| | Ki value (nM) | | |
|---|---|---|---|
| Ex. | serotonin $S_2$ receptor | dopamine $D_2$ receptor | adrenergic $\alpha_1$ receptor |
| 81 | 241 | 38.3 | >1000 |
| 82 | 10.7 | 39.1 | 723 |
| 83 | 84.5 | 485 | >1000 |
| 84 | 66.2 | 44.6 | >1000 |
| 85 | >1000 | >1000 | >1000 |
| 86 | 29.4 | 10.5 | >1000 |
| 87 | 283 | 135 | >1000 |
| 88 | 8.33 | 7.35 | 493 |
| 89 | 310 | 44.6 | >1000 |
| 90 | 685 | 263 | >1000 |
| 91 | 37.1 | 7.34 | 323 |
| 92 | 1.14 | 2.71 | 942 |
| 93 | 1.31 | 28.0 | 719 |
| 94 | 109 | 13.8 | 600 |
| 95 | 40.9 | 104 | 279 |
| 96 | 35.3 | 1.33 | >1000 |
| 97 | 247 | >1000 | >1000 |
| 98 | 19.3 | 64.5 | >1000 |
| 99 | 170 | 2.93 | >1000 |
| 100 | 827 | 82.7 | 846 |
| 101 | 262 | 118 | >1000 |
| 102 | >1000 | >1000 | 525 |
| 103 | 6.65 | 101 | >1000 |
| 104 | 24.5 | 70.1 | >1000 |
| 105 | 5.21 | 30.2 | 620 |
| 106 | 380 | 44.0 | >1000 |
| 107 | >1000 | 429 | >1000 |
| 108 | 4.00 | 162 | 408 |
| 109 | 230 | >1000 | >1000 |
| 110 | >1000 | >1000 | >1000 |

TABLE 5

| Ex. | Ki value (nM) | | |
|---|---|---|---|
| | serotonin $S_2$ receptor | dopamine $D_2$ receptor | adrenergic $\alpha_1$ receptor |
| 111 | 58.0 | 41.9 | 210 |
| 112 | 7.00 | 972 | >1000 |
| 113 | 21.1 | 8.73 | 28.9 |
| 114 | 151 | 165 | 569 |
| 115 | 212 | 81.4 | >1000 |
| 116 | 39.5 | 9.65 | >1000 |
| 117 | 148 | 49.6 | 334 |
| 118 | 468 | 149 | >1000 |
| 119 | 34.9 | 35.8 | >1000 |
| 120 | 17.4 | 0.36 | 77.6 |
| 121 | 168 | 11.0 | 308 |
| 122 | 123 | 45.9 | 68.1 |
| 123 | 17.9 | 27.0 | >1000 |
| 124 | >1000 | 99.2 | >1000 |
| 125 | 1.49 | 101 | >1000 |
| 126 | 27.3 | 54.6 | >1000 |
| 127 | 11.4 | 1.04 | 65.9 |
| 128 | 1.16 | 46.1 | >1000 |
| 129 | 34.9 | 1.86 | 39.8 |
| 130 | 58.0 | 29.7 | 70.4 |
| 131 | 20.8 | 3.30 | >1000 |
| 132 | 392 | 281 | >1000 |
| 133 | 9.02 | 28.7 | >1000 |
| 134 | 30.3 | 59.7 | >1000 |
| 135 | 16.0 | 42.1 | >1000 |
| 136 | 89.0 | 14.2 | 472 |
| 137 | 144 | 0.64 | 312 |
| 138 | 25.0 | 2.89 | 9.33 |
| 139 | 5.38 | 2.34 | 68.7 |
| 140 | 26.2 | 2.97 | 95.5 |

TABLE 6

| Ex. | Ki value (nM) | | |
|---|---|---|---|
| | serotonin $S_2$ receptor | dopamine $D_2$ receptor | adrenergic $\alpha_1$ receptor |
| 141 | 92.7 | 24.9 | >1000 |
| 142 | 20.5 | 1.77 | 653 |
| 143 | 156 | 16.9 | >1000 |
| 144 | 15.7 | 0.81 | 67.4 |
| 145 | 72.5 | 8.28 | >1000 |
| 146 | 13.2 | 0.83 | 349 |
| 147 | 15.1 | 0.45 | 33.2 |
| 148 | 22.4 | 12.1 | 278 |
| 149 | 11.6 | 6.24 | 27.2 |
| 150 | 97.1 | 7.98 | >1000 |
| 151 | 27.7 | 3.52 | >1000 |
| 153 | 4.19 | 1.53 | 68.7 |
| 154 | 153 | 2.59 | >1000 |
| 155 | 179.6 | 41.0 | 845.0 |
| 156 | 29.0 | 1.39 | 513.4 |
| 157 | 74.4 | 7.26 | >1000 |
| 158 | 124 | 12.4 | >1000 |
| 159 | 8.81 | 3.93 | 596 |
| 160 | 14.8 | 13.6 | >1000 |
| 161 | 22.5 | 9.80 | 776 |
| 162 | 6.15 | 0.75 | 53.7 |
| 163 | 63.6 | 10.2 | 195 |
| 164 | 12.0 | 1.62 | >1000 |
| 165 | 6.10 | 0.74 | >1000 |
| 166 | 5.42 | 1.42 | >1000 |
| 167 | 23.8 | 45.4 | >1000 |
| 168 | 180 | 31.9 | >1000 |
| 169 | 108 | 41.8 | >1000 |
| 170 | 2.77 | 34.2 | >1000 |

TABLE 7

| Ex. | Ki value (nM) | | |
|---|---|---|---|
| | serotonin $S_2$ receptor | dopamine $D_2$ receptor | adrenergic $\alpha_1$ receptor |
| 171 | 2.74 | 86.7 | >1000 |
| 172 | 30.3 | 48.9 | >1000 |
| 173 | >1000 | 19.2 | >1000 |
| 174 | 48.7 | 31.8 | >1000 |
| 175 | >100 | 29.32 | >1000 |
| 176 | 178 | >100 | >1000 |
| 177 | >100 | >100 | >1000 |
| 178 | 12.2 | 7.30 | >1000 |
| 179 | 6.54 | 6.08 | 72.7 |
| 180 | 3.48 | 13.0 | >100 |
| 181 | 0.50 | 26.2 | >100 |
| 182 | 145 | 2.34 | 186 |
| 183 | 81.2 | 165 | >1000 |
| 184 | 2.09 | 0.17 | 4.52 |
| 185 | >100 | 0.58 | >1000 |
| 186 | 4.29 | 2.96 | >1000 |
| 187 | 38.2 | 0.54 | 7.80 |
| 188 | 47.8 | 1.33 | 19.0 |
| 189 | >100 | 1.51 | 32.5 |
| 190 | 18.5 | 40.4 | >1000 |
| 191 | 3.76 | 1.65 | 21.2 |
| 192 | 374 | >100 | 550 |
| 193 | 1.61 | 19.3 | 585 |
| 194 | 4.45 | 0.83 | >1000 |
| 195 | 5.75 | 70.6 | >1000 |
| 196 | 13.2 | 5.52 | 744 |
| 197 | 8.86 | 1.40 | 31.4 |
| 198 | 1.06 | 12.1 | 62.7 |
| 199 | 63.2 | 51.5 | — |
| 200 | — | — | — |

TABLE 8

| Ex. | Ki value (nM) | | |
|---|---|---|---|
| | serotonin $S_2$ receptor | dopamine $D_2$ receptor | adrenergic $\alpha_1$ receptor |
| 201 | 3.17 | 19.7 | 12.9 |
| 202 | 6.33 | 90.5 | — |
| 203 | 54.8 | — | — |
| 204 | 187 | 14.4 | — |
| 205 | 51.2 | 2.83 | — |
| 206 | 4.29 | 1.06 | 47.8 |
| 207 | 81.1 | 240.3 | >1000 |
| 208 | 16.1 | 3.46 | 2379 |
| 209 | 42.7 | 3.90 | — |
| 210 | 6.25 | 16.1 | — |
| 211 | 8.81 | 4.14 | 1024 |
| 212 | 1019 | 3.90 | — |
| 213 | 10.3 | 14.3 | 236 |
| 214 | 3.78 | 5.15 | 51.7 |
| 215 | 15.3 | 2.28 | — |
| 216 | 79.0 | 11.3 | — |
| 217 | 25.5 | 3.57 | — |
| 218 | 30.1 | 5.39 | — |
| 219 | 151 | 5.54 | — |
| 220 | 37.9 | 1.25 | 1680 |
| 221 | 4.53 | 3.45 | 486 |
| 222 | 12.0 | 6.50 | 1040 |
| 223 | 1860 | 6.61 | 1510 |
| risperidone | 0.62 | 5.03 | 2.94 |

It can be understood from the results of the Tables 1 to 8 that the biphenyl derivative of the present invention exhibits excellent therapeutic and ameliorative effects on mental disorders such as cerebrovascular disorder, aggressive behavior due to senile dementia, mental excitation, poriomania, delirium, hallucination, hyperkinesia, schizophrenia, emotional disturbance, depression, neurosis, psychophysiologic disorder and anxiety neurosis.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim is:

1. A biphenyl compound represented by the following formula (I) or a pharmacologically acceptable salt thereof:

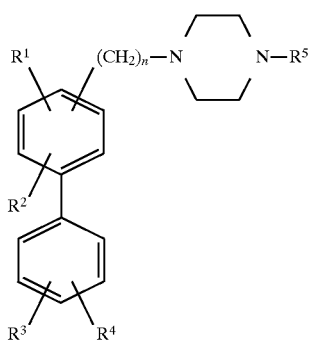

wherein $R^1$ is a halogenated lower alkyl group or a lower alkylsulfonylamino group; $R^2$ is a halogen atom or a lower alkoxy group; $R^3$ is a halogen atom, a lower alkyl group or a cyano group; $R^4$ is a hydrogen atom or a halogen atom; $R^5$ is a hydrogen atom, a lower alkyl group or a hydroxy lower alkyl group; and n is 0.

2. The biphenyl compound or a pharmacologically acceptable salt thereof which is a compound selected from the group consisting of (1) 1-[3-(2-cyanophenyl)-4-chloro-5-(1-fluoropropyl)]phenylpiperazine,
(2) 1-(2-hydroxyethyl)-4-[3-(2-cyanophenyl)-4-chloro-5-(1-fluoropropyl)]phenylpiperazine,
(3) 1-ethyl-4-[3-(2-tolyl)-4-chloro-5-ethoxycarbonyl]phenylpiperazine,
(4) 1-ethyl-4-[3-(2-tolyl)-4-chloro-5-amino]phenylpiperazine,
(5) 1-ethyl-4-[3-(2-tolyl)-4-chloro-5-propanesulfonylamino]phenylpiperazine,
(6) 1-ethyl-4-[3-(2-tolyl)-4-chloro-5-ethanesulfonylamino]phenylpiperazine,
(7) 1-ethyl-4-[3-(2-tolyl)-4-chloro-5-butanesulfonylamino]phenylpiperazine,
(8) 1-methyl-4-[3-(2-cyanophenyl)-4-chloro-5-(1-fluoropropyl)]phenylpiperazine,
(9) 1-ethyl-4-[3-(2-cyanophenyl)-4-chloro-5-(1-fluoropropyl)]phenylpiperazine,
(10) 1-methyl-4-[3-(2-chlorophenyl)-4-chloro-5-(1-fluoropropyl)]phenylpiperazine,
(11) 1-(2-hydroxyethyl)-4-[3-(2-chlorophenyl)-4-chloro-5-(1-fluoropropyl)]phenylpiperazine,
(12) 1-ethyl-4-[3-(2-chlorophenyl)-4-chloro-5(1-fluoropropyl)]phenylpiperazine,
(13) 1-methyl-4-[3-(2-tolyl)-4-chloro-5-(1-fluoropropyl)]phenylpiperazine,
(14) 1-(2-hydroxyethyl)-4-[3-(2-tolyl)-4-chloro-5-(1-fluoropropyl)]phenylpiperazine,
(15) 1-ethyl-4-[3-(2-tolyl)-4-chloro-5-(1-fluoropropyl)]phenylpiperazine,
(16) 1-methyl-4-[3-(2-tolyl)-4-chloro-5-ethanesulfonylamino]phenylpiperazine,
(17) 1-methyl-4-[3-(2-tolyl)-4-chloro-5-propanesulfonylamino]phenylpiperazine,
(18) 1-methyl-4-[3-(2-tolyl)-4-chloro-5-butanesulfonylamino]phenylpiperazine,
(19) 1-ethyl-4-[3-(2-chlorophenyl)-4-chloro-5-ethanesulfonylamino]phenylpiperazine,
(20) 1-ethyl-4-[3-(2-chlorophenyl)-4-chloro-5-propanesulfonylamino]phenylpiperazine,
(21) 1-ethyl-4-[3-(2-chlorophenyl)-4-chloro-5-butanesulfonylamino]phenylpiperazine,
(22) 1-methyl-4-[3-(2-chlorophenyl)-4-chloro-5-ethanesulfonylamino]phenylpiperazine,
(23) 1-methyl-4-[3-(2-chlorophenyl)-4-chloro-5-propanesulfonylamino]phenylpiperazine,
(24) 1-methyl-4-[3-(2-chlorophenyl)-4-chloro-5-butanesulfonylamino]phenylpiperazine,
(25) 1-ethyl-4-[3-(4-fluorophenyl)-4-methoxy-5-ethanesulfonylamino]phenylpiperazine,
(26) 1-ethyl-4-(3-phenyl-4-methoxy-5-chloromethyl)phenylpiperazine,
(27) 1-ethyl-4-{3-phenyl-4-methoxy-5-[1-fluoro-(4-pentenyl)]}phenylpiperazine,
(28) 1-ethyl-4-[3-phenyl-4-methoxy-5-(1-fluorobutyl)]phenylpiperazine,
(29) 1-ethyl-4-[3-phenyl-4-methoxy-5-(1-fluoropentyl)]phenylpiperazine,
(30) 1-ethyl-4-[3-(2-tolyl)-4-chloro-5-(1-fluorobutyl)]phenylpiperazine,
(31) 1-ethyl-4-[3-(2-tolyl)-4-fluoro-5-(1-fluorobutyl)]phenylpiperazine,
(32) 1-ethyl-4-[3-(2-tolyl)-4-chloro-5-(1-fluoro-3-methylbutyl)]phenylpiperazine,
(33) 1-ethyl-4-[3-(2-tolyl)-4-chloro-5-(1-fluoroethyl)]phenylpiperazine,
(34) 1-methyl-4-[3-(2-tolyl)-4-chloro-5-(1-fluorobutyl)]phenylpiperazine,
(35) 1-ethyl-4-[3-(2-chlorophenyl)-4-chloro-5-(1-fluorobutyl)]phenylpiperazine,
(36) 1-ethyl-4-[3-(2-tolyl)-4-chloro-5-(1,1-difluoropropyl)]phenylpiperazine,
(37) 1-ethyl-4-(3,5-diphenyl-4-methoxy)phenylpiperazine,
(38) 1-ethyl-4-(3-phenyl-4-methoxy)phenylpiperazine,
(39) 1-ethyl-4-(3,5-diphenyl-4-hydroxy)phenylpiperazine,
(40) 1-ethyl-4-(3-phenyl-4-methoxy-5-propyl)phenylpiperazine,
(41) 1-ethyl-4-(3,5-diphenyl-4-isopropoxy)phenylpiperazine,
(42) 1-ethyl-4-(3-phenyl-4-isopropoxy)phenylpiperazine,
(43) 1-ethyl-4-(3-phenyl-4-hydroxy)phenylpiperazine,
(44) 1-ethyl-4-[2-methoxy-3-phenyl-5-(3-hydroxypropyl)]phenylpiperazine,
(45) 1-hydroxyethyl-4-(3,5-diphenyl-4-methoxy)phenylpiperazine,
(46) 1-ethyl-4-[3-(4-fluorophenyl)-4-methoxy-5-propyl)]phenylpiperazine,
(47) 1-ethyl-4-[3-phenyl-4-methoxy-5-(2-hydroxyethyl)]phenylpiperazine,
(48) 1-ethyl-4-[2-methoxy-3-phenyl-5-(2-hydroxyethyl)]phenylpiperazine,
(49) 1-ethyl-4-[3-phenyl-4-methoxy-5-(3-methoxypropyl)]phenylpiperazine,
(50) 1-ethyl-4-[3-phenyl-4-methoxy-5-(3-methoxymethoxypropyl)]phenylpiperazine,
(51) 1-ethyl-4-(3-phenyl-4-methoxy-5-ethyl)phenylpiperazine,
(52) 1-ethyl-4-[3-phenyl-4-methoxy-5-(3-cyanopropyl)]phenylpiperazine,
(53) 1-(2-fluoroethyl)-4-[3-(4-fluorophenyl)-4-methoxy-5-propyl]phenylpiperazine,
(54) 1-ethyl-4-[3-(4-methoxyphenyl)-4-methoxy-5-propyl]phenylpiperazine,
(55) 1-ethyl-4-(3-phenyl-4-methoxy-5-methoxycarbonyl)phenylpiperazine,

(56) 1-ethyl-4-[3-phenyl-4-methoxy-5-(2-hydroxypropyl)]phenylpiperazine,
(57) 1-ethyl-4-[3-phenyl-4-methoxy-5-(2-fluoroethyl)]phenylpiperazine,
(58) 1-ethyl-4-[3-phenyl-4-methoxy-5-(3-fluoropropyl)]phenylpiperazine,
(59) 1-ethyl-4-[3-(4-fluorophenyl)-4-methoxy-5-isopropyl]phenylpiperazine,
(60) 1-ethyl-4-[3-(4-fluorophenyl)-4-methoxy-6-isopropyl]phenylpiperazine,
(61) 1-ethyl-4-[3-phenyl-4-methoxy-5-(1-hydroxyisopropyl)]phenylpiperazine,
(62) 1-ethyl-4-[3-phenyl-4-methoxy-5-(1-butoxypropyl)]phenylpiperazine,
(63) 1-ethyl-4-(3-phenyl-4-methoxy-5-propionyl)phenylpiperazine,
(64) 1-ethyl-4-[3-phenyl-4-methoxy-5-(1-hydroxypropyl)]phenylpiperazine,
(65) 1-ethyl-4-[3-(2-fluorophenyl)-4-methoxy-5-propyl]phenylpiperazine,
(66) 1-ethyl-4-[3-(4-trifluoromethylphenyl)-4-methoxy-5-propyl]phenylpiperazine,
(67) 1-ethyl-4-[3-phenyl-4-methoxy-5-(1-fluoroisopropyl)]phenylpiperazine,
(68) 1-ethyl-4-[3-phenyl-4-methoxy-5-(2-hydroxyisopropyl)]phenylpiperazine,
(69) 1-ethyl-4-[3-phenyl-4-methoxy-5-(1-fluoropropyl)]phenylpiperazine,
(70) 1-ethyl-4-(3-phenyl-4-methoxy-5-cyano)phenylpiperazine,
(71) 1-ethyl-4-[3-phenyl-4-methoxy-5-(2-furanyl)]phenylpiperazine,
(72) 1-ethyl-4-[3-(2,4-difluorophenyl)-4-methoxy-5-propyl]phenylpiperazine,
(73) 1-ethyl-4-(3-phenyl-4-methoxy-5-phenylacetyl)phenylpiperazine,
(74) 1-ethyl-4-[3-phenyl-4-methoxy-5-(4-fluorophenyl)acetyl]phenylpiperazine,
(75) 1-ethyl-4-[3-phenyl-4-methoxy-5-(1-hydroxyphenethyl)]phenylpiperazine,
(76) 1-ethyl-4-[3-phenyl-4-methoxy-5-(2-tetrahydrofuranyl)]phenylpiperazine,
(77) 1-ethyl-4-[3-phenyl-4-methoxy-5-(1-fluorophenethyl)]phenylpiperazine,
(78) 1-ethyl-4-[3-phenyl-4-methoxy-5-(2-pyridyl)]phenylpiperazine,
(79) 1-ethyl-4-{3-phenyl-4-methoxy-5-[4-fluoro-(1hydroxyimino)phenethyl]}phenylpiperazine,
(80) 1-ethyl-4-{3-phenyl-4-methoxy-5-[1-fluoro-2-(2-pyridyl)ethyl]}phenylpiperazine,
(81) 1-ethyl-4-[3-phenyl-4-methoxy-5-(1-propenyl)]phenylpiperazine,
(82) 1-ethyl-4-[3-(3-fluorophenyl)-4-methoxy-5-propyl]phenylpiperazine,
(83) 1-ethyl-4-(3-phenyl-4-methoxy-5-hydroxymethyl)phenylpiperazine,
(84) 1-ethyl-4-[3-phenyl-4-methoxy-5-(4-pyridyl)acetyl]phenylpiperazine,
(85) 1-ethyl-4-(3-phenyl-4-methoxy-5-methanesulfinyl)phenylpiperazine,
(86) 1-ethyl-4-(3-phenyl-4-methoxy-5-ethanesulfinyl)phenylpiperazine,
(87) 1-ethyl-4-(3-phenyl-4-methoxy-5-formyl)phenylpiperazine,
(88) 1-ethyl-4-[3-phenyl-4-methoxy-5-(1,3-dioxan-2-yl)]phenylpiperazine,
(89) 1-ethyl-4-(3-phenyl-4-methoxy-5-cyclopropaneacetyl)phenylpiperazine,
(90) 1-ethyl-4-[3-phenyl-4-methoxy-5-(2-pyridylcarbonyl)]phenylpiperazine,
(91) 1-ethyl-4-(3-phenyl-4-methoxy-5-amino)phenylpiperazine,
(92) 1-ethyl-4-[3-phenyl-4-methoxy-5-(2-ethoxycarbonylethyl)]phenylpiperazine,
(93) 1-ethyl-4-[3-phenyl-4-methoxy-5-(2-pyridyl)hydroxymethyl]phenylpiperazine,
(94) 1-ethyl-4-(3-phenyl-5-propyl-6-methoxy)phenylpiperazine,
(95) 1-ethyl-4-[3-phenyl-4-methoxy-5-(2-acetylethyl)]phenylpiperazine,
(96) 1-ethyl-4-{3-phenyl-4-methoxy-5-[1-(2-pyridylmethoxy)propyl]}phenylpiperazine,
(97) 1-ethyl-4-[3-(2-tolyl)-4-methoxy-5-propyl]phenylpiperazine,
(98) 1-ethyl-4-(3-phenyl-4-methoxy-5-propylamino)phenylpiperazine,
(99) 1-(3-phenyl-4-hydroxy-5-phenylacetyl)phenylpiperazine,
(100) 1-ethyl-4-(3-phenyl-4-methoxy-5-benzylsulfinyl)phenylpiperazine,
(101) 1-ethyl-4-(3-phenyl-4-methoxy-5-benzenesulfonylamino)phenylpiperazine,
(102) 1-ethyl-4-{3-phenyl-4-methoxy-5-[1-fluoro-2-(4-pyridyl)ethyl]}phenylpiperazine,
(103) 1-ethyl-4-[3-phenyl-4-methoxy-5-(N-ethanesulfonyl-N-methylamino)]phenylpiperazine,
(104) 1-ethyl-4-(3-phenyl-4-methoxy-5-ethylaminosulfonyl)phenylpiperazine,
(105) 1-ethyl-4-(3-phenyl-4-methoxy-5-aminosulfonyl)phenylpiperazine,
(106) 1-(3-phenyl-4-methoxy-5-phenylacetyl)phenylpiperazine,
(107) 1-benzyl-4-(3-phenyl-4-methoxy-5-phenylacetyl)phenylpiperazine,
(108) 1-ethyl-4-[3-phenyl-4-chloro-5-(1-fluoropropyl)]phenylpiperazine,
(109) 1-hydroxyethyl-4-(3-phenyl-4-methoxy-5-phenylacetyl)phenylpiperazine,
(110) 1-ethyl-4-[3-phenyl-5-(1-fluoropropyl)]phenylpiperazine,
(111) 1-ethyl-4-(3-phenyl-5-propionyl)phenylpiperazine,
(112) 1-ethyl-4-[3-(2-tolyl)-4-chloro-5-(1-fluoropropyl)]phenylpiperazine,
(113) 1-ethyl-4-[3-(2-methoxyphenyl)-4-methoxy-5-propyl]phenylpiperazine,
(114) 1-ethyl-4-(3-phenyl-4-methoxy-5-ethanesulfonyl)phenylpiperazine,
(115) 1-ethyl-4-(3-phenyl-4-methoxy-5-dimethylaminosulfonyl)phenylpiperazine,
(116) 1-ethyl-4-[3-phenyl-4-methoxy-5-(1-pyrrolidinylsulfonyl)]phenylpiperazine,
(117) 1-ethyl-4-[3-(2-tolyl)-4-chloro-5-(2,2,2-trifluoroethyl)sulfonylamino]phenylpiperazine,
(118) 1-ethyl-4-[3-(2-tolyl)-4-chloro-5-(4-fluorophenylsulfonylamino)]phenylpiperazine,
(119) 1-ethyl-4-[3-phenyl-4-chloro-5-(1-hydroxypropyl)]phenylpiperazine,
(120) 1-ethyl-4-(3-phenyl-4-chloro-5-ethanesulfonyl)phenylpiperazine,
(121) 1-ethyl-4-(3-phenyl-4-chloro-5-propionyl)phenylpiperazine,
(122) 1-ethyl-4-[3-(2-tolyl)-4-chloro-5-(1-pyrrolidylsulfonyl)]phenylpiperazine,
(123) 1-ethyl-4-{3-[2-(4-fluorotolyl)]-4-chloro-5-(1-fluoropropyl)}phenylpiperazine, (124) 1-ethyl-4-[3-(2-methoxyphenyl)-4-chloro-5-(1-fluoropropyl)]phenylpiperazine,
(125) 1-ethyl-4-[3-(2,4-difluorophenyl)-4-chloro-5-(1-fluoropropyl)]phenylpiperazine,
(126) 1-ethyl-4-[3-(2-methoxymethylphenyl)-4-chloro-5-(1-fluoropropyl)]phenylpiperazine,
(127) 1-ethyl-4-{3-[2-(4-fluorotolyl)]-4-chloro-5-cyclopropaneaminosulfonyl}phenylpiperazine,
(128) 1-ethyl-4-[3-phenyl-4-chloro-5-(1-methylpropyl)]phenylpiperazine,
(129) 1-ethyl-4-{3-[2-(4-fluorotolyl)]-4-chloro-5-cyclopropylmethylsulfonyl}phenylpiperazine,
(130) 1-ethyl-4-(3-phenyl-4-fluoro-5-ethanesulfonyl)phenylpiperazine,
(131) 1-[3-(4-pyridyl)propyl]-4-[3-(2-tolyl)-4-chloro-5-(1-fluoropropyl)]phenylpiperazine,
(132) 1-propyl-4-[3-(2-tolyl)-4-chloro-5-(1-fluoropropyl)]phenylpiperazine,
(133) 1-ethyl-4-[3-(2-hydroxymethylphenyl)-4-chloro-5-(1-fluoropropyl)]phenylpiperazine,
(134) 1-ethyl-4-[3-(2-tolyl)-4-chloro-5-propanesulfonylamino]phenylpiperazine,
(135) 1-ethyl-4-[3-(2-tolyl)-4-chloro-5-dimethylaminosulfonyl]phenylpiperazine,
(136) 1-ethyl-4-[3-(2-tolyl)-4-fluoro-5-methanesulfonyl]phenylpiperazine,
(137) 1-ethyl-4-[3-(2-chloro-4-fluorophenyl)-4-chloro-5-(1-fluoropropyl)]phenylpiperazine,
(138) 1-ethyl-4-[3-(2-tolyl)-4-chloro-5-(1-ethylpropyl)]phenylpiperazine,
(139) 1-ethyl-4-[3-(2-tolyl)-4-chloro-5-methanesulfonyl]phenylpiperazine,
(140) 1-ethyl-4-[3-(2-tolyl)-4-chloro-5-propanesulfonyl]phenylpiperazine,
(141) 1-ethyl-4-[3-(2-tolyl)-4-chloro-5-(1-fluoro-4-pentenyl)]phenylpiperazine,
(142) 1-ethyl-4-[3-(2-tolyl)-4-chloro-5-propylaminosulfonyl]phenylpiperazine,
(143) 1-ethyl-4-[3-(2-tolyl)-4-chloro-5-ethanesulfonylamino]phenylpiperazine,
(144) 1-ethyl-4-[3-(2-chlorophenyl)-4-chloro-5-(2,2,2-trifluoroethyl)sulfonylamino]phenylpiperazine,
(145) 1-ethyl-4-[3-(2-tolyl)-4-cyano-5-(1-fluoropropyl)]phenylpiperazine,
(146) 1-ethyl-4-[3-(2-tolyl)-4-chloro-5-(3-chloropropyl)sulfonylamino]phenylpiperazine,
(147) 1-ethyl-4-[3-(2-tolyl)-4-chloro-5-phenylaminosulfonyl]phenylpiperazine,
(148) 1-ethyl-4-[3-(2-tolyl)-4-chloro-5-benzyloxymethyl]phenylpiperazine,
(149) 1-ethyl-4-[3-(2-tolyl)-4-chloro-5-propoxymethyl]phenylpiperazine,
(150) 1-ethyl-4-[3-(2-tolyl)-4-chloro-5-(4-pyridyl)methoxymethyl]phenylpiperazine,
(151) 1-ethyl-4-(3-phenyl-4-methoxy-5-propanesulfonyl)phenylpiperazine,
(152) 1-ethyl-4-(3-phenyl-4-methoxy-5-butanesulfonyl)phenylpiperazine,
(153) 1-ethyl-4-[3-phenyl-4-methoxy-5-(2-fluoroethane)sulfonyl]phenylpiperazine,
(154) 1-ethyl-4-[3-(2-tolyl)-4-chloro-5-ethoxymethyl]phenylpiperazine,
(155) 1-methyl-4-[3-(2-tolyl)-4-chloro-5-(1-hydroxybutyl)]phenylpiperazine,
(156) 1-ethyl-4-[3-(2-tolyl)-4-chloro-5-allyloxymethyl]phenylpiperazine,
(157) 1-ethyl-4-[3-(2-tolyl)-4-chloro-5-cyclopropylmethoxymethyl]phenylpiperazine,
(158) 1-ethyl-4-[3-(2-tolyl)-4-chloro-5-(1-pyrrolidinyl)]phenylpiperazine,
(159) 1-methyl-4-[3-(2-chlorophenyl)-4-chloro-5-(1-fluorobutyl)]phenylpiperazine,
(160) 1-methyl-4-[3-(2-chlorophenyl)-4-chloro-5-benzylsulfonylamino]phenylpiperazine,
(161) 1-methyl-4-[3-(2-chlorophenyl)-4-chloro-5-propanesulfonyl]phenylpiperazine,
(162) 1-ethyl-4-{3-phenyl-4-methoxy-5-[3-(4-fluorophenoxy)propane]sulfonyl}phenylpiperazine,
(163) 1-methyl-4-[3-(2-chlorophenyl)-4-chloro-5-isopropylsulfonylamino]phenylpiperazine,
(164) 1-ethyl-4-[3-phenyl-4-methoxy-5-(2-cyanoethylsulfonyl)]phenylpiperazine,
(165) 1-ethyl-4-(3-phenyl-4-chloro-5-propanesulfonylamino)phenylpiperazine,
(166) 1-ethyl-4-[3-(2-tolyl)-4-chloro-5-difluoromethyl]phenylpiperazine,
(167) 1-ethyl-4-[3-phenyl-4-methoxy-5-(1,1-difluoropropyl)]phenylpiperazine,
(168) 1-ethyl-4-[3-(4-methoxyphenyl)-4-chloro-5-propanesulfonylamino]phenylpiperazine,
(169) 1-methyl-4-[3-(2-chlorophenyl)-4-chloro-5-methanesulfonylamino]phenylpiperazine,
(170) 1-ethyl-4-[3-(2,4-dichlorophenyl)-4-chloro-5-propanesulfonylamino]phenylpiperazine,
(171) 1-ethyl-4-[3-(2-tolyl)-4-chloro-5-(1,3-dithian-2-yl)]phenylpiperazine,
(172) 1-ethyl-4-[3-phenyl-4-chloro-5-propanesulfonyl]phenylpiperazine,
(173) 1-ethyl-4-[3-(2-tolyl)-4-chloro-5-propanesulfonylaminomethyl]phenylpiperazine,
(174) 1-methyl-4-[3-(4-fluorophenyl)-4-methoxy-5-propanesulfonyl]phenylpiperazine,
(175) 1-ethyl-4-[3-(2-ethylphenyl)-4-chloro-5-propanesulfonylamino]phenylpiperazine,
(176) 1-hydroxyethyl-4-[3-(4-fluorophenyl)-4-methoxy-5-ethanesulfonyl]phenylpiperazine,
(177) 1-ethyl-4-[3-(2-formylphenyl)-4-chloro-5-propanesulfonylamino]phenylpiperazine,
(178) 1-ethyl-4-[3-(2-cyanophenyl)-4-chloro-5-propanesulfonylamino]phenylpiperazine,
(179) 1-(2-pyridylethyl)-4-[3-(4-fluorophenyl)-4-methoxy-5-ethanesulfonyl]phenylpiperazine,
(180) 1-(2-pyridylmethyl)-4-[3-(4-fluorophenyl)-4-methoxy-5-ethanesulfonyl]phenylpiperazine,
(181) 1-(3-pyridylmethyl)-4-[3-(4-fluorophenyl)-4-methoxy-5-ethanesulfonyl]phenylpiperazine,
(182) 1-(4-pyridylethyl)-4-[3-(4-fluorophenyl)-4-methoxy-5-ethanesulfonyl]phenylpiperazine,
(183) 1-[3-(4-fluorophenyl)-4-methoxy-5-ethanesulfonyl]phenylpiperazine,
(184) 1-(2-fluoroethyl)-4-[3-(4-fluorophenyl)-4-methoxy-5-ethanesulfonyl]phenylpiperazine,
(185) 1-ethyl-4-[3-(2-chlorophenyl)-4-chloro-5-(1-propenyl)]phenylpiperazine,
(186) 1-ethyl-4-[3-(2-chlorophenyl)-4-chloro-5-(1-chloropropyl)]phenylpiperazine,
(187) 1-methyl-4-[3-phenyl-4-chloro-5-(1-fluoropropyl)]phenylpiperazine,
(188) 1-methyl-4-[3-(2-hydroxymethylphenyl)-4-chloro-5-(1-fluoropropyl)]phenylpiperazine,
(189) 1-ethyl-4-[3-(2-fluoromethylphenyl)-4-chloro-5-(1-fluoropropyl)]phenylpiperazine,
(190) 1-methyl-4-{3-(2-fluoromethylphenyl)-4-chloro-5-[1-fluoropropyl]}phenylpiperazine,
(191) 1-ethyl-4-{3-[2-(4-fluorotolyl)]-4-chloro-5-[1-fluoropropyl]}phenylpiperazine, (192) 1-[2-(2-pyridyl)ethyl]-4-[3-(2-tolyl)-4-chloro-5-(1-fluoropropyl)]phenylpiperazine,
(193) 1-[2-(2-pyridyl)ethyl]-4-[3-(2-cyanophenyl)-4-chloro-5-(1-fluoropropyl)]phenylpiperazine,
(194) 1-ethyl-4-[3-(2,6-xylyl)-4-chloro-5-(1-fluoropropyl)]phenylpiperazine,
(195) 1-ethyl-4-{3-(2-trifluoromethylphenyl)-4-chloro-5-[1-fluoropropyl]}phenylpiperazine,
(196) 1-ethyl-4-[3-(2-ethylphenyl)-4-chloro-5-(1-fluoropropyl)]phenylpiperazine,
(197) 1-(2-hydroxyethyl)-4-[3-(2-ethylphenyl)-4-chloro-5-(1-fluoropropyl)]phenylpiperazine,
(198) 1-(2-hydroxyethyl)-4-{3-(2-trifluoromethylphenyl)-4-chloro-5-[1-fluoropropyl]}phenylpiperazine,
(199) 1-methyl-4-{3-(2-tolyl)-4-chloro-5-[1-fluoropropyl]}phenylpiperazine, and
(200) 1-(2-hydroxyethyl)-4-{3-[2-(4-fluorotolyl)]-4-chloro-5-[1-fluoropropyl]}phenylpiperazine.

3. A biphenyl compound represented by the following formula (I) or pharmacologically acceptable salt thereof:

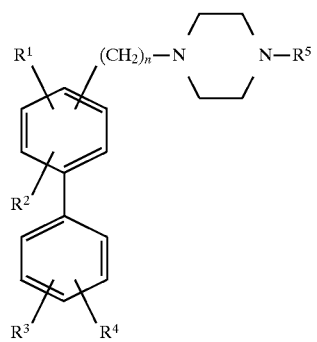

wherein:

$R^1$ is a halogenated alkyl;

$R^2$ is a halogen;

$R^3$ is a cyano;

$R^4$ is a hydrogen or a halogen;

$R^5$ is a hydroxy lower alkyl; and n is 0; or a pharmacologically acceptable salt thereof.

4. A biphenyl compound according to claim 3, having the formula:

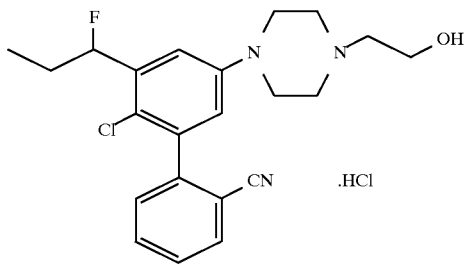

or a pharmacologically acceptable salt thereof.

5. A biphenyl compound according to claim 1, having the formula:

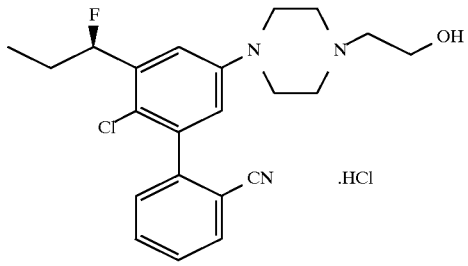

6. A biphenyl compound according to claim 1, having the formula:

* * * * *